US011633364B2

(12) United States Patent
Schentag et al.

(10) Patent No.: US 11,633,364 B2
(45) Date of Patent: Apr. 25, 2023

(54) METHODS OF TREATMENT USING CHOLESTOSOME VESICLES FOR INCORPORATION OF MOLECULES INTO CHYLOMICRONS

(71) Applicant: THERASYN SENSORS, INC, Eggertsville, NY (US)

(72) Inventors: Jerome J. Schentag, Amherst, NY (US); Mary P. McCourt, Amherst, NY (US); Lawrence Mielnicki, Buffalo, NY (US); Julie Hughes, Williamsville, NY (US)

(73) Assignee: THERASYN SENSORS, INC., Eggertsville, NY (US)

( * ) Notice: Subject to any disclaimer, the term of this patent is extended or adjusted under 35 U.S.C. 154(b) by 49 days.

(21) Appl. No.: 17/337,283

(22) Filed: Jun. 2, 2021

(65) Prior Publication Data
US 2022/0040116 A1 Feb. 10, 2022

Related U.S. Application Data

(60) Division of application No. 16/527,579, filed on Jul. 31, 2019, now Pat. No. 11,052,052, which is a continuation of application No. 15/603,992, filed on May 24, 2017, now Pat. No. 10,369,114, which is a continuation of application No. 14/776,307, filed as application No. PCT/US2014/027761 on Mar. 14, 2014, now Pat. No. 9,833,486.

(60) Provisional application No. 61/783,003, filed on Mar. 14, 2013.

(51) Int. Cl.
| A61K 9/51 | (2006.01) |
| A61K 9/127 | (2006.01) |
| A61K 31/12 | (2006.01) |
| A61K 31/137 | (2006.01) |
| A61K 31/19 | (2006.01) |
| A61K 31/546 | (2006.01) |
| A61K 31/7034 | (2006.01) |
| A61K 31/713 | (2006.01) |
| A61K 38/14 | (2006.01) |
| A61K 38/28 | (2006.01) |
| A61K 39/29 | (2006.01) |
| A61K 39/395 | (2006.01) |
| A61K 45/06 | (2006.01) |

(52) U.S. Cl.
CPC .............. *A61K 9/51* (2013.01); *A61K 9/127* (2013.01); *A61K 9/1275* (2013.01); *A61K 31/12* (2013.01); *A61K 31/137* (2013.01); *A61K 31/19* (2013.01); *A61K 31/546* (2013.01); *A61K 31/7034* (2013.01); *A61K 31/713* (2013.01); *A61K 38/14* (2013.01); *A61K 38/28* (2013.01); *A61K 39/29* (2013.01); *A61K 39/3955* (2013.01); *A61K 45/06* (2013.01)

(58) Field of Classification Search
CPC ........ A61K 9/51; A61K 31/12; A61K 31/137; A61K 31/19; A61K 31/546; A61K 31/7034; A61K 31/713; A61K 38/14; A61K 38/28; A61K 39/29; A61K 39/3955; A61K 45/06; A61K 9/1275; A61K 9/127; A61P 3/10; A61P 9/12; A61P 5/50; A61P 5/06; A61P 3/06; A61P 35/00; A61P 31/14; A61P 31/12; A61P 31/04; A61P 11/06
See application file for complete search history.

(56) References Cited

U.S. PATENT DOCUMENTS

| 4,544,545 A | 10/1985 | Ryan et al. |
| 5,013,556 A | 5/1991 | Woodle et al. |
| 5,049,389 A | 9/1991 | Radhakrishnan |
| 5,094,854 A | 5/1992 | Ogawa et al. |
| 5,288,499 A | 2/1994 | Janoff et al. |
| 5,844,075 A | 12/1998 | Kawakami et al. |
| 9,119,782 B2 | 9/2015 | McCourt |
| 9,693,968 B2 | 7/2017 | Schentag et al. |
| 9,693,969 B2 | 7/2017 | TheraSyn |

(Continued)

FOREIGN PATENT DOCUMENTS

| JP | 2009143963 A | 7/2009 |
| WO | 9203123 A1 | 3/1992 |

(Continued)

OTHER PUBLICATIONS

Giguere S, et al. Role of the 85-Kilobase Plasmid and Plasmid-Encoded Virulence-Associated Protein A in Intracellular Survival and Virulence of Rhodococcusequi. Infection and Immunity, 1999;67(7):3548-3557.

(Continued)

*Primary Examiner* — Robert A Wax
*Assistant Examiner* — Quanglong N Truong
(74) *Attorney, Agent, or Firm* — Henry D. Coleman; R. Neil Sudol

(57) ABSTRACT

The present invention is directed to a cargo-loaded cholesteryl ester nanoparticle with a hollow compartment ("cholestosome") consisting essentially of at least one non-ionic cholesteryl ester and one or more encapsulated active molecules which cannot appreciably pass through an enterocyte membrane in the absence of said molecule being loaded into said cholestosome, the cholestosome having a neutral surface and having the ability to pass into enterocytes in the manner of orally absorbed nutrient lipids using cell pathways to reach the golgi apparatus. Pursuant to the present invention, the novel cargo loaded cholestosomes according to the present invention are capable of depositing active molecules within cells of a patient or subject and effecting therapy or diagnosis of the patient or subject.

15 Claims, 30 Drawing Sheets

(56) References Cited

U.S. PATENT DOCUMENTS

| | | | |
|---|---|---|---|
| 9,833,486 | B2 | 12/2017 | Power et al. |
| 10,092,516 | B2 | 10/2018 | McCourt |
| 10,369,114 | B2 | 8/2019 | TheraSyn |
| 2004/0037874 | A1 | 2/2004 | Hong et al. |
| 2004/0052838 | A1 | 3/2004 | Naeff et al. |
| 2004/0197393 | A1 | 10/2004 | Smyth-Templeton et al. |
| 2006/0216255 | A1 | 9/2006 | Lee et al. |
| 2006/0286161 | A1 | 12/2006 | Panzner et al. |
| 2007/0014840 | A1 | 1/2007 | Lee et al. |
| 2007/0225264 | A1 | 9/2007 | McCourt |
| 2008/0241257 | A1 | 10/2008 | Popescu et al. |
| 2011/0046053 | A1 | 2/2011 | Kidron |
| 2013/0183270 | A1 | 7/2013 | Geho et al. |
| 2014/0199233 | A1 | 7/2014 | Nagy et al. |
| 2019/0060236 | A1 | 2/2019 | McCourt |
| 2019/0175515 | A1 | 6/2019 | Schentag et al. |

FOREIGN PATENT DOCUMENTS

| | | |
|---|---|---|
| WO | 2004098564 A2 | 11/2004 |
| WO | 2013148258 A1 | 10/2013 |
| WO | 2014152795 A2 | 9/2014 |
| WO | 2016156398 A1 | 4/2016 |

OTHER PUBLICATIONS

Yoshida K, et al. Effect of Tumor Size on Monoclonal Antibody Uptake in a Metastatic Model. Journal of Surgical Oncology, 1992;49:249-252.
Bussiere JL, et al. 60-Day Repeated Dose Inhalation Toxicity Study of an Anti-IgE Antibody in Cynomolgus Monkeys. SOT Annual Meeting, 1997;271.
Sweeney TD, et al. Pulmonry Delivery of Anti-IgE Rationale for Topical Delivery to the Airway, 2001.
Bleavins MR, et al. Cynomolgus monkeys (Macaca fascicularis) in preclinical immune function safety testing development of a delayed-type hypersensitivity procedure. Toxicology, 1995;95:103-112.
Ryffel B. Impact of Knockout Mice in Toxicology. Critical Reviews in Toxicology, 1997;27(2):135-154.
Congestive Heart Failure. American Heart Association (2006) http://www.americanheart.org/presenter.jhtml?identifier=4585.
Heart Attack, Stroke & Cariac Arrest Warning Sings. American Heart Association (2006) http://www.americanheart.org/presenter.jhtml?identifier=3053.
Bjorkhlem I, et al. Oxysterols: Friends, Foes or Just Fellow Passengers? Arteriosclerosis, Thrombosis, and Vascular Biology, 2002;22:734-742.
Christiansen LI. Preparation, Analysis and Cholesterol Lowering Effect of a Novel Microcrystalline . . . Suspension in Oil and Phase Behavior of Beta-sitosterol with Cholesterol. Academic Dissertation at the University of Helsinki, Finland (2002).
Dorset DL, et al. Co-solubility in binary phospohlipid crystals. Biochimica et Biophysica Acta, 1987;903:319-332.
Dorset DL. Cholesteryl esters of saturated fatty acids: cosolubility and fractionation of binary mixtures. Journal of Lipid Research, 1987;28:993-1005.
Dorset DL. Co-solubility of saturated cholesteryl esters: a comparison of calculated and experimental binary phase diagrams. Biochimica et Biophysica Acta, 1988;963:88-98.
Dorset DL. Binary phase behavior of cholestryl oleate with cholesteryl linoleate. Biochimica et Biophysica Acta, 1990;1046:57-63.
Dorset DL. Eutectic interactions in binary systems containing cholesterol, cholesteryl esters and triacylglycerols. Biochimica et Biophysica Acta, 1990;1047:112-120.
Dorset DL. Binary phase behavior of angiotoxic oxidized cholesterols with cholesterol. Biochimica et Biophysica Acta, 1992;1127:293-297.
Garcia-Cruset S, et al. Oxysterols in cap and core oh human advanced atherosclerotic lesions. Free Radical Research, 1999;30:341-351.

Guo W, et al. Phase Behavior and Crystalline Structures of Cholesteryl Ester Mixtures: A C-13 MASNMR Study. Biophysical Journal, 1995;68:341-351.
Hulten LM, et al. Oxysterols persent in atherosclerotic tissue decrease the expression of lipoprotein fipase messenger RNA inhuman monocyte-derived macrophages. The Journal of Clinical Investigation, 1996;97:461-468.
Leoni V. On the possible use of oxysterols for the diagnosis and evaluation of patients with neurological and neurodegenerative diseases. Karolinska Institutel Thesis, Stockholm, Sweden, 2005.
Linseisen J, et al. Plasma 7beta-hydroxycholesterol as a possible predictor of lung cancer risk. Cancer Epidemoil Prev, 2002;11:1630-1637.
Lizard G, et al. Characterization and Comparison of the Mode of Cell Death . . . by 7beta-Hydroxycholesterol and 7-Ketocholesterol in the Cells of the Vascular Wall. Arteriosclerosis, Thrombosis and Vascular Biology, 1999;19:1190-1200.
Mahadevan V, et al. Preparation of cholesterol esters of long-chain fatty acids and characterization of cholestryl arachidonate Journal of Lipid Research, 1962;3:106-110.
Marcu L, et al. Arterial flourescent components involved in artherosclerotic plagque instability: differentiation by time-resolved flourescence spectroscopy, 2001.
McCourt MP, et al. X-ray crystal structure of cytotoxic oxidized cholesterols: 7-ketocholesterol and 25-hydroxycholesterol. Journal of Lipid Research, 1997;38:1014-1021.
Micheletta F, et al. Vitamin E Supplementation in Patients with Carotid Atherosclerosis. Arterioschlerosis, Thrombosis, and Vascular Biology, 2004;24:136.
Nelson DL, et al. Lehninger Principels of Biochemistry fourthedition. New York: WH Freeman and Company, 2005.
Raff LM. Principles of Physical Chemistry. Upper Sakkle River, NJ: Prentice Hall (2001).
Ringseis R, et al. Insufficient dietary vitamin e increases the concentration of 7beta-hydroxycholesterol in tissues of rats feed salmon oil. The Journal of Nutrition, 2002;132:2732-2735.
Rodriguez IR, et al. Cytotoxicity of Oxidized Low-Density Lipoprotein in Cultures RPE Cells is Dependent on the Formation of 7-Ketocholestrol. Investigative Ophthalmology and Visual Science, 2004;45:2830-2837.
Shands Health Care. Transcient ischemic attack (TIA). 2006. http://www.shands.org/health/information/article/000730.htm.
Sigma-Aldrich Corporation. Material Safety Data Sheet, 2006, http://www.sigma.com.
Tontonoz PA, et al. Regulation of macrophage gene expression by peroxisome-proliferator-activated receptor [gamme]: implications for cardiovascular disease. Current Opinion in Lipidology, 1999;10:485-490.
Wikipedia. Apoptosis (2006), http://en.wikipedia.org/wiki/Apoptosis.
Wohlfeil ER, et al. 25-Hydroxycholesterol Increases Eicosanoids and Alters Morphology in Cultures Pulmonary Artery Smooth Muscle and Endothelial Cells. Arteriosclerosis, Thrombosis, and Vascular Biology, 1999;19:2901-2908.
Funakoshi K, et al. Formation of Giant Lipid Vesiclelike Compartments from a Planar Lipid Membrane by a Pulsed Jet Flow J Am Chem Soc, 2007;129:12608-12609.
Frankenburg S, et al. Recombinant hydrophilic human gp100: uptake by dendritic cells and stimulation of autologous CD8+ lymphocytes from melanoma patients. Immunology Letters, 2004;94:253-259.
Sahin NO. Niosomes as Nanocarrier Systems. IN: Nanomaterials and Nanosystems for Biomedical Applications. Edited by M. Mozafari Netherlands. Springer press, 2007, Chapter 4: p. 67-81.
Prasad S, et al. Polymer nanoparticles containing lysates as antigen delivery vehicles for dendritic cell-bases antitumor immunotherapy. Nanomedicine, 2011;7(1):1-10.
Lochmatter P, et al. Drug-specific in vitro release of IL-2, IL-5, IL-13, and IFN-gamma in patients with delayed-type drug hypersensitivity. Allergy, 2009;64(9):1269-1278.
Huan Xu, et al. Preparation and Characterization of pH-Sensitive Vesicles Made of Cholesteryl Hemisuccinate. Drug Development and Industrial Pharmacy, 2008;34(2):134-141.

(56) References Cited

OTHER PUBLICATIONS

Bleavins MR, et al. Cynomolgus monkeys (Macaca fascicularis) in preciinicai immune function safety testing: development of a delayed-type hypersensitivity procedure. Toxicology, 1995;95:103-112.

Bjorkhlem I, et al. Oxysterols: Friends, Foes or Just Feilow Passengers? Arteriosclerosis, Thrombosis, and Vascular Biology, 2002;22:734-742.

Dorset Dl. Co-solubility of saturated cholesteryl esters: a comparison of calculated and experimental binary phase diagrams. Biochimica et Biophysica Acta, 1938;963:88-93.

Linseisen J, et al. Plasma 7beta-hydroxychoiesterol as a possible predictor of lung cancer risk. Cancer Epidemoil Prev, 2002;11:1630-1637.

Lizard G, et al. Characterization and Comparison of the Mode of Cell Death . . . by 7beta-Hydroxycholesterol and 7-Ketocholesterol in the Celis of the Vascular Wall. Arteriosclerosis, Thrombosis and Vascular Biology, 1999;19:1190-1200.

Marcu L, et al. Arterial flourescent components involved in artheroscierotic plagque instability: differentiation by time-resolved flourescence spectroscopy, 2001.

Ringseis R, et al. Insufficient dietary vitamin e increases the concentration of 7beta-bydroxycholesterol in tissues of rats feed salmon oil. The Journal of Nutrition, 2002;132:2732-2735.

Shands Health Care. Transcient ischemic attack (TIA). 2006. http://www.sharids.org/heaith/information/article/000730.htm.

Funakoshi K, et al. Formation of Giant Lipid Vesicieiike Compartments from a Planar Lipid Membrane by a Pulsed Jet Flow. J AM CHEM SOC, 2007;129:12608-12609.

Sahin, N. O.; Niosomes as Nanocarrier Systems. IN: Nanomaterials and Nanosystems for Biomedical Applications. Edited by M. Mozafari Netherlands: Springer press, 2007, Chapter 4, pp. 67-81.

Lochmatter P, et al. Drug-specific in vitro release of IL-2, IL-5, IL-13, and IFN- gamma in patients with deiayed-type drug hypersensitivity. Allergy, 2009, 64(9):1269-1278.

Xu H, et al. Preparation and Characterization of pH-Sensitive Vesicles Made of Cholesteryl Hemisuccinate. Drug Development and Industrial Pharmacy, 2008;34(2):134-141.

A. FITC vancomycin 0.83 mcg/ml cholestosomes

B. FITC vancomycin 83 mcg/ml

C. FITC vancomycin 666 mcg/ml

A. FITC-Insulin-Cholestosomes (no Caco-2 cells, 2hr)

B. FITC-Insulin cholestosome Chylomicrons (made by Caco-2 cells, 2hr)

FIG. 30

Comparison of properties between Cholestosomes and alternative delivery modalities.

|  | Cholestosome™ | Synthetic Polymers | Liposome | Carrier Proteins |
|---|---|---|---|---|
| Stability in Bloodstream | + | + | + | + |
| Survivability in GI tract | +++ | + | + | + |
| Design Flexibility | +++ | + | +/- | - |
| Manufacturability | +++ | + | ++ | + |
| Efficacy | + | + | + | + |
| Encapsulation Efficiency | +++ | + | + | + |

METHODS OF TREATMENT USING CHOLESTOSOME VESICLES FOR INCORPORATION OF MOLECULES INTO CHYLOMICRONS

RELATED APPLICATIONS

This application is a divisional application of U.S. application Ser. No. 16/527,579 filed on Jul. 31, 2019, which is a continuation application of U.S. application Ser. No. 15/603,992 filed on May 24, 2017 of the same title, which is a continuation application of U.S. application Ser. No. 14/776,307 filed on Sep. 14, 2015 of the same title, which is a United States national phase patent application based upon international patent application number PCT/US2014/027761 filed Mar. 14, 2014, which claims the benefit of priority of provisional application no. U.S. 61/783,003, filed Mar. 14, 2013, of identical title, the entire contents of which three applications are incorporated by reference herein.

FIELD OF THE INVENTION

The present invention is directed to a cargo-loaded cholesteryl ester (lipid) nanoparticle with a hollow compartment ("cholestosome") consisting essentially of at least one non-ionic cholesteryl ester and one or more encapsulated active molecules which, in the absence of encapsulation in cholestosomes cannot appreciably pass through an enterocyte membrane in the absence of said molecule being loaded into said cholestosome, the cholestosome having a neutral surface and having the ability to pass into enterocytes in the manner of orally absorbed nutrient lipids using cell pathways to reach the golgi apparatus. Pursuant to the present invention, the novel cargo loaded cholestosomes according to the present invention are capable of depositing active molecules within cells of a patient or subject and effecting therapy or diagnosis of the patient or subject. The compositions according to the present invention are substantially more active than compositions of the prior art which do not use cholesteryl ester nanoparticles.

In one embodiment, the invention provides a cholesteryl ester nanoparticle pharmaceutical composition comprising an active molecule ("cargo-loaded cholestosome"), for example, a pharmaceutically-active agent (which term includes therapeutic and diagnostic agents) which is encapsulated by a surface layer of neutral charge comprising one or more cholesteryl esters produced from cholesterol and one or more saturated or unsaturated fatty acids. The cholestosomes according to the present invention encapsulate one or more different active molecules of wide variety of size and weight, especially pharmaceutical active molecules which are difficult to deliver using prior art methods, including liposomes.

Pursuant to the present invention, the cargo-loaded cholestosomes, after administration to a patient or subject, are incorporated intact into chylomicrons (generally, after uptake into intestinal enterocytes) to produce a nanoparticle containing chylomicrons and said nanoparticle containing chylomicrons are delivered into the lymphatics and subsequently into arterial blood and to all cells receiving said arterial blood supply, whereupon after docking of the chylomicrons with cells, the cholestosome is delivered intact into said cells, wherein said cholestosome is disassembled, releasing the encapsulated active molecules inside the membrane of said cells. The impact of the present invention is to directly deliver active molecules inside cells to effect therapy or diagnosis.

Cholesteryl esters are selected for the composition of the nanoparticle, based on their reactivity with cholesterol transporters on the surface of intestinal (duodenal) enterocytes, which facilitates their rapid and complete uptake into the enterocytes. Once inside, cholesterol ester nanoparticles offer the added benefit of protection of the contents of the nanoparticle during chylomicron formation inside the enterocyte. Additional favorable properties of the cholesteryl ester components of the nanoparticle are 1) their surface neutral charge allowing the enterocytes to see these particles as food components, 2) their entire composition of the cholestosome from safe dietary ingredients, and 3) in particular on their potential to "pack" with each other and the requirements of the pharmaceuticals to be incorporated in the nanoparticles themselves. Liposome manufacturing technology teaches away from the use of cholesteryl esters in vesicles with neutral surfaces, in fact, if nanoparticles are made of phospholipids in the manner of liposomes disclosed in the art, every one of the beneficial features of the present invention is lost.

Pharmaceutical compositions and oral methods of treatment of the invention, when encapsulated with said cholesteryl esters, enable chylomicron-targeted intracellular delivery of a variety of active ingredients that are, in an unprotected state, ineffective due to degradation in vivo. For example, the invention enables effective delivery of macromolecules useful in the treatment of inflammation-associated metabolic disorders as defined herein, vaccines to specific sites in the body, genetic materials inside cells where they act in the ribosomes and nuclei, and even topical delivery on the skin with the potential for passage of the skin barrier in some specific embodiments. Other methods of treating disease states and/or conditions using compositions according to the present invention are also disclosed. Virtually any active molecule can be delivered efficiently into target cells of a patient or subject resulting in effective therapy unmatched by delivery methods of the prior art. Methods of treating disease states and conditions by administering compositions according to the present invention to a patient in need represent additional embodiments according to the present invention. Effective dosages of compositions for methods of treatment embodiments according to the present invention may range from as little as one mg or less up to one gram or more per day. Other effective dosages will depend on the size and age of the patient or subject, the general health of the patient among a number of other facts. Dosages contemplated within the range of less than about 0.001 mg/kg/day up to about 100 mg/kg/day or more with ranges of about 0.01 mg/kg/day to about 25 mg/kg/day being more often utilized.

BACKGROUND OF THE INVENTION

There are many new therapeutic products where a large protein or other macromolecule is serving a role as a therapeutic or diagnostic substance. For treatment of chronic conditions, there is a high interest in delivery of large molecules via non intravenous routes such as subcutaneous injection, in order to improve patient convenience and compliance. Oral administration of peptides (including polypeptides such as monoclonal antibodies), proteins, and DNA would be much more convenient and no less safe. However, many believe it is not possible to achieve oral absorption of large protein molecules in humans. Because orally administered molecules such as proteins, peptides and genetic material are either digested in the gastrointestinal (GI) tract or fail to diffuse across the cellular membrane of the enterocytes, or both, it is widely believed that parenteral delivery is the only reliable way to administer such active ingredients. When given by the oral route, proteins are not absorbed intact by intestinal cells. Rather, they are broken down by enzymes into amino acid constituents and thus most of the therapeutic proteins produced by the biotechnology industry are completely susceptible to gastrointestinal degradation pathways.

The usual administration route, parenteral administration, is on the other hand suboptimal for macromolecular delivery for many reasons. Compared to oral administration, parenteral delivery is more expensive and requires hardware and more hi y trained personnel.

Even after parenteral administration, the macromolecules encounter problems with passage of membranes. They are excluded from many target cells, and as a result they circulate in blood until cleared or degraded but may never successfully enter body cells. Macromolecules may fail to pass regional barriers such as the blood brain barrier, effectively preventing targeting of macromolecules to selected organs and tissues such as brain. This may be an underlying reason for clinical trial failure of many of the monoclonal antibodies against targets in the amyloid pathway to clear amyloid from the brain and their lack of sufficient activity to reverse Alzheimer's disease. In general, the large size and lack of lipid solubility of these proteins may limit the intracellular effectiveness of an otherwise novel target monoclonal antibody.

Clearly, success with oral proteins depends on creation of novel formulations that overcome acid and/or enzymatic degradation in the GI tract and then overcome low permeability across an intestinal enterocyte membrane, and finally overcome the current inability to pass into the cells on the other side.

Recent formulations that overcome only the gastrointestinal degradation problems might achieve ~5% absorption. This step is clearly important but insufficient, so it remains necessary to further improve the poor bioavailability of proteins with a novel means of taking up proteins into enterocytes, and this is disclosed herein for the first time.

Furthermore, the delivery means of the present invention is the first to solve the next problem, that of intracellular delivery, by means of a transformative step performed on the nanoparticle, the incorporation of the lipid nanoparticle into chylomicrons with its molecular payload intact. Successful incorporation into chylomicrons is only possible with the use of herein disclosed cholesteryl esters to build the lipid nanoparticle.

Prior attempts to deliver macromolecules for oral absorption by the enterocytes have relied on encapsulation in nano sized particles. Most of the work has been conducted with liposomes of varying composition.

As explained in the following excerpt from United States Patent Application Document No. 20110229529, liposomes have not solved the aforementioned problems. "Liposomes have been widely used as a delivery vehicle for small molecules; however, it remains difficult to achieve high levels of encapsulation for many macromolecular drugs within liposomes. Furthermore, many drug formulations leak from liposomes too quickly to maintain useful drug delivery kinetics. While drug delivery by micro- and nanoparticles can encapsulate proteins and small-molecule drugs, this still typically yields very low total mass encapsulated drug per mass of particles, typically on the order of about 1:1000 to 1:10,000 mass ratio, of in this case protein: phospholipid mixture (see for example U.S. Pat. No. 7,662,405). In addition, the organic solvents used in polymer particle synthesis and hydrophobic/acidic environment within these particles can lead to destruction of therapeutics. (See Zhu et al. Nat. Biotechnol, 2000 18:52-57.)"

There are other problems with use of liposomes even beyond the aforementioned small amount of encapsulation of water soluble proteins or small molecules. Specifically, the contents of most liposomes are phospholipids, typically phosphatidylcholine. These nano sized lipid particles are highly positively charged and thereby repelled by the outer membranes of enterocytes and also by cell membranes of peripheral cells.

Phospholipid based liposomes are thus not orally absorbed and are also not able to pass their contents into cells when injected parenterally. Thus no liposome of current composition is suitable for encapsulation of proteins or peptides (including polypeptides such as monoclonal antibodies), and even it one could load enough molecule into these particles, they would not solve the oral absorption problem. Furthermore, no phosphatidyl choline based liposome can be incorporated into a chylomicron with its molecular payload intact.

Tseng and colleagues described these problems in 2007 (Tseng et al, J of Medical and biological engineering 2007; 27: 29-34; the Tseng article was titled Liposomes incorporated with cholesterol for drug release triggered by magnetic field) and therein tested the hypothesis that adding cholesterol to Phosphatidyl choline liposomes would alter these properties and improve loading. They found only modest improvement in loading, and there was not sufficient cholesterol to change the positive charge of the outer surface. Of greater significance to them was their observation that increased cholesterol in the liposome prevented exit of the loaded molecules. "An increase of the cholesterol content in liposomes results in a dramatic decrease in membrane permeability for non-electrolyte and electrolyte solutes. An optimized drug delivery via liposomes requires the liposome carrier to ultimately become permeable and release the encapsulated drug on the targeted area, but it also requires high stability in the bloodstream" Thus entire the liposomal field lamely abandoned cholesterol as a component of liposomes, citing a deterioration in the molecular RELEASE properties of cholesterol containing liposomes and teaching the entire field away from the particular nanoparticles of the present invention.

It should be noted in the present invention, that inventors have chosen the high loading and slow release properties cholesteryl esters for the specific purposes of protecting the molecule during its journey across membranes of the GI tract enterocytes, then into chylomicrons, then through the cell membranes. Unpacking of cholestosome encapsulated proteins only occurs inside the body cells, which confers a great advantage to the disclosed delivery method over any current system. We disclose the analogy to the Trojan Horse, invented of course before there were patents, but not used heretofore for a drug delivery system.

It should also be noted that the disclosed process works as intended only with cholesteryl esters, as only these molecules are handled intact among lipids all the way to intracellular delivery by chylomicrons.

Given the limitations of existing macromolecule therapies, the need continues to exist for formulations and treatments that administer pharmaceutically active macromolecules in a more convenient way such as orally, and the need continues for formulations that allow proteins and other molecules to enter cells. The use of one formulation to accomplish both aspects is the primary subject of the present invention.

SUMMARY OF THE INVENTION

In one embodiment, the invention provides a cholesteryl ester nanoparticle pharmaceutical composition comprising a pharmaceutically-active agent (cargo-loaded cholestosome) which is encapsulated by a surface layer comprising one or more non-ionic cholesteryl esters. The cholesteryl esters used in the present invention are produced from cholesterol (as defined herein) and one or more saturated or unsaturated fatty acids as otherwise described herein, preferably a $C_4$-$C_{36}$ fatty acid, often a $C_8$-$C_{26}$ fatty acid, more often a fatty acid selected from the group consisting Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, Cerotic acid or a mixture thereof. The cholestosomes according to the present invention are avidly taken up by the enterocytes of the gastrointestinal tract, and are rapidly transferred, along with their contents, into chylomicrons, thereby providing a means of transporting the encapsulated molecules directly into body cells, as well as incidentally and importantly, bypassing hepatic first pass uptake pathways in the process. Quite unexpectedly, the presently claimed cargo-loaded cholesteryl ester vesicles are able to deliver a wide variety of molecules, including peptides (including polypeptides such as monoclonal antibodies) and proteins and other macromolecules, including polynucleotides such as DNA and RNA, macromolecular antimicrobial agents (anti-bacterial, anti-viral, anti-fungal, anti-parasitic and anti-prion) which vary greatly in size and molecular weight, into cells such that therapy or diagnosis is effected.

In the present invention, the mass ratio of the active molecule (which preferably includes a pharmaceutically-active agent), to one or more cholesteryl esters is between about 4:96 to about 96:4, about 10:90 to about 96:4, often about 10:90 to about 96:4, often about 20:80 to about 90:10, about 20:80 to about 50:50, about 50:50 to about 96:4, about 90:10 to about 96:4.

Physical Properties

In certain embodiments, the pharmaceutical composition is a unilamellar vesicle in which between about 10% to about 98%, about 20% to about 96%, often about 50% to about 96%, often about 90% to about 96% of the vesicle's volume is occupied by the pharmaceutically-active agent.

In another embodiment, an interdigitated alternating alkyl chain model is used to maximize the mass ratio of the active molecule, including a pharmaceutically-active agent to one or more cholesteryl esters by selecting the one or more cholesteryl esters based on pharmaceutically-active agent-cholesterol ester functional group interaction. Example 2, infra describes formulation criteria which ensure optimal pharmaceutically-active agent-cholesteryl ester functional group interaction.

In another embodiment, the pharmaceutical composition is a cholestosome vesicle made by a process comprising reacting one or more of the cholesteryl esters in diethyl ether, removing the resultant organic phase under vacuum and introducing an aqueous phase.

In still another embodiment, cholesteryl esters are selected based on their reactivity with cholesterol transporters on the surface of duodenal enterocytes and ability to remain intact in enterocytes until incorporation into chylomicrons.

In embodiments according to the invention, the cholesteryl ester is obtained by esterifying cholesterol with a $C_4$ to $C_{36}$ saturated or unsaturated fatty acid, often a $C_8$ to $C_{26}$ fatty acid. In certain embodiments, the cholesteryl esters is often selected from the group consisting of cholesteryl myristate, cholesteryl laurate, cholesteryl dodeconate, cholesteryl palmitate, cholesteryl arachidonate, cholesteryl behenate, cholesteryl linoleate, cholesteryl linolenate, cholesteryl oleate and cholesteryl stearate.

Anti-Infective Molecules in Cholestosomes

In a preferred embodiment, the invention provides a cargo-loaded cholestosome pharmaceutical composition comprising an anti-infective compound (1) which is selected from the group consisting of miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole and ciclopiroxolamine, micafungin, caspofungin, anidulafungin, vancomycin, daptomycin, oritavancin, WAP 8294A, dalbavancin, ceftaroline, cefepime, ceftriaxone, ceftazidime, Quinupristin/Dalfopristin (synercid), fosfomycin, colistin, tigecycline and (2) which is encapsulated by a surface layer consisting essentially of a cholesteryl ester as otherwise described herein. This composition can be used to treat an infection and can be administered topically including orally or intravaginally.

Peptide Molecules Insulin and Beyond

In another preferred embodiment, the invention provides a cargo-loaded cholestosome pharmaceutical composition comprising a peptide which is often selected from the group consisting of a hydrophilic peptide, human growth hormone, prolactin, oxytocin, calcitonin, bovine growth hormone, porcine growth hormone, Ghrelin, GLP-1, PYY36, Oxyntomodulin, GLP-2. Glucagon, and insulin, and which is encapsulated by a cholesteryl ester as otherwise described herein. This composition can be administered to increase milk production, improve structure or function of organs and tissues such as pancreas or liver, to increase or initiate growth of a mammal or to administer insulin in those individuals to whom insulin treatment is beneficial.

In certain embodiments, the surface layer of the nanoparticle is further enterically coated to prevent degradation of the pharmaceutical composition in the gastrointestinal tract.

In certain embodiments, the surface layer of the cargo-loaded cholestosome remains intact at a pH range of between about 2 to about 14.

In other embodiments, the cargo-loaded cholestosome is a unilamellar vesicle having a diameter of about 5 nm up to more than 10,000 nm (10 micrometers), about 10 nm to about 1000 nm, often about 50 nm to about 750 nm, about 100 to about 500 nm, about 200 to about 300 nm, depending upon whether the material is subjected to an extrusion step or is unextruded. Accordingly, it is noted that larger cholestosomes are used when the active molecule is larger and small cholestosomes are used when the active molecule is smaller.

Features of Oral Absorption and Favorable Associated Properties

While not being limited by way of theory, the present invention enables oral delivery of a formulation that encapsulates a molecule into a cholestosome which enters (31 enterocytes through molecular recognition, is ingested, incorporates into a chylomicron, thereby fully protecting the integrity of the molecule in the gastrointestinal tract, in the enterocyte, in the lymphatic system, in the blood, and across the membranes of body cells. Formulations of the invention do not release an active ingredient until it has been taken into the cells of the body. Features of this invention thus include the following:

1) complete passage of Caco2 enterocyte barrier;
2) complete passage of cellular membrane barrier;
3) a method of intracellular delivery that largely avoids endosome uptake;
4) oral delivery is independent of active molecule size, charge, binding or degradation pathways, although the surface of the cargo-loaded cholestosome is itself neutral;
5) active ingredients circulate in lymphatics around the liver—an oral delivery method that avoids first pass hepatic uptake; and
6) molecule delivery is facilitated by apolipoprotein attachments to surfaces of chylomicrons, capable of docking with cells and intracellular loading, followed by unpacking of encapsulated molecules in cytoplasm.

Accordingly, cargo-loaded cholestosomes according to the present invention are capable of delivering cargo (i.e., active molecules) to a concentration within cells of a patient or subject to whom the present compositions are administered (preferably, orally) of at least 2 times that which is provided in the absence of administration in cholestosomes (i.e., by conventional pharmaceutical delivery means, including delivery in liposomes). In most embodiments, the present invention delivers active molecules within cells to a concentration at least 10 times, 25 times, 50 times, 100 times, 250 times, 500 times and 1,000 times or more that which is provided in the absence of cholestosomes. Thus, the present invention provides a means to encapsulate molecules of a variety of size and molecular weight which heretofore could not be accommodated (itself an unexpected result) and regardless of size, the present compositions are capable of delivering active molecules to targets in cells at concentrations much higher levels than the prior art.

These and other aspects of the invention are described in further detail in the Detailed Description of the Invention.

BRIEF DESCRIPTION OF THE FIGURES

FIG. 30, shows a comparison of properties between Cholestosomes and alternative delivery modalities evidences that cholestosomes are superior or at least equal in all categories. One particularly important aspect of this comparison is that nearly any molecule can be encapsulated into a cholestosome without altering the molecule itself. This feature is not shared with other delivery systems, which tend to be specific to the molecule itself.

DETAILED DESCRIPTION OF THE INVENTION

Figure 1:
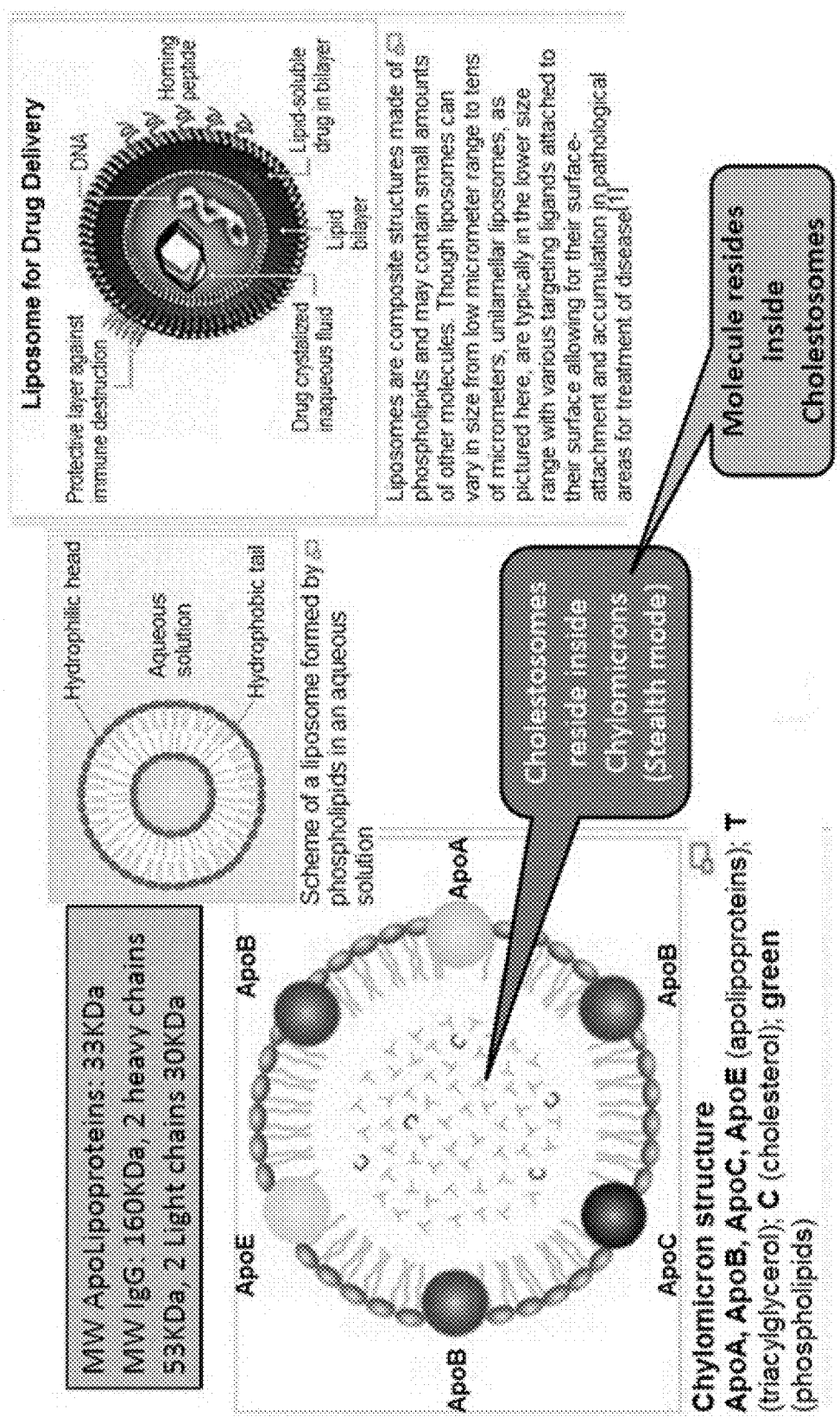
FIG. 1 shows diagrams comparing structural properties of chylomicrons, cholestosomes and liposomes, and assembly of a chylomicron containing a cholestosome encapsulated molecule. The illustration shows the molecule within the cholestosome prior to the incorporation of the cholestosome into the chylomicron. The incorporation of Apolipoprotein (APO) structures into chylomicrons allows them to dock with cells and release their contents, which include the cholestosome, and its contents. Liposomes by contrast are a completely different physical structure, primarily composed of phospholipids and having a positively charged surface. Liposomes with positive charges are not taken into the enterocytes and thus they cannot enter into chylomicrons. Liposomes are typically cleared primarily by the liver after they are injected intravenously. Cholestosomes and chylomicrons bypass the liver via lymphatic channels, and that is the primary reason they load encapsulated constructs into cells.

Cholestosomes are Unique and Novel Over any Prior Art

Cholestosomes pursuant to the present invention are unique among delivery systems for molecules. Unique among drug delivery means, the inventors have successfully disguised proteins and other molecules and chemical compounds as components commonly known in the art as food. Most specifically, the chosen materials for oral uptake are dietary cholesteryl esters. Surprisingly the cholesteryl esters provide a unique cholesteryl ester nanoparticle having the following properties that differentiate cholestosome encapsulated products (especially macromolecules which cannot otherwise be delivered to patients with any real measure of success) over liposomes or any other nanoparticle:

1. All component materials of the delivery means and system are common dietary ingredients, and total dosage of these substances per day in most applications will be less than from food.
2. Working temperature for encapsulation in cholestosomes is often 35-45 degrees centigrade, which is an optimal temperature for the stability of peptides and proteins in their body circulating forms.
3. Said Delivery means will offer all favorable aspects without concern for molecular size, charge, binding or degradation pathways
4. Cholestosome encapsulated proteins show complete passage of Caco2 enterocyte barrier, and are incorporated intact into chylomicrons
5. Bypass of the liver and associated first pass clearance pathways
6. Cholestosomes and the chylomicrons that contain them, provide protection for molecules as they pass cell membranes from oral intake all the way to intracellular uptake
7. Docking with cells; Quantitative intracellular loading; Complete passage of cellular membrane barrier
8. Unpacking of encapsulated contents in cytoplasm by cholesteryl ester hydrolases, an endogenous pathway.
9. Robust intracellular concentration of payload molecules at intracellular sites, yet cholestosomes do not use endosome uptake pathways
10. Cholestosomes and their encapsulated contents are distributed into all cells when incorporated into native formed chylomicrons While some deliver systems may achieve one or a small number of these 9 features, there is no other delivery system that can achieve this wide array of favorable properties, especially when the delivery system enables oral use of heretofore unabsorbed proteins, and does not alter the payload molecules and can be employed for essentially any molecule or chemical compound. Cholestosomes are the first intracellular delivery system that can be applied to any molecule. In fact, cholestosomes are at least as efficient with macromolecules, especially including proteins, peptides, polynucleotides (RNA and DNA, including, for example, naked DNA, plasmid DNA, interfering RNA or "RNAi", including small interfering RNA or "siRNA", small hairpin "shRNA", bifunctional shRNA, microRNA and various oligonucleotides of DNA and RNA, among others) and macromolecular antibiotics, among others, as they are with small molecules.

Because of the unique mechanism of delivering active molecules to a target within cells of a patient or subject, cargo-loaded cholestosomes according to the present invention are capable of delivering cargo (i.e., active molecules) within cells of a patient or subject to whom the present compositions are administered (preferably, orally) to a concentration of at least 2 times that which is provided in the absence of cholestosomes (i.e., by conventional pharmaceutical delivery means, including delivery in liposomes). In most embodiments, the present invention delivers active molecules within cells to a concentration at least 10 times, 25 times, 50 times, 100 times, 250 times, 500 times and 1,000 times or more that which is provided (delivered into cells) in the absence of cholestosomes.

As cholestosomes are novel in relation to prior art for molecule and chemical compound delivery, the inventors provide detailed comparison information to the reader in order to point out why prior art does not disclose any similar system;

Following these comparisons, Non-limiting examples will be provided.

The following terms are used throughout the specification to describe the present invention. Where a term is not given a specific definition herein, that term is to be given the same meaning as understood by those of ordinary skill in the art. The definitions given to the disease states or conditions which may be treated using one or more of the lipid nanoparticle encapsulated compounds according to the present invention are those which are generally known in the art.

It is noted that, as used in this specification and the appended claims, the singular forms "a," "an," and "the," include plural reference unless expressly and unequivocally limited to one reference. Thus, for example, reference to "a compound" includes two or more different compounds. As used herein, the term "include" and its grammatical variants are intended to be non-limiting, such that recitation of items in a list is not to the exclusion of other like items that can be substituted or other items that can be added to the listed items.

Cholesterol has vital structural roles in membranes and in lipid metabolism in general. It is a biosynthetic precursor of bile acids, vitamin D and steroid hormones (glucocorticoids, oestrogens, progesterones, androgens and aldosterone). In addition, it contributes to the development and working of the central nervous system, and it has major functions in signal transduction and sperm development. It is found in covalent linkage to specific membrane proteins or proteolipids ('hedgehog' proteins), which have vital functions in embryonic development.

Cholesterol esters, preferably with long-chain fatty acids linked to the hydroxyl group (often prepared from fatty acids containing at least eight up to 26 carbon atoms), are much less polar than free cholesterol and appear to be the preferred form for transport in plasma and as a biologically inert storage (de-toxification) form. They do not contribute to biological membranes but are packed into intracellular lipid particles.

Cholesterol ester hydrolases in animals liberate cholesterol and free fatty acids from the ester form, when required for membrane and lipoprotein formation. They also provide cholesterol for hormone synthesis in adrenal cells. Many cholesterol ester hydrolases have been identified, including a carboxyl ester hydrolase, a lysosomal acid cholesterol ester lipase, hormone-sensitive lipase and hepatic cytosolic cholesterol ester hydrolase. These are located in many different tissues and organelles and have multiple functions.

The applicants disclose a novel delivery technology which encapsulates molecules in a cholesteryl ester particle called a cholestosome, and after this particle is orally absorbed by cells of the intestine, it is placed into chylomicrons for delivery to all body cells via lymphatic transport. After this nanoparticle is taken up into cells from the chylomicron transport particle, the cholesterol ester hydrolases unpack the particle and liberate the molecule at the intracellular site.

Relevant background information regarding the structure of the cholestosomes in this application is found in United States Patent Application Document No. 20070225264, filed Mar. 20, 2007 and entitled "Drug Delivery Means".

Principles of interdigitation as used herein are known to those of ordinary skill in the art. See e.g. Yeagle, The Structure of Biological Membranes (CRC Press 2010).

"Chylomicrons" are very large, heterogeneous, lipid-rich particles ranging in diameter from about 750 to 40,000 nm. They are formed in the enterocytes of the GI tract and function to transport dietary fat and fat-soluble vitamins to cells via circulating in the bloodstream. A diagram of the formation of chylomicrons from cholestosomes and other lipid particles is shown as FIG. 1. The size heterogeneity of the secreted chylomicron particles depends on the rate of fat absorption, type and amount of fat absorbed. When cholestosomes are very large, the resulting chylomicrons that incorporate these large cholestosomes can be larger as well.

"Cholestosomes" are stable in the adverse conditions of the GI tract, possess greater design flexibility, and exhibit greater encapsulation efficiency for a wide variety of molecules, and have advantages of easier manufacturability. These favorable cholestosome properties are emphasized in FIG. 30, which compares delivery systems. The structural differences between cholestosomes and liposomes confer on cholestosomes different physical and chemical properties and therefore permit them superiority in desired properties and functions. For example, cholestosomes have been shown to be stable over a wide pH range from 2 to 13. In contrast, according to a 2005 review article in the Journal of Molecular structure describing liposomes, "owing to the small resistance of liposomes to gastric juice (pH 1.9), enzymes of the alimentary canal and bile acids in the intestine (pH 8) their application per us is useless." Cholestosomes resist pH degradation and therefore have the potential to be used as a primary means for oral delivery of molecules, a particularly novel aspect of the present invention.

A "cargo-loaded cholestosome" refers to a cholestosome which has encapsulated a pharmaceutically active agent and contains the agent principally, although not necessarily exclusively, in the core of the cholestosome vesicle.

Secondly, the structural features based on the interaction of the cholesteryl esters confers electrostatic surface properties which are calculated to be similar to PEG surfaces which liposomes use to confer enhanced time in the blood system. This confers upon the drug or molecule contained within the cholestosome a longer residence time in the body, normally an advantage of a drug delivery system, but not necessarily an advantage if the molecule cannot be released from the drug delivery nanoparticle.

The evidence for this is the Zeta potential measurements showing cholestosomes with a neutral surface in one formulation cholestosomes have a measured Zeta potential of −14, which is typical of a neutral charge to cholestosomes alone in their unloaded form. Neutral charge boundaries for Zeta potential means having a Zeta potential of about −20 to about +20, often about −40 to +10, −5 to +5 or approximately 0. The push for neutral surface charge leads to the use of PEG is used in other types of formulations. Cholestosomes approximate the neutral surfaces of PEG in certain comparisons of embodiments among the various inventions.

Structural modifications of cholestosomes are based on modification of mole ratios of the esters which result in different interior and exterior surface properties and in cholestosomes those properties are not defined by an organization based on hydrophilic/hydrophobic sequestration (as in liposomes and other prior art delivery means) and therefore are more easily defined and manufactured, (Evidence of size as a result of sonication, often temperature, often pH (aqueous solutions of neutral pH have different charges on the molecules for encapsulation which may affect their ability to define the size of the lipid nanoparticles)). All of these beneficial properties are summarized and compared with those of other delivery systems in FIG. 30.

As shown in FIG. 30, a comparison of properties between Cholestosomes and alternative delivery modalities evidences that cholestosomes are superior or at least equal in all categories. One particularly important aspect of this comparison is that nearly any molecule can be encapsulated into a cholestosome without altering the molecule itself. This feature is not shared with other delivery systems, which tend to be specific to the molecule itself. Design flexibility is an advantageous property for a drug delivery system, clearly evident in the present invention.

As shown in FIG. 30, synthetic polymers refers generally to techniques such as PEGylation. Carrier proteins refers to attached biological molecules such as viral vectors. Both PEGylation and Carrier proteins constructs are given intravenously, and like liposomes, are not absorbed if given orally, primarily because they are degraded in the GI tract Loading Properties of Cholestosomes vs Liposomes Liposomes rarely load even 1% weight:weight even when using a lipophilic molecule such as doxorubicin. Cholestosomes as developed by the inventors often will load at least 20% and theoretically much higher, weight:weight as otherwise described herein.

Liposomes do not Load Proteins but Cholestosomes Load them Preferentially

Liposomes do not load proteins, genetic materials (polynucleotides, such as DNA and/or RNA as otherwise described herein), peptides (especially including polypeptides such as monoclonal antibodies) and many macromolecules including macromolecular antibiotics in usable amounts (less than 2% means that the amount of carrier is very large if encapsulating a dose of 100-1000 mg Which is typical of peptides or monoclonal antibodies). Many molecules which are water soluble, and where the charge is positive, are not favorably loaded into nanoparticles like phospholipid based liposomes. In contrast, the inside of a cholestosome (core) is large in relation to the size of the encapsulating membrane, and hydrophilic but neutral, a system compatible with loading proteins, peptides, genes as well as hydrophilic small molecules which are charged. Since all of these fail to pass the GI tract barrier, the use of Cholestosomes offer, for the first time, the prospect of orally absorbed proteins and peptides.

Neutral Charge of Cholestosomes Vs Positive Charge of Liposomes

Liposomes are not able to pass the Caco-2 enterocyte barrier intact, in fact most are broken open in the Eli tract to harvest their individual component phospholipids. Thus liposomes and their payloads are not taken up by enterocytes, perhaps due to their surface charge. Cholestosomes are comprised of Cholesteryl esters, which are already converted by cholesterol esterases into absorbable moieties. They are already neutral particles by virtue of their composition from cholesteryl esters, and are preferred in this form by the enterocyte cells of the duodenum for absorption intact and use in chylomicron formation. As long as the encapsulated molecule is completely within the hollow center, cholestosomes are taken up intact and they are placed intact into chylomicrons in the golgi apparatus of enterocytes.

Liposomes do not Pass Cell Membranes

Not only do liposomes fail to be orally absorbed with their payloads, they also do not enter cells and certainly when lacking APO on their surfaces, they have no ability to dock with cells in need of lipids. When injected intravenously, Liposomes are harvested by the liver and there broken down into their component phospholipids. This does not ordinarily offer intracellular delivery of their contents, although high local concentrations of payload molecules in the liver may offer an advantage if the target cell is the hepatocyte.

Liposomes and Therefore their Contents do not Enter Chylomicrons

Phospholipid coatings of liposomes are degraded in the GI tract, and thus the liposome itself has been degraded and its contents released in the GI tract, and even before arrival at the duodenal site of absorption. Thus even if a protein could be loaded into a liposome, it would be destroyed with the liposome before it could be absorbed by enterocytes. There is no chance for a phospholipid constituent liposome to be incorporated into a chylomicron.

Cholestosomes do not Enter Cells on their Own

Intravenously administered, cholestosomes would not dock with cells, as they are lacking the surface apolipoproteins which are necessary for docking with the cells. However, cell membranes do appear to trap cholestosomes, and from this vantage point the parenteral use of cholestosomes does allow some intracellular uptake of certain molecules. Intracellular uptake is much greater if these same cholestosomes are given orally. Topical administration, including vaginal administration is also preferred.

Cholestosomes clearly enable greater amounts cell uptake after oral absorption because they are first taken into chylomicrons. Chylomicrons then selectively deliver lipids to cells which are in need thereof. Cells in need express a docking site protein which then can link to the APO-B on the surface of the chylomicron, thus effecting docking and release from the chylomicron into the cytoplasm of the cell Furthermore the chylomicrons that are formed from cholestosomes have Apolipoprotein recognition properties on the surface that reaches every cell. As chylomicrons contact cells, they dock with cells that are expressing surface proteins and thereby requesting transport of lipids including triglycerides and cholesteryl esters. After lipases are disgorged from the cell, said lipids such as triglycerides and the cholestosomes are taken into the cell including their encapsulated payloads.

By Contrast, when liposomes are injected into the blood they would not be expected to dock with cells, as they are lacking Apo E constituents for docking with cells seeking lipids. Liposomes serve to create a prolonged plasma release characteristic to molecules in drug delivery. Furthermore, in the favorable occasion where the drug encapsulated within a liposome delayed release system does enter the cell, then it would be expected that there is intracellular delivery of payload because of the property of the drug after it is freed from the carrying liposome.

Formulation of Cargo-Loaded Cholestosomes—One of Ordinary Skill in the Art can Readily Look at any Molecule and Predict which Cholesteryl Ester(s) should be Used to Form Cholestosomes Cholestosomes are formed in several stages, first by dissolution of the pair of chosen cholesteryl esters in organic solvent such as ether, then removal of the organic solvent, and next there is addition of aqueous component which contains the molecule to be encapsulated, with sonication to form the unilamellar membranes and generate the hydrophilic relatively uncharged hollow pocket around molecules in aqueous.

All formation stages are carried out in a water bath at a critical specified temperature which is based on the lowest melt temperature of the esters. Working temperature is a primary condition for selection of cholesteryl ester pairs, as the melt temperature of the chosen pairs of esters must be equal to or lower than the temperature that will degrade the molecule chosen for encapsulation. With the temperature limits in mind, the cholesteryl ester pairs must be chosen to form a bilayer membrane at temperatures below 40 C, which is a basis for choice of cholesteryl myristate and cholesteryl laurate for many of the examples of encapsulated monoclonal antibodies in this disclosed invention.

Figure 2:
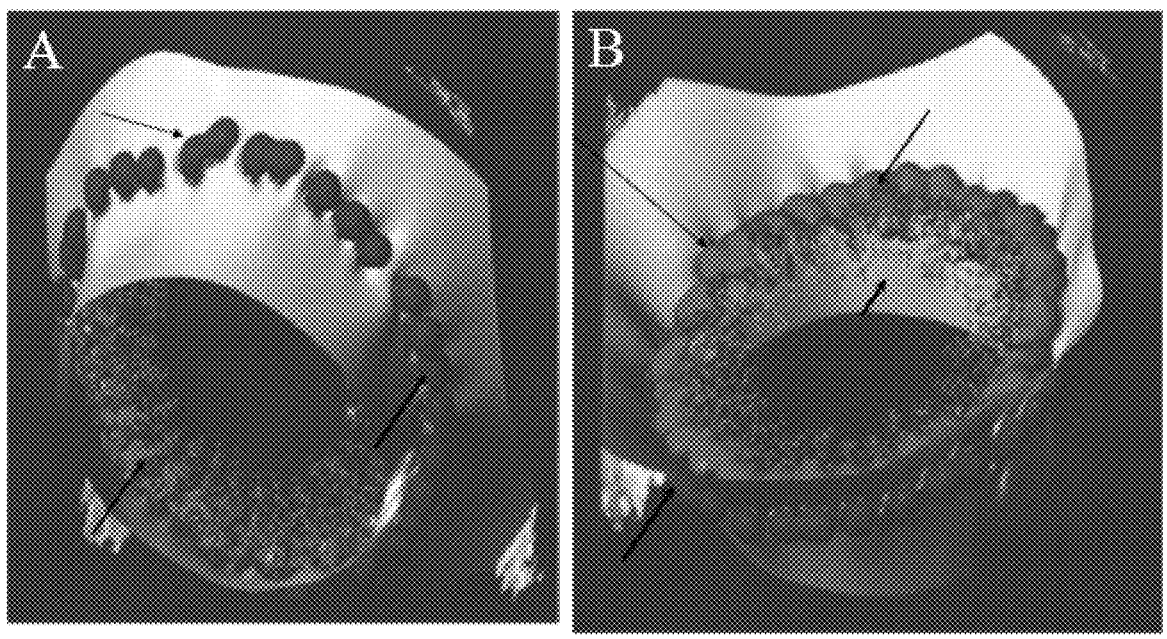
FIG. 2 shows a 3D Model of cholesteryl laurate/cholesteryl myristate in a 1:1 molar concentration ratio. A) bottom view slice B) top view slice. Red indicates negative charge (thin white arrows), blue indicates positive charge (thick white arrow) and the yellow surface shows the transition from one charged region to another (black arrows). The white arrowhead in B indicates the predicted positions of the esterified fatty acid moieties. Notice that in these cutaway views, the surface can be seen as a region where docking could occur and depending on the nature of the esterified lipid, the cavity could have multiple separate sites for binding molecules.
Figure 3:
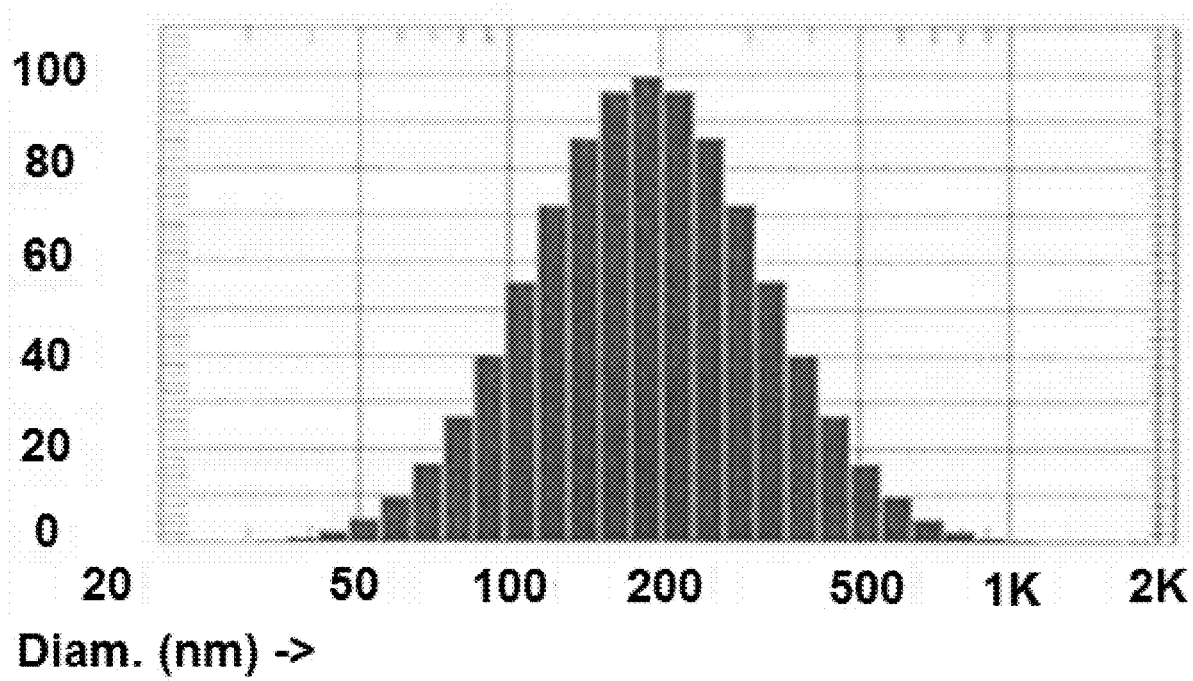
FIG. 3 shows Gaussian distribution of cholestosome size in a preparation of not yet loaded cholestosomes, as measured using DLLS. The cholestosomes in this preparation were 217+/−116 nm in diameter. Size ranged from approximately 50 nm to approximately 500 nm. Scale is 1000 nm which equals one micron
Figure 4:
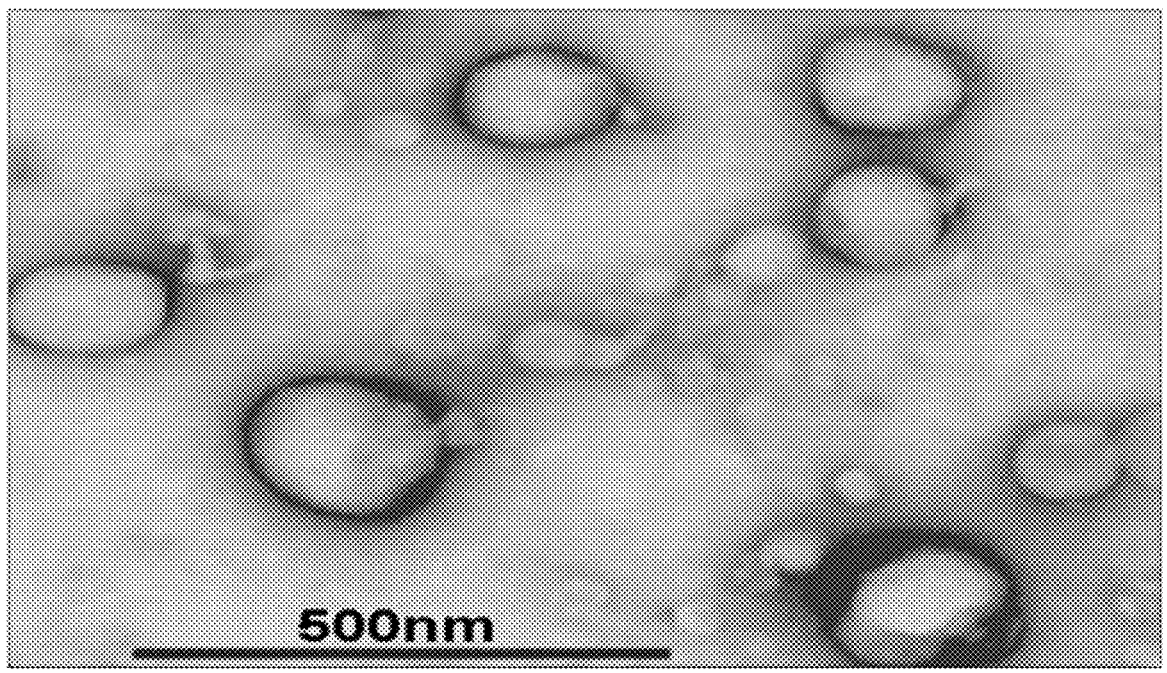
FIG. 4 shows sizing of cholestosomes during viewing of images from transmission electron microscopy. Cholestosomes were negatively stained using ammonium molybdate and imaged on a. Hitachi H-500 transmission electron microscope. A scale bar is shown for estimation of size. Scale units of 1000 nm equals one micron equals one micrometer equals one millionth of a meter. The median size range observed for cholestosomes in this microscopy, approximately 250 nm, is consistent with the size distribution determined by DLLS

FIG. 2 depicts a three dimensional model of a cholesteryl laurate/cholesteryl myristate (1:1 molar concentration) cholestosome. Cholestosomes can have a wide range of sizes, as shown in FIGS. 3 and 4. Active ingredient load can be determined through calculations such as those shown in the legends of FIGS. 15 and 16.

Once there is the addition of the aqueous molecule or construct, the mixture is sonicated until there is a cloudy solution formed, thereby minimizing waste from un-dissolved esters, with sonication providing energy for unilamellar vesicle formation. The aqueous component is also maintained at the target temperature prior to its addition, and as stated previously for most peptides, proteins and genes, the highest temperature that can be tolerated is only about 40° C.

The solution is then filtered and the filtrate is saved for extrusion for size conformity. The sample is then stored in the refrigerator.

The newly encapsulated molecule is surrounded by the unilamellar cholesteryl ester vesicle and inside the hollow pocket the encapsulated molecule is protected from contact with the harsh environment of the GI tract and is held away from enzymes and the cells of the immune system. The molecule inside remains unchanged. Accordingly, providing cargo-loaded cholostosomes pursuant to the present invention is a facile, routine undertaking.

Cholesteryl Ester Chain Length

The outer membrane of Cholestosomes consists of cholesteryl esters arranged to form a lipid nanoparticle based upon cholesteryl esters, generally in the case where the plurality of cholesteryl esters have the same or similar molecular length, so as to form a uniform capsule around a macromolecule encapsulated by said cholestosome. The cholesteryl esters may be of different lengths as long as they are co-soluble, which will permit them to aggregate together to form a vesicle with a rather large hollow core in relation to the total size of the lipid nanoparticle. In fact, some configurations have the core displacement well beyond 80 percent of the entire nanoparticle, which affords beneficial high loading of water soluble molecules such as insulin.

This is based on the ability of differential mole fractions of different esters being able to co-exist and aggregate in a minimum energy conformation in which the vesicle formation is determined by the nature of the cholesteryl esters and their relative mole fractions.

Figure 29:
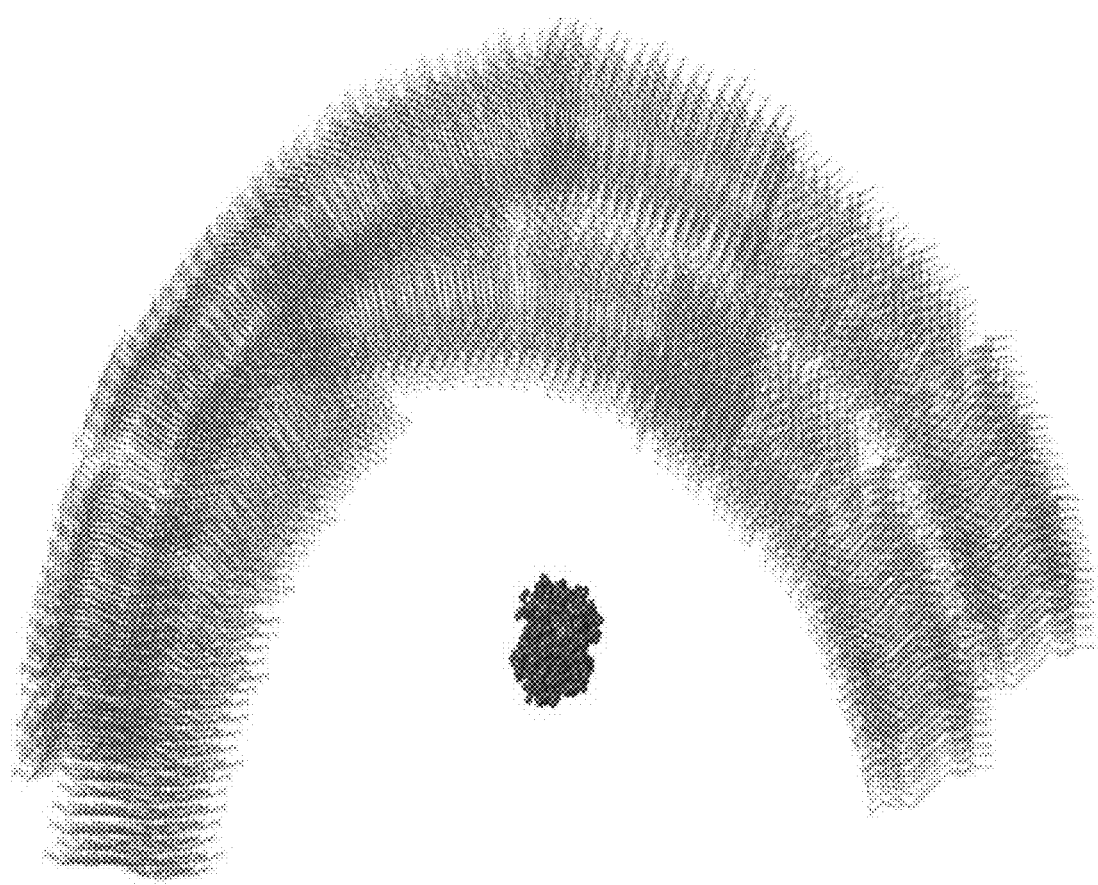

An illustration of an assembling nanoparticle around a molecule, in this case insulin is found in FIG. 29. Here, the chains are configured in a circular format so as to form a hollow center which has a neutral or mildly negative charge (Zeta potential measurements are made to define this property, as will be shown in the examples for each formulation disclosed. Cholestosomes alone have a Zeta Potential reading of −14).

With Insulin in the cholestosome, its Zeta Potential goes additionally negative. Cholestosome encapsulated formulations do not have highly positive charges, in contrast to Liposomes, where the Zeta potential could range as high as +76 in some experiments.

In this and other examples, the cholesteryl esters may be of different lengths as long as they are co-soluble, which will permit them to aggregate together to form a unilamellar vesicle. This is based on the ability of differential mole fractions of different esters being able to co-exist and aggregate in a minimum energy conformation in which the hollow core of the nanoparticle is determined by the nature of the cholesteryl esters and their relative mole fractions.

As the assembly of cholestosomes are considered and with reference to the 3D diagram as FIG. 2, consider first the assumption that the interior and exterior of the cholestosome matrix are the same structurally in that the sterol nuceli point both into the cavity and out to the surface.

What can be changed by choice of cholesteryl esters is the length of the ester tails. Having a shorter tail length brings the sterol nuclei closer to each other and lessens the hydrophobic nature of the vesicle (due to chain length). This may have an enhancing impact on the hydrophilic character of the cholestosome. This can be modeled and examples are presented in FIGS. 6 and 7.

Furthermore, assuming the same packing of the inner core of the lipid nanoparticle irrespective of chain length, shorter chains around a larger molecule would increase the mass to mass ratio of the molecule to the lipid. Clearly, larger molecules need larger internal cores, and hence ester chain length is important for the construction of larger cholestosomes to accommodate larger molecules such as monoclonal antibodies.

Balanced against these considerations is the impact of ester chain length on the relative hydrophilicity of the inner core. Longer ester chains increase the hydrophobic character and allow for packing of a more hydrophobic molecules into the core.

There is also the issue of interactions of matrix cholesteryl esters interacting with solvents. Aqueous solvent combinations including ethanol may help in the encapsulation process overall, and increase the amount encapsulated at a fixed ratio of cholesteryl esters. This is the impact of charge of the construct and charge of the inner core of the cholestosome.

For example, in crystal structures of oxysterols, changing the solvent ratio by including an alcohol such as ethanol helps bring the oxygen molecules closer to each other, which may help the esters orient in a cholestosome and also help bring the molecules into the core of the cholestosome vesicle more readily.

In modeling of these interactions, the inventors can examine models of cholesteryl ester matrix structures and predict which esters are the best choices for specific molecules or drugs. A systematic approach is possible when the interactions between esters, charge, solvents and molecule are considered simultaneously.

Effect of Particle Size on Target

Cholestosome component mixtures differ in novel ways depending on the ionic and physicochemical characteristics of the macromolecular component. The size of the cargo-loaded cholestosome often affects the target in that certain cholesterol esters, when formed into cholestosomes, are better suited for delivering certain molecules and thus the impact of ester chain length, How the Charge and Molecular Pattern Impact the Size of the Cholestosome Larger molecules with greater net positive charges need longer chain length cholesteryl esters for optimal encapsulation, provided the melt temperature is compatible with the stability of the molecule being encapsulated, throughout the encapsulation process. Smaller molecules with a lower net positive charge may be encapsulated with shorter chain length cholesteryl esters. Adjustment of the cholesteryl ester chain length to provide lipid nanoparticles based upon cholesteryl esters pursuant to the present invention is well within routine skill.

Surfaces on said cholestosomes may either be smooth, or rough, dependent on component balance and mixture characteristics. The character of the vesicle surface will depend on the esters themselves as well as the interaction of the esters with each other. The expectation is that the esters will aggregate to optimize the molecular interactions and to minimize the holes or spaces between them. These arrangements may therefore produce a surface that is rough.

Most of the graphical examples in the figures of this disclosure have rough configuration, as the esters have arranged themselves so that structural components are interdigitated on the vesicle surface to produce an uneven structural arrangement (rough). In some cases the esters have arranged themselves so that they are aligned to produce a surface of constant shape and size (smooth).

The nature of the final surface configuration will depend on the combinations of esters used and their relative concentration in the formulation. In summary, both the choice of esters and the choice of molecule affect the final arrangement of the lipid nanoparticle. While the various components affect the surface configurations, a novel surface property, the neutral surface itself that allows for uptake by enterocytes, should be the net effect of the charges of the chosen molecules in the final formulation. The surface should always be neutral Properties of Formed Cholestosomes and Illustrated Examples Larger molecules with greater net positive charges need longer chain length cholesterol esters for optimal encapsulation.

Preferred cholesteryl esters for use with larger water soluble macromolecules such as proteins and peptides are those which are prepared by the esterification (or a related process to provide the corresponding cholesteryl ester) of a $C_8$ to $C_{26}$ saturated or unsaturated fatty acid, often a fatty acid selected from the group consisting of Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, Cerotic acid or a mixture thereof.

The mixing of more than one (preferably two) cholesteryl ester to form cholestosomes may accommodate different sized active molecules with varying delivery characteristics.

FIG. 2 depicts a three dimensional model of a cholesteryl laurate/cholesteryl myristate (1:1 molar concentration) cholestosome. Cholestosomes can have a wide range of sizes, as shown in FIGS. 3 and 4. Active ingredient load can be determined through calculations such as those shown in the legends of FIGS. 15 and 16.

A discussion of the prior art delivery methods that have been attempted without success for proteins and peptides has been presented, allowing the skilled practitioner to understand that prior delivery methods do not possess most of the critical embodiments necessary for successful oral use of proteins in human patients. From this disclosure also, it is clear to those skilled in the art how Cholestosomes solve each and all of these prior deficiencies with respect to oral absorption and subsequent delivery to body cells after incorporation into chylomicrons.

Figure 5:
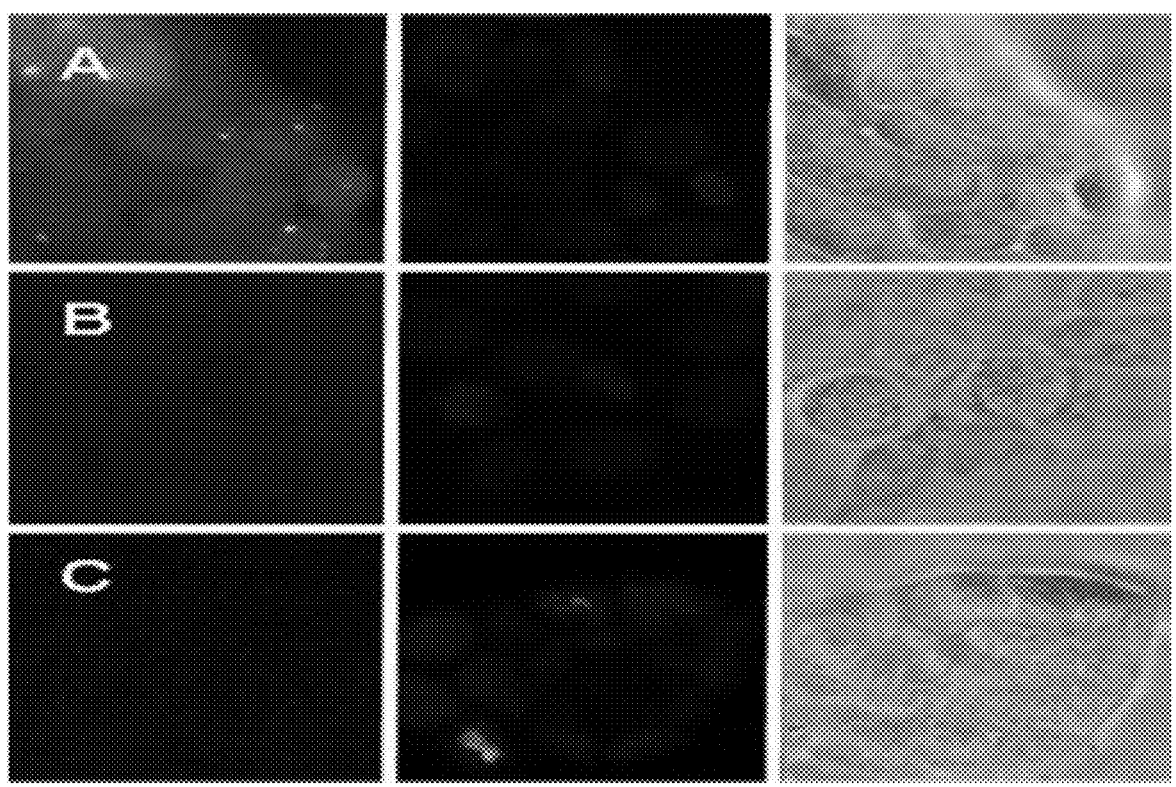
FIG. 5 shows cholestosome-mediated delivery of FITC into MCF7 cells, measured after 24 hr of incubation. (A) Addition of FITC encapsulating cholestosomes (ChF). (B) Addition of free FITC solution (FITC, 0.5M). (C) Addition of 100 uL of distilled water. Cells were incubated overnight with ChF, FITC (100 uL) or vehicle (water) in complete medium. Cells were washed twice with medium and then incubated for 15 minute with 10 uM Hoechst 33342 to stain nuclei. The later proves cell viability. Note the homogenous fluorescence in ChF treated cells (left panel in A), which indicates even distribution in cytoplasm.

For example, FIG. 5 depicts cholestosome-mediated delivery of FITC into MCF7 cancer cells, evidencing the invention's ability to deliver active ingredients to therapeutic sites that necessitate precise active ingredient targeting. Subsequent examples with show more cholestosome preparations that pass cell membranes in the manner of FIG. 5, but in fact when cholestosomes are absorbed into enterocytes and then passed intact into chylomicrons, the delivery inside cells is much greater. These examples illustrating greater intracellular penetration will also be shown.

Specific Commercial Opportunities for Individual Molecules—

It is well known that prior disclosed delivery methods, and compositions involving lipids in formulation do not pass the enterocytes of the gastrointestinal tract, are not incorporated into chylomicrons, and do not pass the membrane of most cells.

The advanced capabilities conferred by cholestosome encapsulation are surprising in view of the composite prior art. Put simply, no delivery system has functioned favorably at the task of oral delivery of large hydrophilic molecules (especially macromolecules such as polypeptides (especially including monoclonal and polyclonal antibodies), proteins and polynucleotides, especially RNA, including small interfering RNA, small hairpin RNA, microRNA, and DNA, especially including plasmid DNA and naked DNA.

Among these molecules, there are preferred candidates by virtue of the need for chronic use in disease treatment simply because now they must be injected and subsequently after formulation into cholestosomes they may be given by mouth, or applied to skin as an ointment or cream, or inhaled as a lipid nanoparticle. These will be disclosed.

Two Step Cholestosome Facilitated Delivery of Macromolecules into Cells.

In the Instant invention, as illustrated in FIG. 1, a macromolecule such as insulin may be delivered inside body cells after two sequential steps in formulation and bioprocessing. In the first step, we prepare a cholestosome and encapsulate said macromolecule in the formed cholestosome, in full recognition that the cholestosome must be comprised of specific cholesteryl esters selected for compatibility with each chosen molecule. The cholesteryl ester constituents of the cholestosome must also be selected to ensure that there is a transporter on the surface of duodenal enterocytes. The second step in preparation of the macromolecular delivery system occurs when the duodenal enterocytes incorporate the cholestosome-macromolecule construct into chylomicrons and secrete these now loaded and newly transformed chylomicrons into lymphatic fluids which carry the chylomicrons to the thoracic duct and eventually circulate in blood of said patient.

Docking Because of APO-B Incorporation into Chylomicrons

Intracellular delivery of macromolecules encapsulated within cholestosomes and incorporated within chylomicrons is accomplished when the chylomicrons containing the cargo-loaded cholestosome containing an active molecule payload dock with cells in need of cholesterol and triglycerides and transfer said components including said cholestosomes into cells without requiring endosome encapsulation. A further novelty of the present method is release of cholestosome incorporated macromolecules into cytoplasm of cells in intact form as exterior surface cholesteryl esters are removed in cytoplasm and thereby release the molecule from its cholestosome delivery capsule. As long as the surface of the cholestosome is then recognized as a needed cholesteryl ester by the target cell, the target cell will receive the payload and after unpacking the surface by cholesteryl ester hydrolases the macromolecule will be freed inside the membrane of the target body cell.

Figure 22:
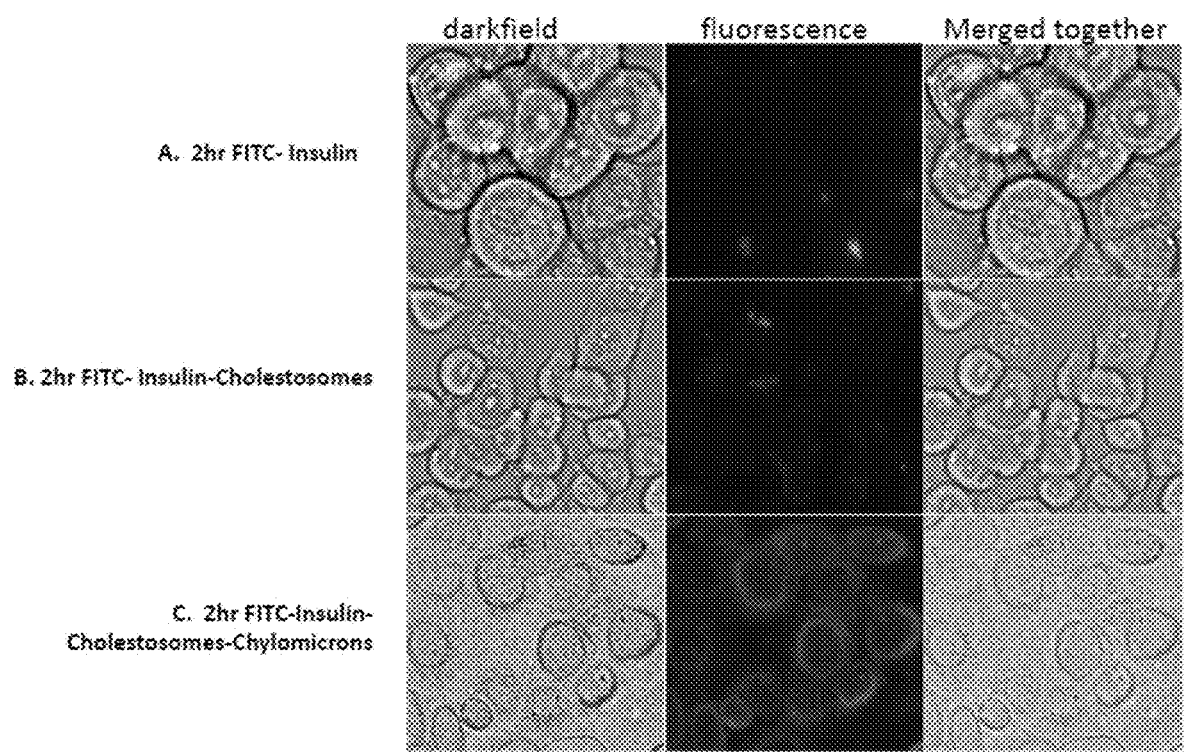

As can be appreciated from the images of MCF-7 cells in FIG. 22, there is nearly always some uptake of molecules from cholestosomes alone, as shown with cholestosome encapsulated FITC (the control) in FIG. 5. However, there is an unexpectedly large (at least 1000× greater) differential uptake by MCF-7 cells when FITC cholestosomes are first exposed to Caco-2 cells and the resulting FITC-cholestosome-chylomicrons are collected from the basolateral side of the apparatus (as in FIG. 17), then used for exposure to MCF-7 cells. It should be noted that these FITC-insulin-cholestosome chylomicrons were prepared using the FITC-insulin-cholestosomes in the same amount on the Caco-2 cells, so essentially all the FITC-insulin-cholestosomes were incorporated by the Caco-2 cells into FITC insulin chylomicrons.

Loading of Cholestosomes into Chylomicrons

Loading of cholestosomes and their molecular payload into chylomicrons by the golgi apparatus appears to be quantitative, as evidenced by re-measurement of the apical side of the Caco-2 and subtraction of the amount remaining from the amount recovered in chylomicrons on the basolateral side. Thus, the affinity of Caco-2 cells for cholestosomes appears to be very high. The Caco-2 cells clear all of the available cholestosomes placed on the apical side into chylomicrons oar the basolateral side. Thus, the early choice of cholesteryl esters to be used to encapsulate the active molecule(s) is an essential step in the practice of the invention.

Protection of Molecular Payloads from Add and/or Enzymatic Degradation in the GI Tract.

Cholestosomes survive intact at pH values ranging from 2-14, in contrast to liposomes which are rapidly degraded by these same conditions and are relatively unstable compared to compositions according to the present invention. Cholestosomes prepared with labile payloads may be coated with an outer enterically targeted layer in cases where their payload constituents must be protected from degradation in the gastrointestinal tract so that the cargo-loaded cholestosomes reach the duodenum (G.I. sites of enterocytes which produce chylomicrons incorporating the cholestosomes).

Payloads such as insulin and other proteins/polypeptides are acid labile, necessitating an additional step of an enteric coating protective of insulin in cholestosomes, to be applied prior to use in animal or in vivo systems where there is potential for acid or enzymatic degradation. Under usual situations in the practice of the art, when the contents of a cholestosome are acid labile peptides and proteins, and when these products are cholestosome encapsulated in preparation for oral ingestion, there should be a final product administered with an enteric coating to protect the contents of the cholestosomes from the acid in the stomach. In most cases after release of the cholestosomes in the duodenum there is the possibility of enzymatic degradation or bile salt mediated saponification in the duodenum, so there is a need to perform stability studies of the individual cholestosomes in contact with bile salts, pancreatic lipases and pancreatic esterases. Therefore unless or until the protein or peptide is definitively proven to be free of acid degradation, the dosage form will be a small capsule filled with cholestosome construct, then coated with enteric coating to release contents at pH 5.5 to 6.0. A suitable coating for this purpose would be Eudragit (64, 65) or another enteric polymer which is stable to acid but having similar degradation characteristics to the Eudragi polymers and while cholestosomes themselves are stable in low pH, there remains a need to employ enteric coatings known in the art to protect the contents of cholestosomes from acid degradation.

In certain embodiments, the pharmaceutical composition is a unilamellar vesicle having a diameter of about 100 to about 750 nm, preferably about 225 to about 275 nm, and even more preferably around 250 am, DLLS measurements indicate vesicles with diameters ranging from 50 nm to more than 1000 nm. The final size used can be made from selective extrusion with an appropriate pore size as well as control of time of sonication as well as other preparation parameters.

"Immunomicelles" and "micelles" are aggregates formed by amphipathic molecules in water or an aqueous solvent such that their polar ends or portions are in contact with the water or aqueous solvent and their nonpolar ends or portions are in the interior of the aggregate. A micelle can take any shape or form, including but not limited to, a non-lamellar "detergent-like" aggregate that does not enclose a portion of the water or aqueous solvent, or a unilamellar or multilamellar "vesicle-like" aggregate that encloses a portion of the water or aqueous solvent, such as, for example, a liposome. Specifically included within the definition of "micelle" are small unilamellar vesicles or liposomes ("SUVs"), small multilamellar vesicles or liposomes ("SMVs"), large unilamellar vesicles or liposomes ("LUVs") and large multilamellar vesicles or liposomes ("LMVs").

As defined in United States Patent Application Document No. 20110268653 "'lipidic particle' refers to a particle having a membrane structure in which amphipathic lipid molecules are arranged with their polar groups oriented to an aqueous phase. Examples of the lipid membrane structure include configurations such as a liposome, multi lamellar vesicle (MLV), and a micelle structure. A 'Liposome' refers to a closed nanosphere, which is formed by forming a bilayer membrane of a phospholipid molecule with the hydrophobic moiety positioned inside and the hydrophilic moiety positioned outside, in water and closing the ends of the bilayer membrane Examples of liposomes include a nanosphere having a single layer formed of a phospholipid bilayer membrane and a nanosphere having a multiple layer formed of a plurality of phospholipid bilayers. Since a liposome has such a structure, an aqueous solution is present both inside and outside of the liposome and the lipid bilayer serves as the boundary. A 'micelle' refers to an aggregate of amphipathic molecules. The micelle has a form in which a lipophilic moiety of this amphipathic molecules is positioned toward the center of the micelle and a hydrophilic moiety is positioned toward the outside thereof, in an aqueous medium. A center of a sphere is lipophilic and a peripheral portion is hydrophilic in such a micelle. Examples of a micelle structure include spherical, laminar, columnar, ellipsoidal, microsomal and lamellar structures, and a liquid crystal." Note that such structures do a very poor job of encapsulating hydrophilic molecules like peptides and proteins, where loading is 1:1000 or worse. Contrast that with cholestosomes with hydrophilic centers (from the orientation of the ester functionality) and hydrophobic outsides. In certain embodiments, the interior and exterior may be the same with the sterol nucleus on the outside surface and inside cavity with the tails of the esters interdigitated in a Pseudo-bilayer type of molecule. When a chylomicron takes up a cholestosome, the truly hydrophilic outside is re-established by the Apolipoprotein components of the transformed and loaded chylomicrons, and the Apolipoproteins also facilitate docking of the transformed chylomicrons with cells. In short, the cholestosome two stage formation into a chylomicron is totally novel and unexpected compared to previous efforts.

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "compound" is used herein to refer to any specific chemical compound or disclosed herein. Within its use in context, the term generally refers to a single small molecule as disclosed herein, but in certain instances may also refer to stereoisomers and/or optical isomers (including racemic mixtures) of disclosed compounds. The term compound includes active metabolites of compounds and/or pharmaceutically active salts thereof.

The term "active molecule", "active agent" or "active compound" shall mean any molecule which is active in a biological system and which may be incorporated into a cholestosome as described herein. Cholestomes according to the present invention are able to readily accommodate a large number of active compounds, including small molecules and large molecules, especially including compounds which cannot otherwise be delivered efficiently orally. This is because of the unique mechanism (as described herein) that cargo-loaded cholestosomes provide in delivering active compounds through enterocytes into chylomicrons and then into the cells of a patient or subject to whom these cargo-loaded cholestosomes are administered. These active molecules include small molecules which are unstable to standard oral delivery techniques and are typically only parenterally administered and macromolecules such as proteins (including glycoproteins) and polypeptides (e.g insulin, interferon, hCG, C-reactive protein, cytokines, including various interleukins, growth factors), other polypeptides, including antibodies such as polyclonal antibodies, monoclonal antibodies (as otherwise described in detail herein, antibody fragments (single chain variable fragments or scFv, antigen-binding fragments or Fab, $_3$G antibodies), immunogenic polypeptides and oligopeptides, polynucleotides, including DNA and RNA, such as naked DNA, plasma DNA, mRNA, siRNA, shRNA, bifunctional shRNA, microRNA (including miR-122, among others) and various oligonucleotides of DNA and RNA. Numerous anti-infective agents, including antibiotics (such as vancomycin and penicillin) and antiviral agents and other active molecules, especially including macromolecular antibiotics as well as numerous anticancer agents which are disclosed in detail herein, may also be delivered by the present invention. It is noted that cholestosomes pursuant to the present invention may be used to deliver virtually any active molecule of a wide variety of sizes and molecular weight. Cholestosomes according to the present invention may also be used to topically deliver a number of active molecules to provide high bioavailability through the skin of a patient or subject including topical antibiotics, topical anti-fungals, topical platelet derived growth factor, other growth factors, topical anti-TNF for psoriasis, for example and topical vaccines, and topical deliver of cosmetic agents, among others. Numerous chemotherapeutic agents, antibiotics, and antiviral agents may be incorporated into cholestosomes according to the present invention. The cholestosomes according to the present invention are particularly suited for these compounds, even small molecules, because delivery of the compound into the cell pursuant to the mechanism of active molecule delivery by compositions according to the present invention represents a particularly effective therapy against a variety of microbes, including bacteria and viruses.

Antifungals for use in the present invention include, for example, miconazole, terconazole, econazole, isoconazole, tioconazole, bifonazole, clotrimazole, ketoconazole, butaconazole, itraconazole, oxiconazole, fenticonazole, nystain, naftifine, amphotericin B, zinoconazole, ciclopiroxolamine or a mixture thereof Antibiotics for use in the present invention include Aminoglycosides, including Gentamicin Garamycin Kanamycin, Neomycin, Netilmicin, Tobramycin, Paromomycin, Spectinomycin; Ansamycins, including Geldanamycin, Herbimycin Rifaximin and Streptomycin; Carbapenems, including Ertapenem Doripenem Imipenem/Cilastatin and Meropenem; Cephalosporins, including Cefadroxil Cefazolin Cefalotin/Cefalothin, Cefalexin Cefactor, Cefamandole, Cefoxitin, Cefprozil, Cefuroxime, Cefixime Cefdinir, Cefditoren, Cefoperazone Cefotaxime Cefpodoxime, Ceftazadime, Ceftibuten Ceftizoxime Ceftriaxone, Cefipime, Ceftaroline fosamil and Ceftobiprole; Glycopeptides, including Teicoplanin, Vancomycin and Telavancin; Lincosamides, including Clindamycin and Lincomycin; Lipopeptipdes, including Daptomycin, Oritavancin, WAP-8294A; Macrolides, including Azithromycin, Clarithromycin, Dirithromycin, Erythromycin, Roxithromycin, Telithromycin and Spiramycin;

Monobactams, including Aztreonam; Nitrofurans, including Furazolidone and Nitrofurantoin; Oxazolidonones, including Linezolid, Posizolid, Radezolid and Torezolid; Penicillins, including Amoxicillin, Ampicillin Azlocillin, Carbenacillin, Cloxacillin Dicloxacillin, Flucloxacillin, Mezlocillin, Methicillin, Nafcillin, Oxacillin, Penicillin G, Penicillin V. Piperacillin, Temocillin and Ticarcillin; Penicillin combinations including Amoxicillin/clavulanate, Ampicillin/sulbactam, Piperacillin/tazobactam and Ticarcillin/clavulanate; Polypeptides, including Bacitracin, Colistin and Polymyxin B; Quinolones/fluoroquinolines, including Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin;

Sulfonamides, including Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole and Sulfonamidochrysoidine; Tetracyclines, including Demeclocycline, Doxycycline, Vibramycin Minocycline, Oxytetracycline and Tetracycline; Anti-mycobacterial, including Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole and Trimethoprim.

Antiviral agents include anti-HIV agents, anti-HBV agents and anti-HCV agents Which are known in the art. Anti-HIV agents include 3TC (Lamivudine), AZT (Zidovudine), (-)-FTC, ddI (Didanosine), ddC (zalcitabine), abacavir (ABC), tenofovir (PMPA), D-D4FC (Reverset), D4T (Stavudine), Racivir, L-FddC, L-FD4C (Elyucitabine), Festinavir, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIS' agents Which may be used in the present invention include, various NNRTI's selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151), U-104489 or PNU-104489), Capravirine, atevirdine Calanolide A (NSC675451), Calanolide B and Foscarnet (Foscavir), among others.

Anti-HBV agents which may be formulated in cholestosomes according to the present invention include Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 109, EHT899, zadaxin (thymosin alpha-1) and mixtures thereof.

Anti-HCV agents which may be formulated in cholestosomes according to the present invention include ribavirin, interferon, pegylated interferon, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GE 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCSY-635, TLR9 Agonist, PHX1766, SP-30 and mixtures thereof.

Other compounds for use in the present invention are also described herein below, in the examples which follow.

It is noted in the present invention that incorporation of active molecules into cholestosomes and administration to a patient or subject will produce a greater therapeutic effect at the same dosage level than identical active molecules delivered by prior art methods. In effect, the mechanism of packaging cargo-loaded cholestosomes in chylomicrons results in a substantial greater amount or concentration of an active molecule at its actual site of activity (in a cell) resulting in substantially greater efficacy than prior art methods. In many instances, the amount of concentration of active agent delivered inside a cell according to the present invention is at least 2 and often as much as 10 times to 1000 times the concentration of active compared to delivery by prior art (contemporary) means.

The term "effective amount" is used throughout the specification to describe concentrations or amounts of formulations or other components which are used in amounts, within the context of their use, to produce an intended effect according to the present invention. The formulations or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 50 mg/kg or more, about 0.5 mg/kg to about 25 mg/kg, about 0.1 to about 15 mg/kg, about ling to about 10 mg/kg per day and otherwise described herein. For avoidance of doubt, the dosage of the component in said formulation given to said animal is approximately the same as would be given by parenteral means, after correction for the added mass of the delivery system. The person of ordinary skill may easily recognize variations in dosage schedules or amounts to be made during the course of therapy.

The term "coadministration" is used to describe the administration of two or more active compounds, in this case a compound according to the present invention, in combination with an additional agent or other biologically active agent, in effective amounts. Although the term coadministration preferably includes the administration of two or more active compounds to the patient at the same time, it is not necessary that the compounds actually be administered at the exact same time or in the same composition (although that may be preferable), only that amounts of compound will be administered to a patient or subject such that effective concentrations are found in the blood, serum or plasma, or in the pulmonary tissue at the same time.

The term "Ileal brake hormone releasing agent" is used to describe a nutritional substance which modules hormones in the ileum. These nutritional substances include, but are not limited to proteins and associated amino acids, fats including saturated fats, monosaturated fats, polyunsaturated fats, essential fatty acids. Omega-3 and Omega-6 fatty acids, trans fatty acids, cholesterol, fat substitutes, carbohydrates such as dietary fiber (both soluble and insoluble fiber), starch, sugars (including monosaccharides monosaccharide, fructose, galactose, glucose, disaccharides, lactose, maltose, sucrose, and alcohol), polymeric sugars including inulin and polydextrose, natural sugar substitutes (including brazzein, Curculin, erythritol, fructose, glycyrrhizin, glycyrrhizin, glycerol, hydrogenated starch hydrosylates, isomalt, lactitol, mabinlin, maltitol, mannitol, miraculin, monellin, pentadin, sorbitol, stevia, tagatose, thaumatin, and xylitol), sahlep, and halwa root extract. D-glucose (dextrose) is a preferred nutritional substance. Nutritional substances include all compositions that yield the aforementioned nutrients upon digestion or that contain such nutrients, including polymeric forms of these nutrients. When these compositions are related in the ileum of a patient, ileal brake hormones are modulated often resulting in an increase in activity, thus providing a beneficial therapeutic effect on a number of disease states and conditions. The effects of ileal brake hormone releasing agents are discussed in great detail in US patent publication 2011-0268795, published Nov. 3, 2011 and international patent publications WO 2010/027498, published Mar. 10, 2010 and WO 2013/063527, published May 2, 2013 and may be referenced for the teachings which are incorporated therein. A preferred ileal brake hormone releasing agent is glucose administered in the ileum of a patient at a dose ranging from about 7.5 g to about 12 g or more.

The term "ileum hormones" includes all hormones that are associated with intraluminal food substances stimulating the release of said hormones, which may be caused by ileum-related stimulation of insulin secretion or inhibition of glucagon secretion or the delivery of a nutritional substance within the teachings of the art to the ileum of a patient or subject. "Ileum hormones" therefore include, but are not limited to, GLP-1, glicentin, C-terminally glycine-extended GLP-1 (7 37), (PG (78 108)); intervening peptide-2 (PG (111 122) amide); GLP-2 (PG (126 158), GRPP (PG (1 30)), oxyntomodulin (PG (33 69), and other peptide fractions to be isolated, PYY (PYY 1-36) and (PYY 3-36), cholecystokinin (CCK), gastrin, enteroglucagon and secretin.

The term "ileum hormone-stimulating amount of a nutritional substance" means any amount of a nutritional substance that is effective to induce measurable hormone release in the ileum, and induce satiety feedback from the ileum or ileum-related stimulation of insulin secretion or inhibition of glucagon secretion, or other effect such as shutting down or decreasing insulin resistance and increasing glucose tolerance. Consequently, an "ileum hormone-stimulating amount of a nutritional substance" can vary widely in dosage depending upon factors such as the specific nutrient at issue, the desired effect of administration, the desired goal of minimizing caloric intake, and the characteristics of the subject to whom the nutritional substance is administered. For example, at least about 500 mg of D-glucose is used, and a particularly preferred ileum hormonal-stimulating amount of D-glucose includes between about 7.5-8 g to about 12-12.5 or more (preferably around 10 g).

Additional nutritional components which may be included in compositions according to the present invention include, barley grass, known to be a rich source of highly metabolizable vitamins and minerals such as vitamins A, B1, B2, B6, and C, potassium, magnesium, and zinc. In addition, barley grass also has a high concentration of the enzyme superoxide dismutase (SOD), which has been shown to have high levels of antioxidant activity. Barley grass is believed to be an important nutrient in the regulation of the digestive process because the micronutrients, enzymes (e.g., SOD), and fiber contained in barley grass are believed to improve intestinal function.

Alfalfa fresh or dried leaf tea is also usable in the invention, to promote appetite, and as a good source of chlorophyll and fiber. Alfalfa contains biotin, calcium, choline, inositol, iron, magnesium. PABA, phosphorus, potassium, protein, sodium, sulfur, tryptophan (amino acid), and vitamins A, B complex, C, D, E, K, P, and U. Alfalfa supplements are recommended for treating poor digestion, and were shown to lower cholesterol levels in animal studies. Alfalfa is categorized as Generally Regarded as Safe (GRAS) by the FDA. Dosages can range from 25-1500 mg, preferably 500-1000 mg dried leaf per day.

*Chlorella* is yet another substance usable in the invention in combination with the nutritional substance (preferably D-glucose or dextrose), being a genus of unicellular green algae, grown and harvested in tanks, purified, processed and dried to form a powder. *Chlorella* is rich in chlorophyll, carotenes, and contains the full vitamin B complex, vitamins E and C, and has a wide range of minerals, including magnesium, potassium, iron and calcium. Morella also provides dietary fiber, nucleic acids, amino acids, enzymes, CGF (*Chlorella* Growth Factor) and other substances. Dosages can range from 300-1500 mg/day.

Chlorophyllin is yet another nutritional substance, being a known food additive and has been used as an alternative medicine. Chlorophyllin is a water-soluble, semi-synthetic sodium/copper derivative of chlorophyll, and the active ingredient in a number of internally-taken preparations intended to reduce odors associated with incontinence, colostomies and similar procedures, as well as body odor in general. It is also available as a topical preparation, purportedly useful for treatment and odor control of wounds, injuries, and other skin conditions, such as for radiation burns.

Sodium alginate may also be used as a nutritional substance, preferably in combination with D-glucose or dextrose.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or pro-drug form) of the present compounds or a carrier, additive or excipient which is not unacceptably toxic to the subject to which it is administered.

Inflammation Associated Metabolic Disorder

An "inflammation-associated metabolic disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia (e.g. hyperlipidemia (e.g., as expressed by obese subjects), elevated low-density lipoprotein (LDL), depressed high-density lipoprotein (HDL), and elevated triglycerides) and Hepatic (or liver) injury associated with insulin resistance and inflammation including Hepatic steatosis, Non alcoholic fatty liver diseases, cirrhosis, hepatitis caused by viruses such as Hepatitis A, B, or C, or toxins and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, atherosclerosis, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, Hepatitis C or B, wounds, skin disorders, gut structure and function that need restoration, and so forth.

An "inflammation-associated metabolic disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequelae of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, "inflammation-associated metabolic disorder" includes: central obesity, dyslipidemia including particularly hypertriglyceridemia, low HDL cholesterol, small dense LDL particles and postprandial lipemia; glucose intolerance such as impaired fasting glucose; insulin resistance and hypertension, and diabetes. The term "diabetes" is used to describe diabetes mellitus type I or type II. The present invention relates to a method for improving pancreatic function, hepatic function, brain function, gastrointestinal function, cardiovascular function, renal function and symptoms, conditions and disease states which occur secondary to impaired function in patients or subjects with diabetes as otherwise described herein. It is noted that in diabetes mellitus type I and II, renal function is impaired from collagen deposits, and not from cysts in the other disease states treated by the present invention.

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *Mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686. (1999); and 2000 WHO/OMS Press Release).

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

In many countries the only measure for TB control has been vaccination with *M. bovis* bacille Calmette-Guerin (BCG). The overall vaccine efficacy of BCG against TB, however, is about 50% with extreme variations ranging from 0% to 80% between different field trials. The widespread emergence of multiple drug-resistant *M. tuberculosis* strains is also a concern.

*M. tuberculosis* belongs to the group of intracellular bacteria that replicate within the phagosomal vacuoles of resting macrophages, thus protection against TB depends on T cell-mediated immunity. Several studies in mice and humans, however, have shown that Mycobacteria stimulate antigen-specific, major histocompatibility complex (MHC) class II- or class I-restricted CD4 and CD8 T cells, respectively. The important role of MHC class I-restricted CD8 T cells was convincingly demonstrated by the failure of β2-microglobulin) deficient mice to control experimental *M. tuberculosis* infection.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis*. Other mycobacterial species include *M. avium-intracellulare, M. kansarii, M. fortuitum, M. chelonae, M. leprae, M. africanum,* and *M. microti, M. avium paratuberculosis, M. intracellulare, M. scrofulaceum, M. xenopi, M. marinum, M, ulcerans*.

Infectious Disease

An "infectious disease" includes but is limited to those caused by bacterial, mycological, parasitic, and viral agents. Examples of such infectious agents include the following: *Staphylococcus*, streptococcaceae, neisseriaaceae, cocci, enterobacteriaceae, pseudomonadaceae, vibrionaceae, *Campylobacter*, pasteurellaceae, *Bordetella, Francisella, brucella*, legionellaceae, bacteroidaceae, gram-negative bacilli, *Clostridium, Corynebacterium, Propionibacterium*, gram-positive bacilli, *Anthrax, Actinomyces, Nocardia, Mycobacterium, Treponema, Borrelia, Leptospira, Mycoplasma, Ureaplasma, Rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses, among numerous others.

In certain embodiments, an "infectious disease" is selected from the group consisting of tuberculosis, leprosy, Crohn's Disease, acquired immunodeficiency syndrome, Lyme disease, cat-scratch disease, Rocky Mountain spotted fever and influenza.

Cancer

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascetic and solid tumors.

Components in Formulations of the Invention

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Tween was used in the present example; Tween may be used to improve the yield of emulsion prior to extrusion step; Tween can be added to the aqueous preparation prior to the addition to the lipids or to the lipid and then addition of aqueous. The smallest amount of tween possible is used, that being less than about 100 microliters in 10 ml of aqueous. Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMA- CEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally. When parenteral administration is contemplated, the therapeutic formulations for use in this invention may be in the form of a pyrogen-free, parenterally acceptable aqueous solution. Preparation involves the formulation of the desired immunomicelle, which may provide controlled or sustained release of the product which may then be delivered via a depot injection. Formulation with hyaluronic acid has the effect of promoting sustained duration in the circulation.

Formulations according to the present invention may be formulated for inhalation. In these embodiments, a stealth Cholestosome-molecule formulation is formulated as a dry powder for inhalation, or inhalation solutions may also be formulated with a propellant for aerosol delivery, such as by nebulization. Pulmonary administration is further described in PCT Application No. PCT/US94/001875, which describes the pulmonary delivery of chemically modified proteins and is hereby incorporated by reference.

Formulations may be formulated for topical application on the skin. In these embodiments, a stealth Cholestosome-molecule formulation is formulated as an ointment or cream, and applied to the surface of the skin.

Formulations of the invention can be delivered through the digestive tract, such as orally and this represents a preferred route of administration. The preparation of such pharmaceutically acceptable compositions is disclosed herein and within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Enteric coatings which are stable to acid but degradable within a pH of the duodenum (about 5.0 to about 6.0 or slightly higher) may be preferred. These are well known in the art. Additional agents can be included to facilitate absorption. Diluents, flavorings, low melting point waxes, vegetable oils, lubricants, suspending agents, tablet disintegrating agents, and binders may also be employed.

A formulation may involve an effective quantity of a cholestosome, most preferentially a cholestosome formulation and a molecule in a pharmaceutical composition as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierce-able by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted or topically applied into any suitable tissue or organ, and delivery of the desired molecule may be via diffusion, timed-release bolus, or continuous administration.

As used herein, "enteric coatings" are substantially insoluble at a pH of less than a range of between about 5.0 to 7.0 to about 7.6 (preferably about 5.0 to about 6.0 or slightly more within this range), and can be comprised of a variety of materials, including but not limited to one or more compositions selected from the group consisting of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

Enteric coatings can be applied by conventional coating techniques, such as pan coating or fluid bed coating, using solutions of polymers in water or suitable organic solvents or by using aqueous polymer dispersions. As an alternative embodiment, the release controlling enteric coating can separate additional antigen and/or drug layers on the core; for instance, after coating with the release controlling substance, another antigen and/or drug layer can be applied, which is followed by another release controlling layer, etc. For example, suitable materials for the release controlling layer include EUDRAGIT® (copolymers of acrylic and methacrylic acid esters), EUDRAGIT®RS (copolymers of acrylic and methacrylic acid esters), cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®, and the like.

These and other aspects of the invention are described further in the following non-limiting examples.

NON-LIMITING EXAMPLES OF THE PRESENT APPLICATION

Example 1. Step by Step: General Preparation and Testing of Cholestosome Encapsulated Proteins, Peptides and Genetic Material Cholestosomes Applied to an Oral Protein or Peptide Steps in the preparation of an oral drug molecule, oral protein, oral peptide, oral gene or construct of genetic material (the term "molecule" used to define one or all of these hereinafter in this example) and testing of said molecule for absorption in Caco2 cells are as follows:
1. Prepare cholesteryl esters and composition elements for encapsulation;
2. Obtain molecule targeted for encapsulation and test for purity and stability at 37 C-45° C.;
3. Optimize components of cholesteryl esters in the cholestosome mixture using a computer model of interactions between esters and molecule to achieve maximum cholestosome loading of said molecule;
4. Prepare cholestosome encapsulated molecule and include Fluorescein Isothicyanate (FITC) label for purposes of conducting biological studies including microscopy, said FITC label not a component of product intended for human testing or therapeutic use;
5. Test FITC labeled molecule in Caco2 cell monolayer and collect chylomicron encapsulated FITC-cholestosome-molecules, now defined as incorporated into cholestosome loaded chylomicrons;
6. Expose test cells to chylomicrons containing FITC-cholestosome-molecules and determine uptake of FITC-molecule by these test cells. While MCF-7 cells are often chosen because of their ease of use and relevance to cancer, workers will realize that testing many different cell lines for uptake in the case where cellular targeting is a subject of scientific investigation, as intracellular uptake of many bioactive molecules is novel and unanticipated from prior art in the field of drug delivery;
7. Define, using microscopy, whether intracellular FITC-molecule is contained in endosomes or it is free in cytoplasm; Typical time points for imaging of endosomes is approximately 24 hr after the initial exposure.
8. Define, using Western Blot expression of GLUT-transporters, whether the intracellular action of molecule is expressed as cell surface mediated uptake of additional substances or molecules controlled by actions of intracellular molecule;
9. Prepare enteric coated pH 5.5 release capsule with FITC-molecule-cholestosomes for administration to an animal or human (the preferred oral administration form for acid labile proteins, peptides, genes or live constructs such as vaccines or viruses);
10. Administer oral dosage form of FITC-molecule-cholestosome to mouse or human;
11. In the experiments of step 10. Administer same dose of FITC-molecule-cholestosome orally as FITC-molecule-cholestosomes in enteric coated capsule, IV; administer same dose of FITC-molecule-cholestosome IV;
12. Compare effects on a biomarker of molecule effect after administration of FITC-molecule-cholestosome between the three modes:
    a. oral as FITC molecule cholestosomes which result in lymphatic chylomicrons loaded with FITC molecule cholestosomes, vs.
    b. Intravenously administered as FITC-molecule cholestosomes which would not form chylomicrons and which may or may not facilitate absorption of molecules into cells vs.
    c. FITC-molecule intravenously and not in cholestosomes and therefore not in chylomicrons) at the same dose of molecule for each mode.
13. Using fluorescence microscopy, examine biodistribution of FITC-molecule in tissues taken from mice given the 3 modes of administration (a vs. b vs. c) in step 12 above. Tissues to be examined post mortem include liver, kidney, brain, pancreas, duodenum, ileum, colon, spleen, muscle, abdominal fat. It is anticipated that high intracellular concentrations of molecules can be achieved by this method, and that distribution in cells would be uniform instead of confined to endosomes or digestive vacuoles. Measurement of effect of molecule would be correlated with intracellular distribution profile and a measure of overall bioactivity vs. dose would be derived from the effect measurements.

Figure 12:
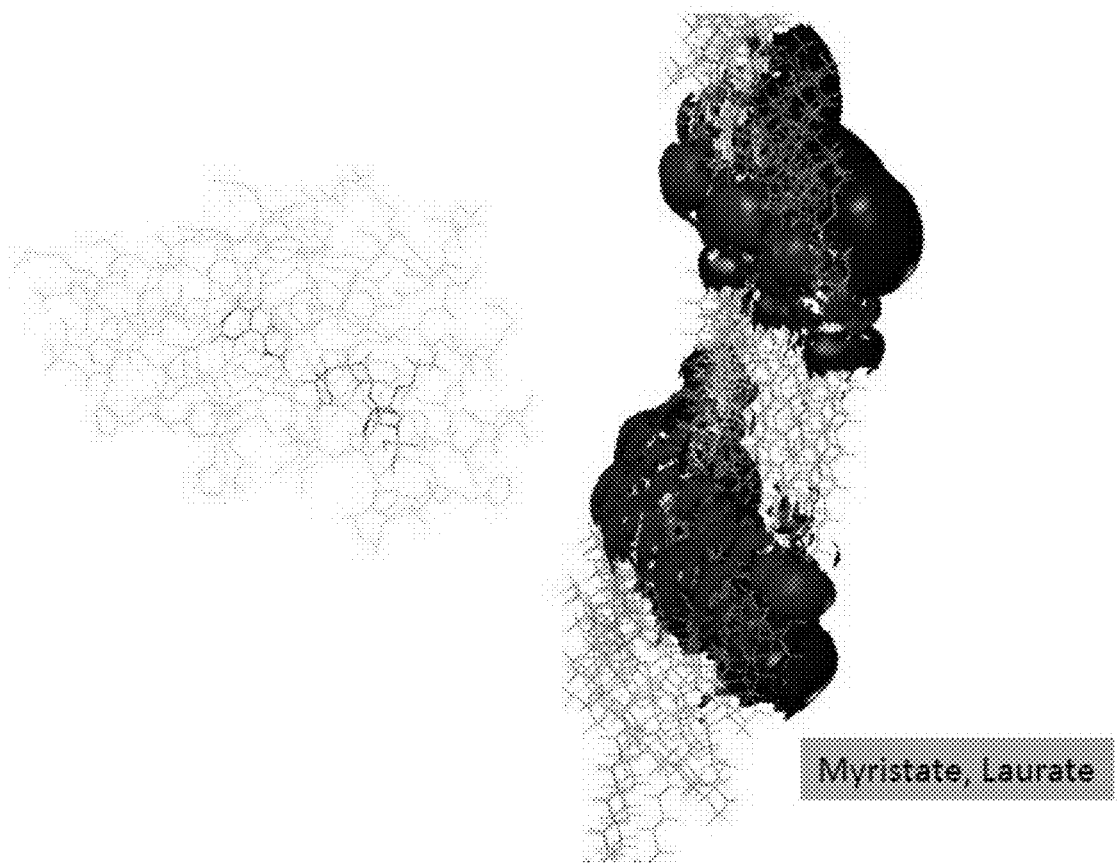
FIG. 12 shows an image section of a matrix formed from myristate and laurate assembled in an inter-digitated alternating alkyl chain model around Insulin. Charges were calculated and electrostatic potential maps were generated. Note the blue/red regions indicate of a more hydrophilic region with the alkyl chains inter-digitating to form the vesicle. The illustrated molecule inside the insulin matrix (yellow) is ceftaroline, a hydrophilic molecule with mw approximately 600 daltons. The overlay was performed to illustrate size differences, and does not imply any intent by the inventors to combine these two molecules in the same cholostosome.

FIG. 12. Structure of a Cholestosome with Encapsulated Protein

Shown in FIG. 12 is a loaded cholestosome structural model with encapsulated insulin as an example. It is assumed that these ideal lipid particles are aggregated into clumps of lipid, with raw production sizes of clumps of about 1000-5000 nm. Extrusion of these large particles down to uniformly sized 250 nm particles is a preferred embodiment. This can be effected using a standard high pressure extrusion device, well known in the art.

Example 2. Cholesteryl Ester Composition and Layering

Preliminary Studies of Cholesteryl Esters Considered for Use in Manufacture of Cholestosomes.

Define the melting point of each ester. By way of example, myristate has a melt transition temperature of 65 degrees centigrade, above which temperature the solid component melts.

The formulation objective was to use cholesteryl esters at temperatures below the melt temperature. (Consistent with liposome preparations), and considering that proteins begin to denature at temperatures about 40 degrees centigrade.

Further temperature testing was carried out on the chosen esters myristate and laurate. After the organic solvent was completely removed from the lipids in the rotovap, a DSC was conducted, which showed two melting temperatures, one approximately 60 degrees centigrade and a second melt at a higher Temperature.

On the basis of these findings and considering the stability of the proteins and peptides being formulated, the operating temperature of encapsulation procedures was kept between 45 and 55 degrees centigrade.

Selection of Cholesteryl Esters and Compositions for Encapsulation of Molecules in Cholestosomes Selection of specific cholesteryl esters for the proper formation of encapsulating vesicles involves a novel approach and a computerized molecular model. Properties of the cholesteryl esters and the interaction between the target molecule for encapsulation and the inner hollow core of vesicle formed from the esters around the molecule can be used to define favorable cholestosome-molecule properties such as loading, either on a volume to volume basis or a weight to weight basis.

Cholestosome Vesicles prepared without molecules loaded inside, have an average diameter of 250 nm after extrusion. The size can be modified as a function of size of cholesteryl esters, mole ratios in mixtures of different cholesteryl esters, filtration techniques, sonication times, and temperature.

a. Cholesteryl esters claimed that form cholestosomes include: Any cholesteryl ester produced from cholesterol and a fatty acid, where a fatty acid includes both saturated and unsaturated fatty acids including but not limited to the following compounds in Table 2 below:

TABLE 2

Listing of fatty acids used to form cholesteryl esters, characterized by structure, ratio of Carbons to number of double bonds the ratio C:D and position of the double bonds

| Common name-Acid | Chemical structure | C:D | Position of double bond |
|---|---|---|---|
| Myristoleic | $CH_3(CH_2)_3CH=CH(CH_2)_7COOH$ | 14:1 | n-5 |
| Palmitoleic | $CH_3(CH_2)_5CH=CH(CH_2)_7COOH$ | 16:1 | n-7 |
| Sapienic | $CH_3(CH_2)_8CH=CH(CH_2)_4COOH$ | 16:1 | n-10 |
| Oleic | $CH_3(CH_2)_7CH=CH(CH_2)_7COOH$ | 18:1 | n-9 |
| Elaidic | $CH_3(CH_2)_7CH=CH(CH_2)_7COOH$ | 18:1 | n-9 |
| Vaccenic | $CH_3(CH_2)_5CH=CH(CH_2)_9COOH$ | 18:1 | n-7 |
| Linoleic | $CH_3(CH_2)_4CH=CHCH_2CH=CH(CH_2)_7COOH$ | 18:2 | n-6 |
| Linoelaidic | $CH_3(CH_2)_4CH=CHCH_2CH=CH(CH_2)_7COOH$ | 18:2 | n-6 |
| α-Linolenic | $CH_3CH_2CH=CHCH_2CH=CHCH_2CH=CH(CH_2)_7COOH$ | 18:3 | n-3 |
| Arachidonic | $CH_3(CH_2)_4CH=CHCH_2CH=CHCH_2CH=CHCH_2CH=CH(CH_2)_3COOH^{NIST}$ | 20:4 | n-6 |
| Eicosapentaenoic | $CH_3CH_2CH=CHCH_2CH=CHCH_2CH=CHCH_2CH=CHCH_2CH=CH(CH_2)_3COOH$ | 20:5 | n-3 |
| Erucic | $CH_3(CH_2)_7CH=CH(CH_2)_{11}COOH$ | 22:1 | n-9 |
| Docosahexaenoic | $CH_3CH_2CH=CHCH_2CH=CHCH_2CH=CHCH_2CH=CHCH_2CH=CHCH_2CH=CH(CH_2)_2COOH$ | 22:6 | n-3 |
| Caprylic | $CH_3(CH_2)_6COOH$ | 8:0 | |
| Capric | $CH_3(CH_2)_8COOH$ | 10:0 | |
| Lauric | $CH_3(CH_2)_{10}COOH$ | 12:0 | |
| Myristic | $CH_3(CH_2)_{12}COOH$ | 14:0 | |

TABLE 2-continued

Listing of fatty acids used to form cholesteryl esters, characterized by structure, ratio of Carbons to number of double bonds the ratio C:D and position of the double bonds

| Common name-Acid | Chemical structure | C:D | Position of double bond |
|---|---|---|---|
| Palmitic | $CH_3(CH_2)_{14}COOH$ | 16:0 | |
| Stearic | $CH_3(CH_2)_{16}COOH$ | 18:0 | |
| Arachidic | $CH_3(CH_2)_{18}COOH$ | 20:0 | |
| Behenic | $CH_3(CH_2)_{20}COOH$ | 22:0 | |
| Lignoceric | $CH_3(CH_2)_{22}COOH$ | 24:0 | |
| Cerotic | $CH_3(CH_2)_{24}COOH$ | 26:0 | |

In the above table, C is the number of carbons and D is the number of double bonds in the alkyl chain of the fatty acid molecule, C:D ratio of the molecule as displayed. The position of the double bond is expressed as the number of carbon after the carbonyl, which is position 1 in the chain. In this manner, n-5 for myristoleic acid means that the double bond is found at position 14-5=position 9

The term "cholesterol" is used in the present invention to describe any cholesterol compound which may be used in the preparation of the cholesteryl esters which may be used to form cholestosomes pursuant to the present invention. The term "cholesterol" and includes the molecule identified as cholesterol itself, and any related cholesterol molecule with additional oxygenation sites ("an oxygenated analog of cholesterol") as in for example (but not limited to), 7-keto-cholesterol, 25-hydroxy cholesterol, 7-beta-hydroxycholesterol, cholesterol, 5-alpha, 6-alpha epoxide, 4-beta hydroxycholesterol, 24-hydroxycholesterol, 27-hydroxycholesterol, 24,25-epoxycholesterol. Oxysterols can vary in the type (hydroperoxy, hydroxy, keto, epoxy), number and position of the oxygenated functions introduced and in the nature of their stereochemistry. These various cholesterols may be used to provide cholesterol esters which vary in solubility characteristics so as to provide some flexibility in providing a cholestosome with a neutral surface and groups which can instill hydrophilicity in the cholesterol ester molecules. The cholesterol type molecule could also include any sterol structurally based compound containing the OH necessary for ester formation such as Vitamin D.

Molar ratios claimed in beneficial formation of cholestosomes range from 0.05 to 0.95 of any pair of esters (when a pair of esters is used) listed in table 2 above. Product ratios of composition between pairs of approximately equal alkyl chain length cholesteryl esters and active molecules range from about 2:2:96 to 48:48:4, often 45:45:10 to about 2:2:96, about 40:40:20 to about 5:5:90, about 40:40:20 to about 25:25:50. It is noted that in many cholestosome formulations when two (or more) cholesteryl esters are used, the ratio may vary above or below a 1:1 ratio for the cholesteryl esters used.

Filtration techniques claimed include vacuum filtration for initial size selection and then extrusion of preparations for finer size selection.

Sonication times range from 30 min to 120 minutes. This time is presented as a range, in that centrifuge time is a variable. Optimal sonication time depends on the ability to find the optimal sonication spot in the sonicator, and at optimal timing, the solution forms a cloudy appearance and the amount of solid material should be minimal as determined at this point by visual inspection.

Temperature range during production of cholestosome vesicles is 35° C. to 45° C. when working with most of the cholesteryl esters in Table 2. Temperature is held constant (+/−5C) throughout the preparation of the vesicles. Temperature is kept below the melt temperature of any of the individual esters. By way of example, for the preparation of cholestosomes using myristate/laurate, temperature is held at 40° C.+/−5 C. Addition of small amounts of between to the mixture prior to sonication increase overall yield of cholestosomes and facilitate the production of more uniform particles.

By means of example, the following principles define the basis for choice of a component ester in a cholestosome, a means of choosing an ester or ester pair for encapsulation purposes, and rely on the disclosed physiochemical properties of the listed cholesteryl esters in Table 2:

1) The esters chosen for combination should be able to arrange themselves to optimize the ester link interactions between ester pairs. This electrostatic interaction is important for orientation purposes, with the necessary hydrophobic exterior and hydrophilic center of the vesicle.
2) The alkyl interactions should be able to optimize van der Waals forces.
3) The sum of electrostatic interactions and the alkyl interaction van der Waals forces are fundamental properties that hold the vesicle shape and thereby retain the molecule inside. A key additional factor for stability of cholestosome vesicles includes the degree of repulsion between the dual hydrophobic ends of the esters and the aqueous component containing the molecule(s) to be encapsulated.
4) The overall size of the vesicle becomes a function of the length of the alkyl chain. The increased length of the esters chosen will increase the overall hydrophobic character of the entire vesicle.
5) Using smaller chain length esters will actually increase the overall hydrophilic character of the vesicle (in terms of the overall structure of each ester).
6) Molecules that require more hydrophobic areas to assist in encapsulation within the vesicle could benefit from esters having longer alkyl chains.
7) Molecules that are smaller and require more hydrophilic components to assist in encapsulation would benefit from ester pairs that are shorter in length.
8) An additional choice is the use of unsaturated alkyl chains such as those listed in Table 2, where these fatty acids are used to prepare ester side chains for use in forming cholesteryl esters.
9) The use of an unsaturated fatty acid offers an additional structural modification in the vesicle structure which incorporates additional electrostatic interactions between the aqueous and the double bond character.
10) In the process of selection of esters for vesicle formation, selection of $CH_2$ chain lengths ranging for example from 2 $CH_2$ units but less than 27 $CH_2$ in length result in a structure that may not be as tight, as a result of the challenges in adapting the alkyl chains to maximize their interactions in a vesicle. The cholesterol component of the vesicle wall does not change. The van der Waals interactions within $CH_2$ units governs the flexibility of the alkyl interactions. However, for beneficial hydrophilic vesicle center, the optimal configuration in this vesicle is longer alkyl chains, meaning that larger ester molecules have greater utility for stabilizing more hydrophilic vesicle centers of the vesicle exposed to the aqueous environment in formulation stability.

Figure 6:
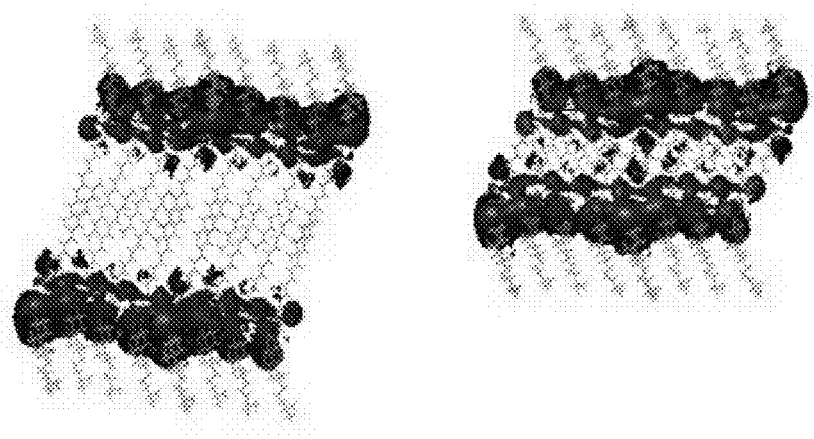
FIG. 6 shows the impact of ester chain length during molecular modeling of cholesterol esters using SYBYL (Tripos, St Louis Mo.) on an HP XW8000 workstation. Shown is the contrasting models formed using different pairs of approximately equal alkyl chain length cholesterol esters. The GASTIGER Huckel method was used to calculate charges, which are the input for the electrostatic isopotential map. The isopotential surfaces displayed are at −10 and +10 kcal to highlight the ester link and the sterol nucleus. The red color is −10; blue is +10 kcals. The resulting differences in the center of the figures are the ester links. Note that changing the length of the esters in the model does not change the surface or interior, but this change does bring the sterol nuclei closer to each other. It also changes size of internal diameter as well as character of the hydrophobic "tracks"
Figure 7:
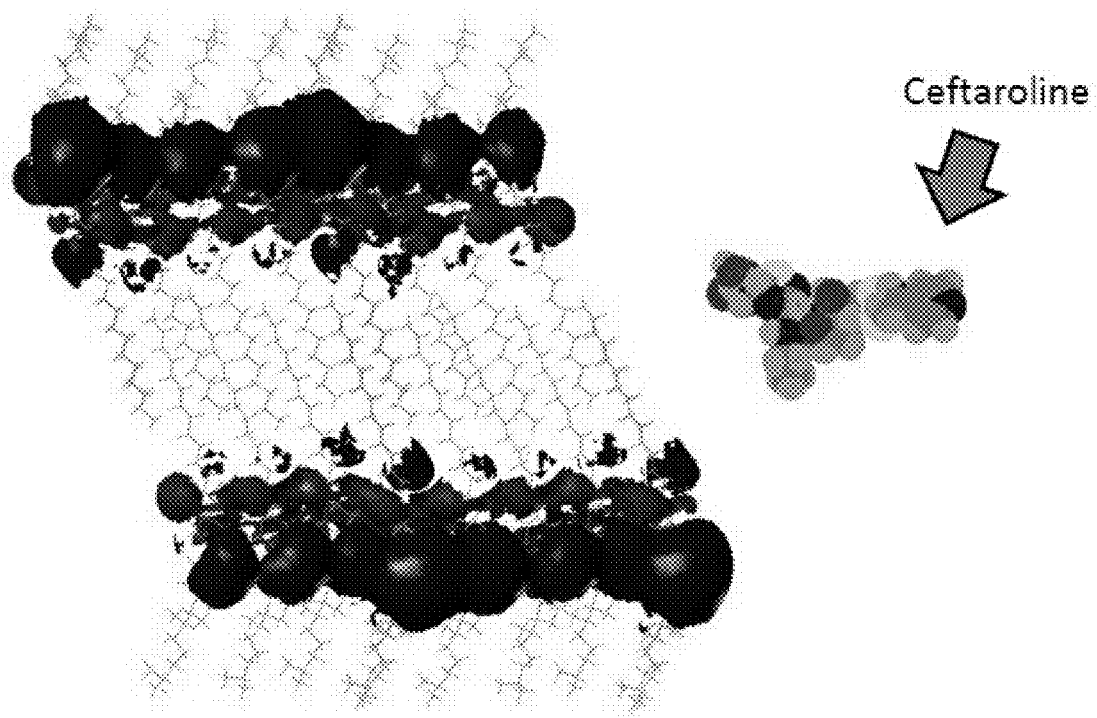
FIG. 7 shows an image section of a matrix formed of cholesteryl esters of myristate and laurate. Charges were calculated and electrostatic potential maps were generated. Note the blue/red regions, indicative of a more hydrophilic region with the alkyl chains inter-digitating to form the bilayer. The illustrated molecule is ceftaroline, a hydrophilic molecule with mw approximately 600 daltons and size of 1.8 nm at its widest point.
Figure 8:
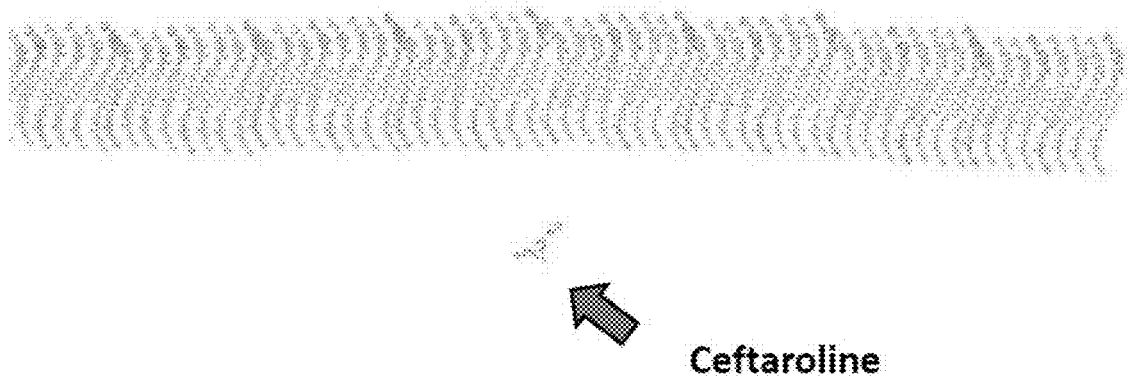
FIG. 8 shows Ceftaroline in relation to the matrix formed and illustrated by molecular modeling of cholesterol esters myristate and laurate using SYBYL (Tripos, St Louis Mo.) on an HP XW8000 workstation. Interdigitizing alkyl chains are shown from the two cholesterol esters, in this example myristate and laurate. These structures form the outer membrane and the inner surface compatible with the molecule Ceftaroline, in this case. Ceftaroline is 1.8 nm at its widest spot. A cholestosome diameter is 250 nm. Based on membrane size, a fully loaded cholestosome is 96% content inside with a water soluble molecule.
Figure 9:
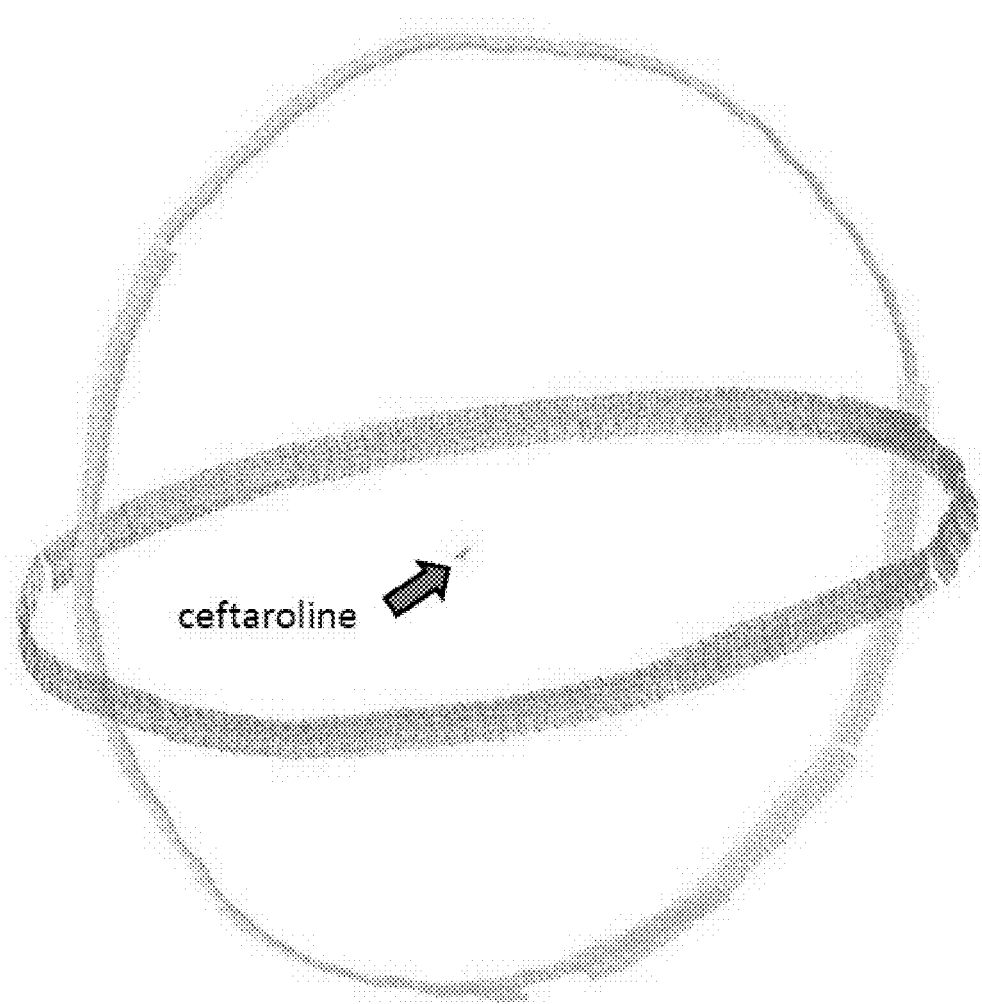
FIG. 9. shows a close in illustration of Ceftaroline in basic cholestosome matrix arranged in a ring. Ceftaroline is a very small molecule—1.8 nm and loaded in a 115 nm cholostosome, for relative size illustration purposes. The rings are chains of cholesteryl esters
Figure 10:
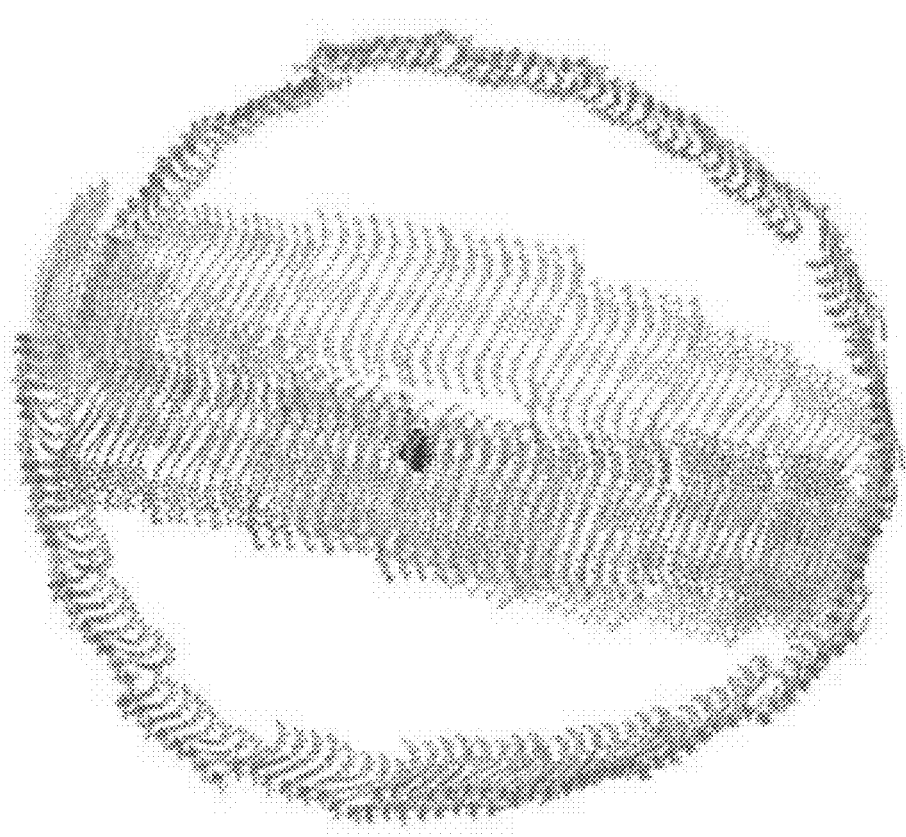
FIG. 10 shows a partially assembled cholostosome around Ceftaroline, with one molecule shown. The partially assembled cholostosome matrix reveals walls and structures in relation to the ceftaroline molecule. Sizes include: membrane shown is 4 nm wide. Ceftaroline is 1.8 nm in length. The internal diameter of the hydrophilic inner core pocket is 65 nm
Figure 11:
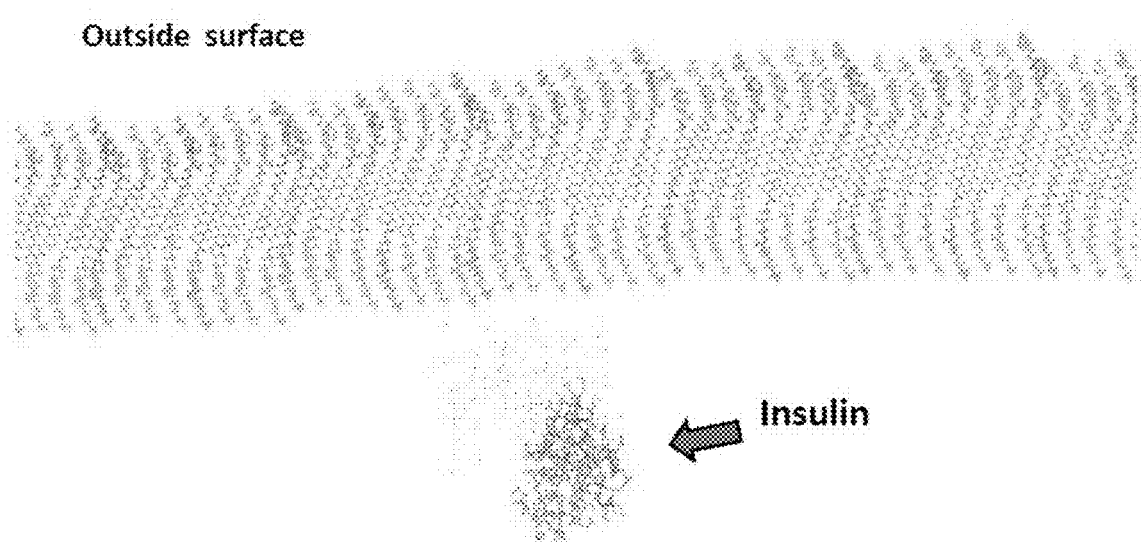
FIG. 11 shows molecular modeling of insulin in relationship to the matrix of cholesterol esters using SYBYL (Tripos, St Louis Mo.) on an HP XW8000 workstation. Inter-digitizing alkyl chains are shown from the two cholesterol esters, in this example myristate and laurate. These structures form the outer membrane and the inner surface compatible with the molecule shown, in this case insulin. Sizes include: The membrane shown is 36 nm long and 4 nm wide. Insulin is 4 nm at widest spot. A cholostosome diameter is 250 nm. Based on membrane size, a fully loaded cholostosome hollow inner core could be as high as 96% of the content inside, assuming a tightly packed center with a water soluble molecule.
Figure 13:
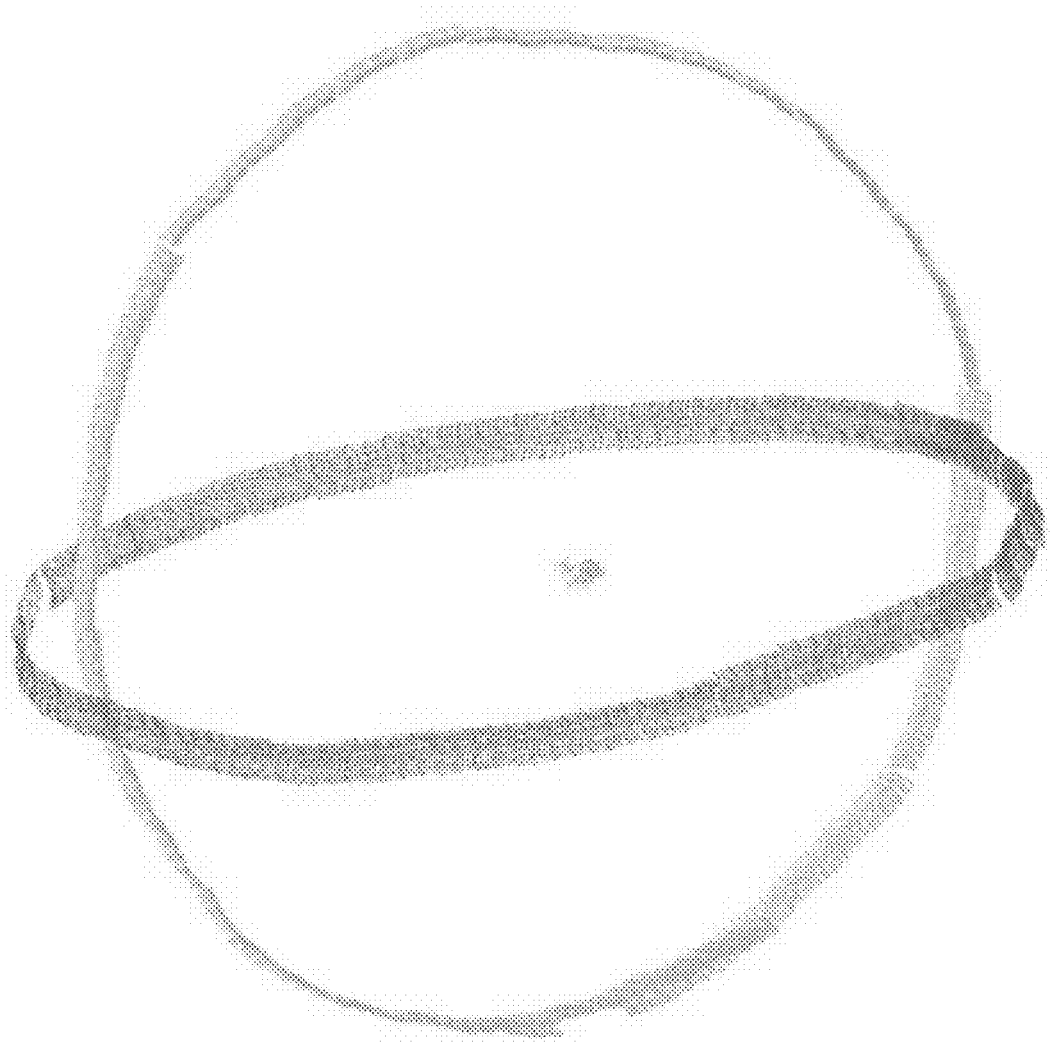
FIG. 13 shows a close in illustration of insulin in a basic cholostosome matrix, in this case formed from cholesterol esters of myristate and laurate. Sizes include: the membrane shown as matrix is 36 nm long and 4 nm wide Insulin is 4 nm at the widest spot. The diameter of the cholostosome vesicle shown is 100 nm for illustration purposes.
Figure 14:
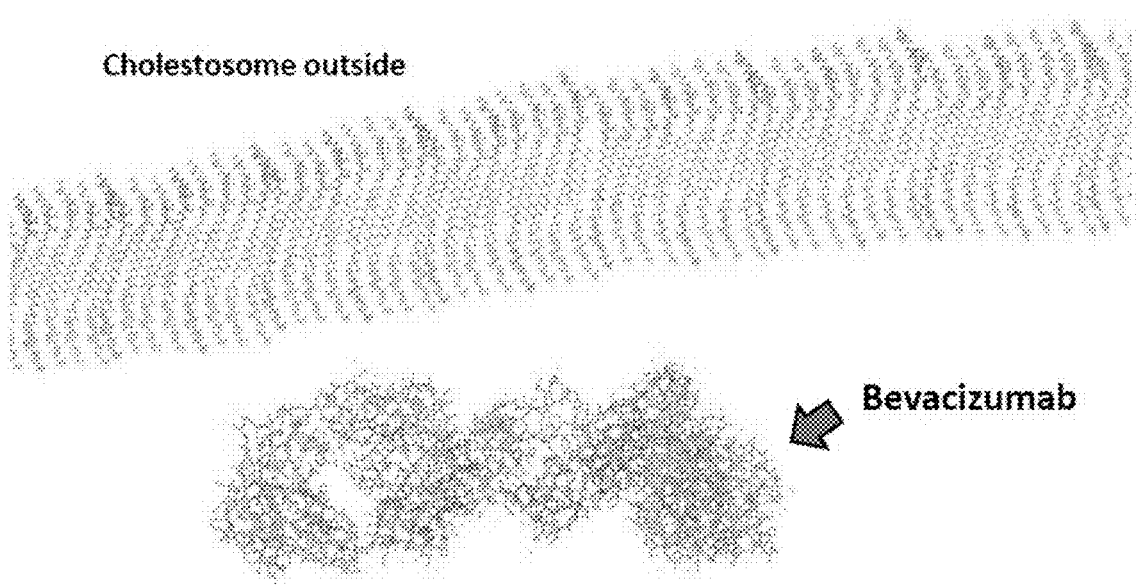
FIG. 14 shows molecular modeling of bevacizumab in relation to cholesterol esters using SYBYL (Tripos, St Louis Mo.) on an HP XW8000 workstation. Interdigitizing alkyl chains are shown from the two cholesterol esters, in this example myristate and laurate. These structures form the outer membrane and the inner surface compatible with the molecule shown, in this case bevacizumab. Sizes include: bevacizumab at 17 nm long and 4 nm wide, while the membrane shown is 36 nm long and 4 nm wide in a single matrix ring. A cholostosome diameter for Bevacizumab unextruded is 10,000 nm and extruded is 250 nm. Based on membrane size, a fully loaded cholostosome bound with a single bilayer ring has 96% of the content by weight to weight inside with a water soluble molecule.
Figure 15:
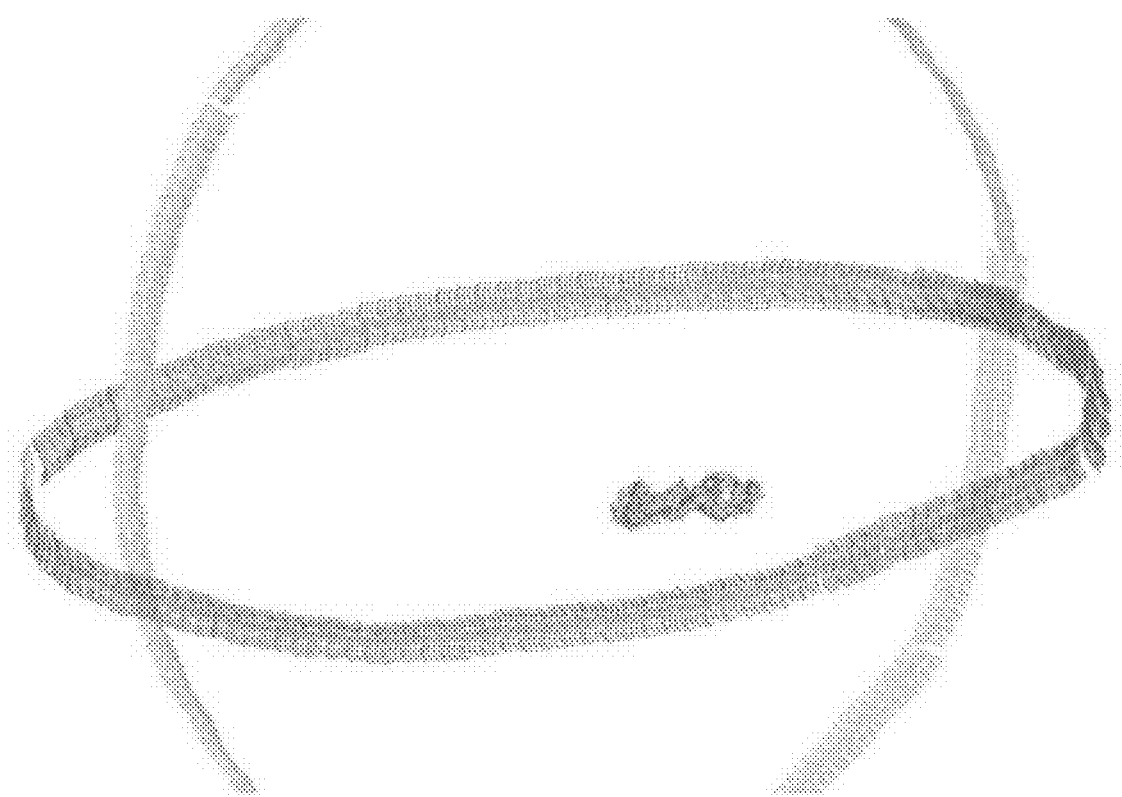
FIG. 15 shows a close in illustration of Bevacizumab in a basic cholostosome matrix, in this case formed from cholesterol esters of myristate and laurate. Volume of a 250 nm cholostosome is 7 million cubic nanometers, or $7 \times 10^{-15}$ ml. Assuming it is unilamellar, if we are calculating making a loading factor out of this the cholostosome contains 4% of the volume and the solution within it contains is 96% of the volume. Sizes include: bevacizumab at 17 nm long and 4 nm wide the membrane shown has a diameter of 100 nm
Figure 16:
FIG. 16 shows molecular modeling of Bevacizumab, Insulin, Ceftaroline in a basic Cholostosome matrix formed from cholesterol esters using SYBYL (Tripos, St Louis Mo.) on an HP XW8000 workstation. Interdigitizing alkyl chains are shown from the two cholesterol esters, in this example myristate and laurate. These structures form the outer matrix and the inner surface compatible with the molecules shown, in this case bevacizumab, insulin and ceftaroline. Based on membrane size, a fully loaded cholostosome is 96% content inside when loaded with a water soluble molecule. Loading can be calculated based on v/v (volume of the vesicle and volume of the molecule). Assumptions: the cholostosome is a sphere with a diameter of 250 nm. The internal core hydrophilic pocket diameter is then 242 nm with a radius of 121 nm. This results in a total cholostosome volume of approximately 7 million roan (cubic nanometers). We can calculate the volume of a molecule and calculate the total numbers potential (not including solvent) and calculate a mass ratio of vesicle to molecule in that manner. Another way is to consider the volume of the vesicle and consider the concentration of the analog to be encapsulated. For example, bevacizumab in solution at 100 mg/ml. Converting cubic nanometers to ml and then determine how much can fit in a cholostosome and compare mass in that manner. Upon conversions, this results in a mass ratio where bevacizumab to lipid ratio in content is about 96:4%

FIGS. 6-7 illustrate molecular modeling diagrams by means of an example of Cholestosome vesicle matrix formation from two different pairs of cholesteryl esters selected from Table 2. In FIGS. 8-10 of the myristate-laurate matrix example chosen here, the inventors used molecular modeling to illustrate the impact on a small water soluble molecule Ceftaroline. The cholestosomes formed for Ceftaroline have composition ratios of 5:5:90 with the chosen pair of cholesteryl esters. In FIGS. 11-13, the representative peptide molecule was Insulin, a peptide of 6 kd size that is generally water soluble. In FIGS. 14-15, the cholestosome vesicle structure was applied to encapsulate bevacizumab, a representative monoclonal antibody of size approximately 150 kd. In FIG. 16 all 3 representative molecules are shown in relation to the cholestosome vesicle formed from cholesteryl esters myristate and laurate.

For ester pairs that are greater than 6 $CH_2$ units different in length (which is defined as intermediate) it is possible to maintain ester interactions and turn the molecules in opposite directions to still have alkyl chains packed into a vesicle. This arrangement would be useful for packing in molecules that have alternating structural regions of hydrophobic/hydrophilic character, and which when incorporated into said vesicle, could be relied upon to segregate different molecule types.

The choice of ester pairs is a function of the structure of the molecule needed to be encapsulated and its ability to interact with the vesicle.

In FIGS. 8-10, an outline structure of the entire cholestosome is shown, with inserted molecule ceftaroline. Insulin is shown in FIGS. 11-13, and in FIGS. 14-15 the molecule shown is bevacizumab. In FIG. 16, the matrix is shown around Ceftaroline, insulin and bevacizumab illustrated next to each other, which nicely illustrates the relative sizes of these molecules in relationship to the size of the cholestosome matrix. All three of these molecules can be effectively encapsulated by this methodology and used in humans after oral administration. In each case there is no known effective means of oral absorption, other than as disclosed in the present invention.

Example 3. Antibiotics Anti-Fungals, Anti-Virals and Other Small Molecules in Cholestosomes for Oral Use In the present invention, molecules used for the treatment of infectious diseases would be generally suitable for encapsulation into cholestosomes and used orally. Most antibiotics need to be injected intravenously (IV), as the molecules are typically hydrophilic and not otherwise orally absorbed. Thus use in cholestosomes would make enable their oral absorption. Numerous antibiotics may be used in cholestosomes according to the present invention including Antibiotics for use in the present invention include Aminoglycosides, including Gentamicin, Kanamycin, Neomycin, Netilmicin. Tobramycin, Paromomycin, Spectinomycin; Ansamycins, including Geldanamycin, Herbimycin Rifaximin and Streptomycin; Carbapenems, including Ertapenem Doripenem Imipenem/Cilastatin and Meropenem; Cephalosporins, including Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime Cefpodoxime, Ceftazadime, Ceftibuten, Ceftizoxime Ceftriaxone, Cefepime, Ceftaroline fosamil and Ceftobiprole; Glycopeptides, including Teicoplanin, Vancomycin and Telavancin; Lipopeptipdes, including Daptomycin, Oritavancin, WAP-8294A; Macrolides, including Azithromycin. Clarithromycin, Dirithromycin, Erythromycin, Roxithromycin, Telithromycin and Spiramycin; Lincosamides, including Clindamycin and Lincomycin; Monobactams, including Aztreonam; Nitrofurans, including Furazolidone and Nitrofurantoin; Oxazolidonones, including Linezolid, Posizolid, Radezolid and Torezolid; Penicillins, including Amoxicillin, Ampicillin, Azlocillin, Carbenicillin. Cloxacillin Dicloxacillin, Flucloxacillin, Mezlocillin, Methicillin, Nafcillin, Oxacillin, Penicillin G, Penicillin V, Piperacillin, Temocillin and Ticarcillin; Penicillin combinations including Amoxicillin/clavulanate, Ampicillin/sulbactam, Piperacillin/tazobactam and Ticarcillin/clavulanate; Polypeptides, including Bacitracin, Colistin and Polymyxin B; Quinolones/fluoroquinolines, including Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin. Grepafloxacin, and Sparfloxacin; Sulfonamides, including Mafenide, Sulfacetamide. Sulfadiazine, Sulfadimethoxine, Sulfamethizole, Sulfamethoxazole, Sulfasalazine, Sulfisoxazole, Trimethoprim-Sulfamethoxazole and Sulfonamidochrysoidine; Tetracyclines, including Demeclocycline, Doxycycline, Vibramycin Minocycline, Tigecycline, Oxytetracycline and Tetracycline; Anti-mycobacterial agents, including Clofazimine, Capreomycin, Cycloserine, Ethambutol, Rifampicin, Rifabutin, Rifapentine, Arsphenamine, Unclassified including Chloramphenicol, Fosfomycin, Fusidic acid, Metronidazole, Mupirocin, Platensimycin, Quinupristin/Dalfopristin, Thiamphenicol, Tigecycline, Tinidazole and Trimethoprim.

None of these molecules are orally absorbed in the native state, and in each case oral absorption would constitute a major advantage over the current need to inject them parenterally in treatment of infectious diseases.

Examples of anti-fungal compounds for use in the practice of the art as applied to cholestosome encapsulation include but are not limited to the following miconazole, terconazole, econazole, isoconazole, tioconazole, bifonazole, clotrimazole, ketoconazole, butaconazole, itraconazole, oxiconazole, fenticonazole, nystain, naftifine, amphotericin B, zinoconazole and ciclopiroxolamine, micafungin, caspofungin, and/or anidulafungin.

Examples of anti-viral compounds for use in the practice of the art as applied to cholestosome encapsulation include but are not limited to the following Ribavirin, telaprevir, daclatasvir, asunaprevir, boceprevir, sofosbuvir, BI201335, BI1335; ACH-2928, ACH1625; ALS-2158; ALS2200; BIT-225; BL-8020; Alisporivir; IDX19368; IDX184; IDX719; Simeprevir; BMS-790052; BMS-032; BMS-791325; ABT072; ABT333; TMC435; Danoprevir; VX222; mericitabine; MK-8742, GS-5885 or a mixture thereof, interferon, Pegylated Interferon, Pegylated interferon lambda or any other suitable formulation of said interferon.

Representative examples of anti-infective preparations in cholestosomes are disclosed herein, so as to illustrate the properties of anti-infective substances in cholestosomes.

Tobramycin

A preferred embodiment illustrative of the molecules disclosed herein is tobramycin, selected from this list for preparation and testing of cholestosome encapsulated tobramycin according to the principles enumerated in Example 1. The particular preparation was designed for oral use, and for increasing the overall action of the antibiotic tobramycin against target gram negative bacteria such as *Pseudomonas aeruginosa.*

By way of specific example, tobramycin cholestosomes with mean diameter of 250-1,000 nm were prepared in the manner of the present invention, as described in Example 1, with cholesteryl ester selection from the esters disclosed as preferred in Example 2. Cholestosomes containing tobramycin were prepared using a novel blend of two cholesteryl esters, cholesteryl myristate and cholesteryl laurate.

Tobramycin Formulation Properties
Batch Properties
DLLS particle size: 2700 nm
Zeta Potential: −21.7
Concentration of Lipids: 1.9 mg/ml. Concentration of Tobramycin: 2.0 mg/ml
Cell exposures: MCF-7 cells (See FIG. 23)
Cholestosomes alone; No effect on growth or viability over 24 hr
FITC alone: No effect on growth or viability over 24 hr
Tobramycin Alone: 10 mcg/ml to 0.01 mcg/ml No effect on growth or viability over 24 hr
FITC Tobramycin alone: 10 mcg/ml No effect on growth or viability over 24 hr
FITC Tobramycin cholestosomes: 3.0 mcg/ml 24 hr killing, repeated, same result. Postulated 100× inside vs outside, with intracellular killing threshold similar to renal tubular lining cells.
Conclusions: Cholestosomes alone, FITC cholestosomes alone, Tobramycin alone do not kill MCF-7 cells. FITC-tobramycin on MCF-7 cells also does not harm them. However, FITC-tobramycin-cholestosomes kills at 24 hr.
No chylomicron studies conducted with FITC tobramycin cholestosomes FIG. 23 FITC Tobramycin Cholestosomes Comparing MCF-7 cells by bright field vs FITC fluorescence imaging shows 1) an overall successful loading of MCF-7 cells after 24 hr exposure to FITC-cholestosomes, which has been shown repeatedly in our work with cholestosomes.

In 2), this response of approximately 100 fold greater concentration of tobramycin inside MCF-7 cells is unexpected, particularly when the loading of cells by cholestosomes is compared with the general lack of intracellular loading of MCF-7 cells w % ben exposed to FITC-tobramycin alone. Low loading is the expected result, as it is well known that tobramycin does not enter most body cells, and any cell that takes up tobramycin actively is subject to the intracellular killing from tobramycin by virtue of its effect on mitochondria and cell energy supply via ATP production. This is the basis for tobramycin's well known nephro and oto toxicity.

In 3) and of great interest, when MCF-7 cells were exposed to FITC-Tobramycin-cholestosomes for 24 hr, these MCF-7 cells all died, as can be seen in the last frame at both top and bottom. The purpose here is to show how tobramycin, when it enters cells, is a general toxin to the mitochondria and when tobramycin enters even cells otherwise resistant to its intracellular effects, there is potential for intracellular uptake and harm.

Ceftaroline

By way of a specific example concerning a cephalosporin antibiotic that is not absorbed orally and is therefore currently given by IV administration only, we chose the anti-MRSA cephalosporin antibiotic Ceftaroline fosamil.

Commercially available Ceftaroline was purchased from the hospital pharmacy, and Ceftaroline cholestosomes were prepared in the manner of the present invention, as described in Example 1, with cholesteryl ester selection from the esters disclosed as preferred in Example 2. We were unable to FITC label Ceftaroline, so the batches were tested for their antimicrobial properties as the primary means of defining the efficacy of the formulation.

Test batches of cholestosomes containing Ceftaroline were prepared using a novel blend of two cholesteryl esters, cholesteryl myristate and cholesteryl laurate. The choice of cholesteryl esters for composition is made from the disclosed compounds of Example 2, although this is not meant to be limiting and if there are other suitable cholesteryl esters for formulation with ceftaroline or similar molecules, they may be permitted in this formulation.

In the specific preparation of an optimal cholestosome formulation containing Ceftaroline, any cholesterol ester may be chosen as a component of the cholestosome and be within the spirit of the invention so long as the final Zeta Potential of the cholestosome product remains neutral charged.

Ceftaroline Formulation Properties
Batch:
FITC label fraction: not done
DLLS particle size not done and not extruded
Preparation dialyzed to remove free Ceftaroline: yes, but free Ceftaroline remains in the preparation
Percent yield 13% of starting amount of lipid
Zeta Potential: Not done
Bacterial testing with the dialyzed Ceftaroline; Retains anti-MRSA action, with MIC values at least 10× lower than parent Ceftaroline. Indicates active uptake by MRSA from cholestosome preparation.
Cells: MCF-7; 400,000 cells at 24 hr in a confluent prep. MCF-7 cell Size is 2000 nm
Cholestosomes alone; No effect on MCF-7 cell growth or viability over 24 hr
FITC alone: No effect on MCF-7 cell growth or viability over 24 hr
Ceftaroline Alone: No effect on MCF-7 cell growth or viability over 24 hr
FITC ceftaroline alone; Not prepared so not done
FITC ceftaroline cholestosomes: No effect on MCF-7 cell growth or viability over 24 hr
Postulate 100× inside vs outside.
Chylomicron forming Cells: Ceftaroline was/was not tested in Caco-2 cells
Vancomycin By way of a specific example concerning a glycopeptide antibiotic that is not absorbed orally and is therefore currently given by IV administration only, we chose the anti-MRSA glycopeptides antibiotic vancomycin.

Commercially available Vancomycin was purchased from Sigma chemical, and FITC vancomycin cholestosomes were prepared in the manner of the present invention, as described in Example 1, with cholesteryl ester selection from the esters disclosed as preferred in Example 2. The batches were fully tested against MCF-7 cells, Caco-2 cells and also tested for their antimicrobial properties against MRSA as the second primary means of defining the efficacy of the formulation.

Test batches of cholestosomes containing FITC-vancomycin were prepared using a novel blend of two cholesteryl esters, cholesteryl myristate and cholesteryl laurate. The choice of cholesteryl esters for composition is made from the disclosed compounds of Example 2, although this is not meant to be limiting and if there are other suitable cholesteryl esters for formulation with vancomycin or similar glycopeptides antibiotic molecules, they may be permitted in this formulation.

In the specific preparation of an optimal cholestosome formulation containing vancomycin, any cholesterol ester may be chosen as a component of the cholestosome and be within the spirit of the invention so long as the final Zeta Potential of the cholestosome product remains neutral charged.

Vancomycin Formulation Properties
Batch: 756, made 10-23-13
DLLS particle size 1016 nm not extruded
DLLS particle size: 800 nm extruded
Preparation dialyzed to remove free vancomycin
Percent yield <1.0% of starting amount of lipid
Zeta Potential: −13
Volume to Volume calculation:
Concentration of Lipids: 1.0 mg in 10 ml. Concentration of Vancomycin: 5000 mcg/ml
Weight to Weight calculation:
Concentration of Lipids: <1.0 mg/ml. There is free vanco in this preparation
Bacterial testing with the dialyzed version of this, which killed MRSA very well, vancomycin was approximately 10 times more active in cholestosomes than used alone.
Cells: MCF-7; 400,000 cells at 24 hr in a confluent preparation. MCF-7 cell Size is 2000 nm.
Cholestosomes alone; No effect for 24 hr
FITC alone: No effect for 24 hr
Vancomycin Alone: no effect; up to 666 mcg/ml, highest tested
FITC vanco alone; 666 mcg/ml to 41 mcg/ml: No effect for 24 hr
FITC vanco cholestosomes: No effect at 24 hr. At a vancomycin concentration of 0.83 mcg/ml from cholestosomes, FITC label study shows a very high internal vancomycin concentration in MCF-7 cells, equal to the image labeling of 666 mcg/ml, see FIG. 24. From these data it is possible to observe FITC-vancomycin concentrations 1000× inside vs outside as the effect of cholestosome loading.
Microbiological Activity against 4 different MRSA Strains: MIC values of cholestosome vancomycin were equal to vancomycin or in some cases up to 10× lower than vancomycin alone FIG. 24. FITC Vancomycin Cholestosomes.

Figure 24:
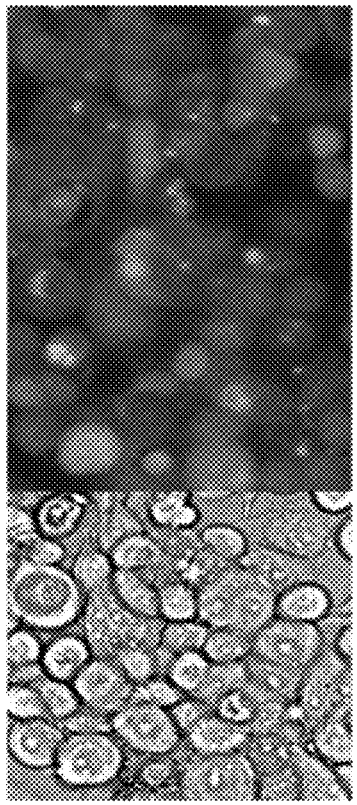
Figure 24:
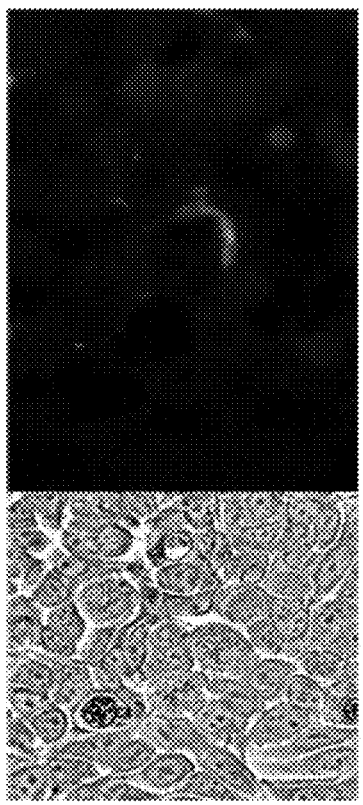
Figure 24:
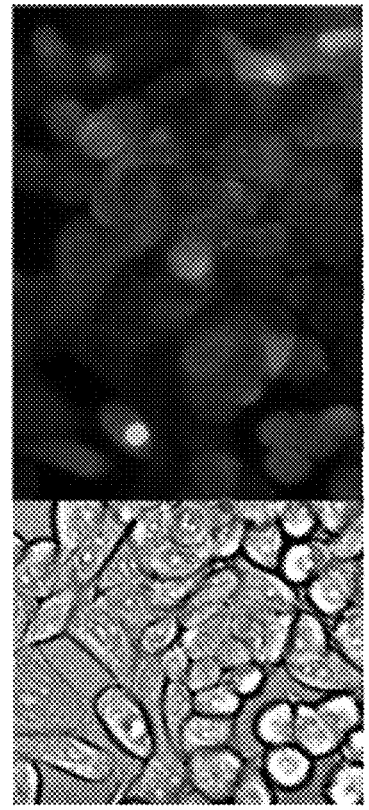

As shown in FIG. 24, vancomycin has some effective properties inside cells. This figure shows vancomycin entry into MCF-7 cells at 24 hr. In this series of experiments, the original starting concentrations of vancomycin were between 41 and 666 mcg/ml. In each column, the top image is the fluorescence, the bottom is the darkfield. Displayed out of this FITC-vancomycin series in column B is FITC vancomycin at 83 mcg/ml. In column A, FITC-vancomycin-cholestosomes at 0.83 mcg/ml produced greater uptake at a value 100 fold lower than the vancomycin concentration in FITC-vancomycin column B. The fluorescence image in column A shows more loading than the image in column B, indicating that the MCF-7 cellular loading ratio is more than 100× greater with FITC-vancomycin-cholestosomes. When the extracellular concentration of FITC-vancomycin was increased to 666 mcg/ml in column C, these cells are still not loading as high as those in column A. The fluorescence data on loading of FITC vancomycin is therefore approaching 1000× greater when cholestosomes are used. It should be noted that there was no effect of high amounts of FITC vancomycin cholestosomes on these MCF-7 cells. The images in the three panels confirm our observed penetration of FITC vancomycin cholestosomes inside cells. Not only are the cell membranes dramatically more concentrating FITC vancomycin in this image, but the cytoplasm of these cells is loaded with FITC vancomycin as well. This is after only 24 hr exposure, confirming that cholestosomes load massively more vancomycin in the cells.

Chylomicron forming Cells: Vancomycin was not tested in Caco-2 cells

Conclusion: Vancomycin alone. FITC vancomycin, FITC-vancomycin cholestosomes, all at high concentrations, do not harm MCF-7 cells. Vancomycin retains its antimicrobial action on MRSA organisms when encapsulated into cholestosomes.

Example 4. Insulin Cholestosomes

Specific Steps in Preparation of Insulin in Cholestosomes.

By way of specific example, Regular Insulin (Humulin, Lilly) cholestosomes were prepared in the manner of the present invention, as described in Example 1, with cholesteryl ester selection from the esters disclosed as preferred in Example 2. Test batches of cholestosomes containing insulin were prepared using a novel blend of two cholesteryl esters, cholesteryl myristate and cholesteryl laurate. The choice of cholesteryl esters for composition is made from the disclosed compounds of Example 2, although this is not meant to be limiting and if there are other suitable cholesteryl esters for formulation with insulin or similar molecules, they may be permitted in this formulation.

In the specific preparation of an optimal cholestosome formulation containing insulin, any cholesterol ester may be chosen as a component of the cholestosome and be within the spirit of the invention so long as the final Zeta Potential of the cholestosome product remains neutral charged. The two esters chosen for insulin using the principles disclosed in Example 2 were myristate and laurate, which differ in ester chain length by only two CH2 units, and when combined as disclosed provide a large internal hydrophilic center to the cholestosome vesicle prepared in this manner.

Optimizing the amounts of specific cholesteryl esters is fully within the scope of the present invention for purposes of producing an optimal loading and release profile of the insulin containing cholestosome for in vivo use.

Initial starting conditions are based on a 1:1 molar ratio of laurate/myristate, while the final ratio in the formulation of the various insulin molecules is not limited to that. Each insulin molecule will need to be examined in terms of its own structure and the molecular interactions with the putative cholesteryl esters as a means of final selection of cholesteryl esters for optimal loading. In the event the optimal final formulation requires a more hydrophobic area, then a longer chain fatty acid ester is used, as the entire proportion of hydrophobic space will change based on the length of the alkyl chain. If we need more centralized hydrophilic structures for certain insulin molecules, the intention is to use one of the oxysterols such as 7-keto cholesterol made into an ester with fatty acids.

The encapsulation molecule is insulin, to include but not limited to regular insulin, NPN insulin, insulin glargine, insulin degludec or any formulation of insulin prepared and shown to be bioactive in testing for insulin effects. Steps in preparation of the cholestosome formulation included the following:

Prepare a water bath to appropriate temperature (35-45) C; Place aqueous insulin prep (1 mg/ml) in PBS into water bath to equilibrate temperature; Weigh out equimolar amounts of cholesteryl laurate and cholesteryl myristate (75 mg each) and place in round bottom flask; Add organic solvent (diethyl-ether) to dissolve esters; swirl by hand to dissolve; Place round bottom flask on rotovap and spin for five minutes; Place flask attached to rotovap in water bath; turn on vacuum and spin for 10 minutes; Turn off rotovap and vacuum and add aqueous to round bottom flask; Add Tween; Spin on rotovap (no vacuum) for twenty minutes in water bath; Sonicate for 10 to 30 minutes until cloudy prep is formed and minimum solid is found in flask; Remove from sonication and filter using vacuum filtration; Save the cloudy filtrate; Extrude filtrate; Store preparation in refrigerator until use.

Figure 17:
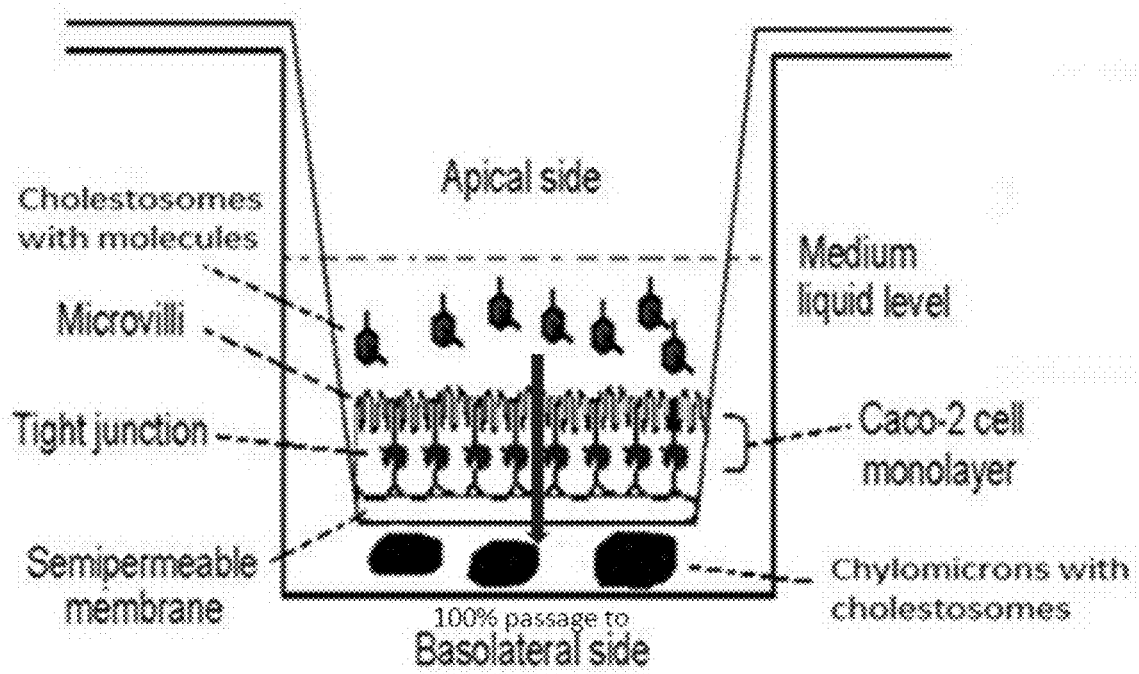
FIG. 17 shows an illustration of the apparatus used to collect basolateral fluids following exposure of the apical side of a monolayer of Caco2 cells to a cholostosome encapsulated molecule. Cholostosome encapsulated molecules of all sizes are taken into Caco-2 cells, and from there the loaded cholostosomes are incorporated intact into chylomicrons by the Golgi apparatus. The uptake process by enterocytes is more rapid and efficient than the process shown here for Caco-2 cells. Other typical components of Chylomicrons are APO-B; other apolipoproteins, and triglycerides. After formation, chylomicrons are secreted by Caco-2 cells into the lymphatic fluid on the basolateral side of the monolayer. Chylomicrons loaded with cholostosomes are captured in the fluid on the basolateral side of the Caco2 monolayer.

FIG. 17 Caco-2 Studies in Transwell; Formation of Chylomicrons

Employ Corning Transwell Permeable Supports in a 12 well format with a pore size of 0.4 um. Begin each Transwell experiment after Caco2 cells are 80-90% confluent in a 75 cm$^2$ flask. The cells are trypsinized as usual and counted using a hemocytometer. The cell concentration is adjusted to 2×10$^5$ cells/mL with culture media. The wells of the Transwell plate are seeded with 0.5 mL of the cell dilution. Media in a volume of 1.5 ml is added to the basolateral side. The cells are incubated as above and the media is changed every other day for 19-20 days. At this time the caco2 cells are differentiated and ready for treatment. All media from the upper and lower chambers of the Transwell plate is removed and both chambers are washed 3 times with PBS containing 1 mg/mL glucose (PBSG). PBSG is added to the upper and lower chamber of the plate and incubated for 1 hr. All PBSG is removed from both chambers and 1.5 mL of phosphate buffered saline with added glucose (PBSG) is added to the lower chamber.

The upper chamber receives 0.5 mL of the appropriate treatment (PBSG alone, FITC cholestosomes in PBSG or FITC-insulin cholestosomes in PBSG). All wells have a final concentration of 1.0 mg/mL glucose. The plate is then incubated for 2 hours. All solution is removed and viewed on the Zeiss confocal LSM 510 microscope.

Figure 18:
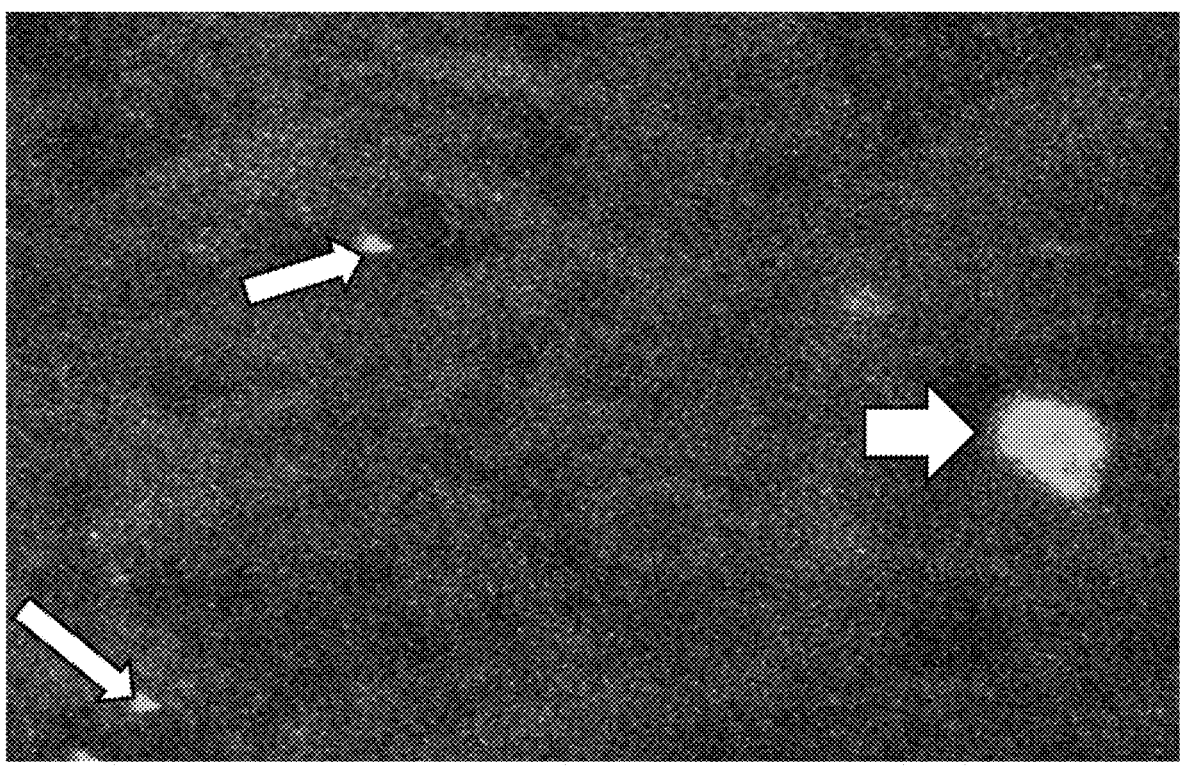
FIG. 18 shows an apical side placement of FITC insulin placed for 1 hour (not in cholostosomes) on Caco-2 cells. Image was taken at 1 hr by fluorescence microscopy, and the image here was taken of both sides of the entire cell system, Green is FITC label. Without a doubt the FITC signal stays on the apical layer in the main. However, there are signs that the FITC insulin (or the FITC fragments in the case of digested insulin) may be taken into the Caco-2 cells; note the aggregation particles (e. g. arrows). It could conceivably be chylomicron uptake of FITC or fragments of FITC insulin that create the large fluorescent structure at the bottom right (arrowhead).

FIG. 18 is an image of the apical side of the Transwell plate at 1 hr after exposure to FITC labeled insulin (i.e. not in a cholestosome)

Figure 19:
FIG. 19 shows the results of a transwell experiment; with an image taken to show baseline conditions with image of fluid at the basolateral side. Nothing was applied to the apical layer of the Caco2s (PBS/glucose only), PBS only in basolateral chamber, so the image reflects native fluorescence of the Caco-2 cell system used for our testing. Fluid was taken from the basolateral side and then imaged at 200× power. Scale is 10 um, which is 10,000 nm

In FIG. 19, the basolateral fluid is imaged on the confocal microscope. In this case the apical side had only PBS buffer and media (no FITC, no insulin, no cholestosomes) There is no visible fluorescence and this image represents image background for the basolateral images to follow.

Figure 20:
FIG. 20 shows the results of a transwell experiment with FITC cholostosomes, exactly the same conditions as previously; This time the inventors applied cholostosome with FITC in PBS to the apical side and left on for 2 hr. Based on sizing of these imaged chylomicrons, (20-30 um=27,000 nanometers (which is 100× larger than a FITC cholostosome applied to the apical side). The inventors conclude these are likely mid to large sized chylomicrons that have incorporated many of the 250 nm FITC-cholostosomes inside. Note that these images are made on only the fluid from the basolateral side, NOT imaging the prep before removing the fluid. Image here is 200× magnification. There is likely to be free FITC-cholestosomes remaining in the solution applied to the apical side, but this cannot be quantified here because this image shows just the basolateral fluid after removal from the transwell preparation, FIG. 21 shows the results of a transwell experiment, exactly the same conditions as previously, this time the inventors applied cholestosome-FITC-insulin in PBS and left on for 2 hr. Based on how sizing of the chylomicron images (at 40-60 urn, which is 40,000-60,000 nanometers), these are relatively large chylomicrons that have incorporated FITC-insulin-cholestosomes inside. Note that the inventors are imaging only the fluid from the basolateral side. Image here is taken at 200×, the scale shows 10,000 nm FIG. 22 shows the original starting concentration for FITC-insulin exposure in MCF-7 cells was 466 mcg/ml, which did not result in measurable amounts of FITC insulin inside the MCF-7 cells in row A. For the two lower figures (rows B and C), the concentration of FITC insulin cholestosome was 0.46 mcg/ml, which is the same for the experiments summarized in the last 2 figures. The 0.46 mcg/ml from FITC insulin cholestosomes (row B) produced about the same intracellular fluorescence as 466 mcg/'ml of FITC insulin without cholestosomes (row A). Compared to 466 mcg/ml of FITC insulin without cholestosomes (row A), the further processing of FITC cholestosomes by Caco-2 cells into chylomicrons, produced a robust improvement in the amount of insulin inside cells from FITC insulin cholestosome-chylomicrons (row C), much greater than 1000 fold over the amount of FITC-insulin alone, and much greater than the effect of the 0.46 mcg/ml of insulin when not processed by Caco-2 cells. Assuming the amount passing Caco2 cells was all of the insulin administered to the apical side, the concentration of insulin in the FITC insulin cholestosome chylomicron row C was the same as the insulin concentration in the middle row Row B. This particular preparation had free insulin remaining, and if transfer across Caco-2 cells was less than 100%, then these intracellular loading ratios are even greater. Clearly, FITC insulin cholestosome-chylomicrons achieves greater loading inside the cells, once again demonstrating that cholestosomes alone do allow peptides to enter cells across the cell membrane, as was earlier shown with FITC cholestosomes alone. The image in the bottom row C reflects the observed penetration of FITC insulin cholestosome chylomicrons inside cells. Not only are the cell membranes dramatically more concentrating FITC insulin in this image, but the cytoplasm of these cells is loaded with FITC insulin as well. This is after only 2 hr exposure, confirming that chylomicrons not only load massively more, they load more quickly than cholestosomes on their own.

In FIG. 20, the image is following FITC cholestosomes applied to the apical side for 2 hr, which shows small chylomicrons containing FITC in the basolateral fluid. It is important to note that this fluid was imaged after collection of the basolateral fluid and does not reflect microscopy across the entire preparation. Hence, these chylomicrons were clearly formed by the Caco2 cells.

Figure 21:
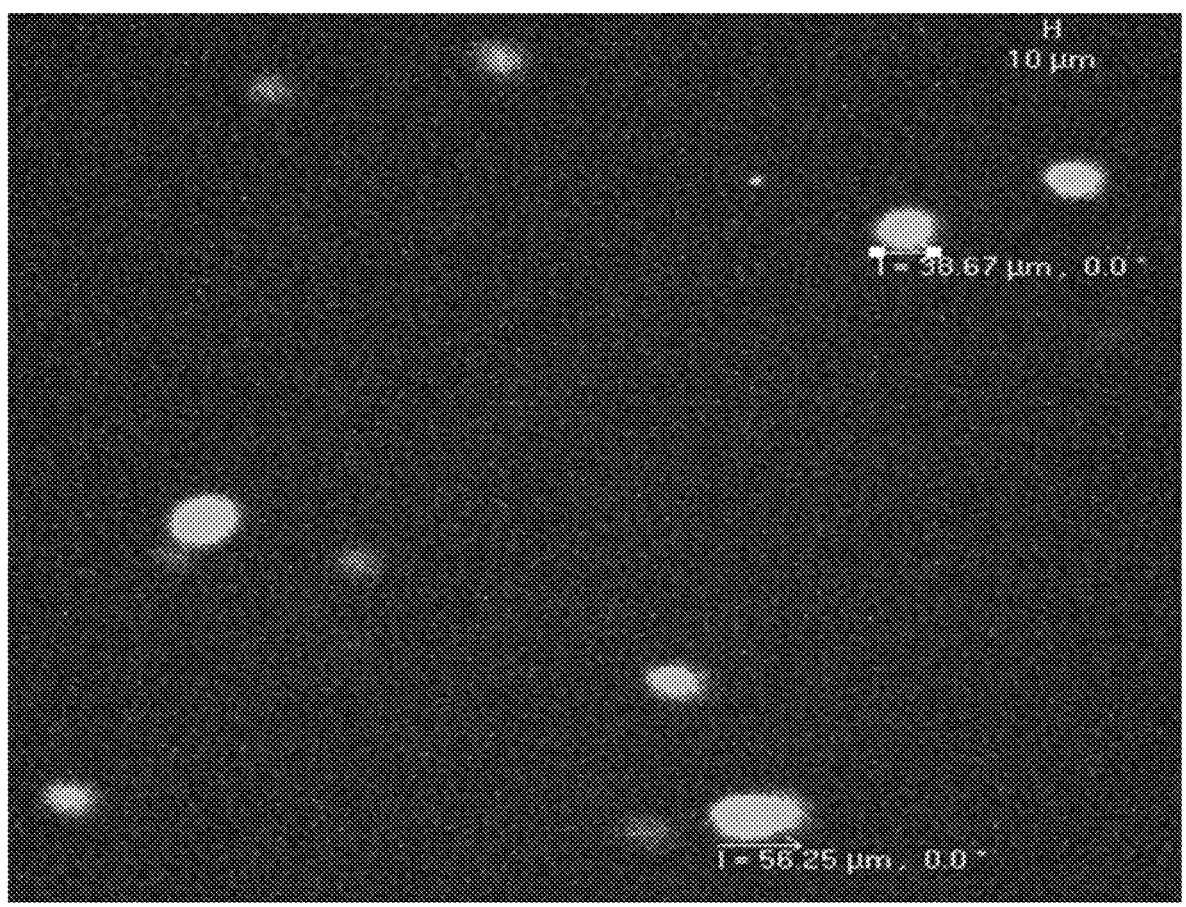

In FIG. 21, the image is following FITC insulin cholestosomes applied to the apical side for 2 hr, which shows overall larger chylomicrons containing FITC-insulin in the basolateral fluid. It is important to note that this fluid was imaged after collection of the basolateral fluid and does not reflect microscopy across the entire preparation. Hence, these FITC insulin containing chylomicrons were clearly formed by the Caco2 cells.

Summary of Cholestosome Insulin Formulation Properties
Batch: 733 and pooled batch
DLLS particle size 1700 nm not extruded
DLLS particle size: 149-274 nm after extrusion
Percent yield 13.0% of starting amount of lipid
Zeta Potential: −24.7
Loading ratio: Loading weight to weight for regular insulin was 13% insulin to 87% sum of cholesteryl myristate plus cholesteryl laurate.

Cells: MCF-7; n=400,000 cells at 24 hr in a confluent preparation; Size is 2000 nm
Cholestosomes alone; No effect on growth or viability over 24 hr
FITC alone: No effect on growth or viability over 24 hr
Insulin Alone: 3 mcg/ml of 1.5 ml volume; (4.5 mcg) No effect for 24 hr
FITC Insulin alone; 466 mcg/ml No effect on growth or viability over 24 hr (see FIG. 22)
FITC Insulin cholestosomes: 0.46 mcg/ml; No effect on growth or viability over 24 hr Insulin uptake starting by 2 hrs. (see FIG. 22)
FITC Insulin cholestosome chylomicrons: Massive uptake with all cell membranes engaged at 2 hr, free insulin in cytoplasm. Concentration inside MCF-7 cells at least 1000× over concentration outside cells.
Cells: Caco-2
Concentration apical side: Pre: 350 ul of 0.46 mcg/ml cholestosome solution on apical
FITC Cholestosomes alone; No effect on Caco-2 cells over 24 hr; chylomicrons formed as in FIG. 20
FITC insulin alone; No effect on Caco-2 cells over 24 hr; no chylomicrons formed on basolateral side as in FIG. 18
FITC alone: No effect on Caco-2 cells for 24 hr; no Chylomicrons on Basolateral side (FIG. 19)
Insulin Cholestosomes: 0.46 mcg/ml with free insulin—transferred all cholestosomes to basal side as chylomicrons. (FIG. 21)
Chylomicrons formed with FITC Insulin cholestosomes: Insulin concentration 0.46 mcg/ml or lower. (FIG. 22)
FIG. 22: FITC Insulin Cholestosome Chylomicrons FIG. 22. The original starting concentration for FITC-insulin exposure in MCF-7 cells was 466 mcg/ml, which did not result in measurable amounts of FITC insulin inside the MCF-7 cells in row A. For the two lower figures (rows B and C), the concentration of FITC insulin cholestosome was 0.46 mcg/ml, which is the same for the experiments summarized in the last 2 figures. The 0.46 mcg/ml from FITC insulin cholestosomes (row B) produced about the same intracellular fluorescence as 466 mcg/ml of FITC insulin without cholestosomes (row A). Compared to 466 mcg/ml of FITC insulin without cholestosomes (row A), the further processing of FITC insulin cholestosomes by Caco-2 cells into chylomicrons, produced a robust improvement in the amount of insulin inside cells from FITC insulin cholestosome-chylomicrons (row C), much greater than 1000 fold over the amount of FITC-insulin alone, and much greater than the effect of the 0.46 mcg/ml of insulin when not processed by Caco-2 cells. Assuming the amount passing Caco2 cells was all of the insulin administered to the apical side, the concentration of insulin in the FITC insulin cholestosome chylomicron row C was the same as the insulin concentration in the middle row Row B. This particular preparation had free insulin remaining, and if transfer across Caco-2 cells was less than 100%, then these intracellular loading ratios are even greater. Clearly. FITC insulin cholestosome-chylomicrons achieves greater loading inside the cells, once again demonstrating that cholestosomes alone do allow peptides to enter cells across the cell membrane, as was earlier shown with FITC cholestosomes alone. The image in the bottom row C reflects the observed penetration of FITC insulin cholestosome chylomicrons inside cells. Not only are the cell membranes dramatically more concentrating FITC insulin in this image, but the cytoplasm of these cells is loaded with FITC insulin as well. This is after only 2 hr exposure, confirming that chylomicrons not only load massively more, they load more quickly than cholestosomes on their own.

Figure 25:
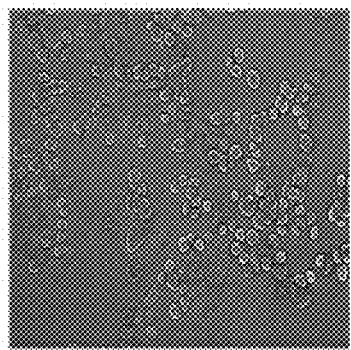
FIG. 25 shows that FITC insulin cholestosome loading of MCF-7 cells was improved over some of our previous experiments with FITC insulin cholestosomes, and here the loading was even greater from FITC insulin cholestosome chylomicrons. In all cases, processing of FITC insulin cholestosomes by Coco-2 cells into chylomicrons, produces a robust improvement in the amount of insulin inside cells from FITC insulin cholestosome-chylomicrons (row B), Not only are the cell membranes dramatically more concentrating FITC insulin in this image, but the cytoplasm of these cells is loaded with FITC insulin as well. This is after only 2 hr exposure, confirming that chylomicrons not only load massively more, they load more quickly than cholestosomes on their own. This formulation was administered to 4 mice.
Figure 25:
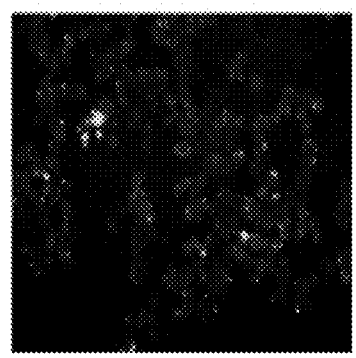
Figure 25:
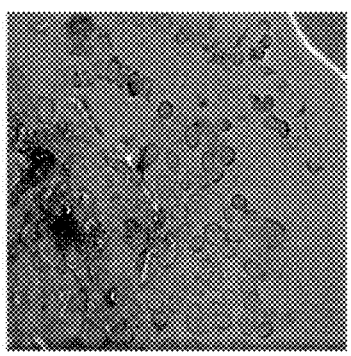
Figure 25:
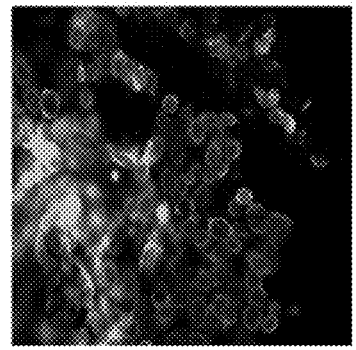

FIG. 25 FITC Insulin Cholestosome Chylomicrons Loading MCF-7 Cells

Cholestosomes containing encapsulated FITC-insulin were prepared as disclosed herein, using FITC labeled regular insulin purchased commercially. Caco-2 cells were used to ensure that Cholestosomes transfer intact insulin (i.e. insulin remains within the Cholestosome) across the enterocytes and enters chylomicrons, following which chylomicrons were detected on the basolateral side of the Caco-2 membrane. ELISA was used to demonstrate that acid protected insulin does not pass the apical Caco-2 barrier (<5%), and that all of the insulin on the basolateral side is within chylomicrons. FITC-insulin was used on the apical side to verify, that insulin alone does not pass the enterocyte barrier but that FITC insulin in cholestosomes passes the Caco2 enterocyte barrier. From these experiments, absorption efficiency was determined as the difference between basolateral side and apical side content of insulin. Further experiments compared the effect of altered pH and bile salts on the cholestosome encapsulated insulin. In addition, chylomicron stability when containing insulin loaded into cholestosomes was quantified and the conditions necessary for release of insulin from the loaded cholestosomes in vivo were studied.

In FIG. 25, the chylomicrons loaded with FITC insulin cholestosomes were placed adjacent to MCF-7 cells in order to demonstrate uptake into cells. These cells readily incorporate cholestosomes, and it appeared that distribution was uniform within the cell.

In this experiment FITC insulin cholestosome chylomicron loading of MCF-7 cells was improved over some of our previous experiments with FITC insulin cholestosomes, and here the loading was 1000× greater from FITC insulin cholestosome chylomicrons. In all cases, processing of FITC insulin cholestosomes by Caco-2 cells into chylomicrons, produces a robust improvement in the amount of insulin inside cells from FITC insulin cholestosome-chylomicrons (row B), Not only are the cell membranes dramatically more concentrating FITC insulin in this image, but the cytoplasm of these cells is loaded with FITC insulin as well. This is after only 2 hr exposure, confirming that chylomicrons not only load massively more, they load more quickly than cholestosomes on their own.

This particular formulation was administered to 4 mice.

Figure 26:
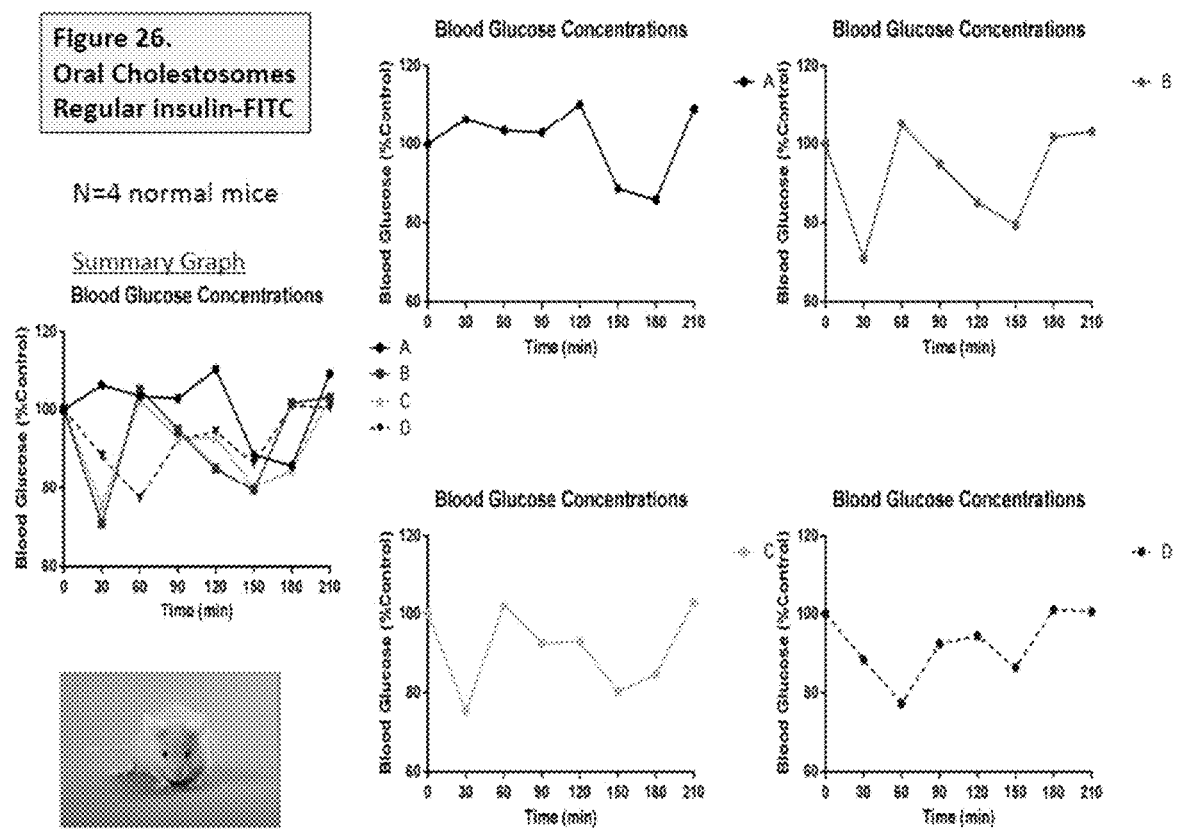
FIG. 26. Four mice were given the FITC insulin cholestosome formulation orally, with subsequent 30 minute blood glucose measurements using a glucometer. Three of the four mice dropped blood glucose substantially between 30 and 60 minutes after oral gavage with the FITC insulin cholestosome preparation. The fourth mouse did not drop blood glucose until 2 hr after administration, but had a similar decline and recovery time. Data are shown in this figure both individually and together.

FIG. 26. FITC Insulin Cholestosomes Given to 4 Mice.

Following completion of the in vitro studies in Caco-2 cells and MCF-7 cells, the cholestosome insulin formulations could be administered to mice; ELISA is used to define insulin absorption and release from chylomicrons and as a means of defining the biological residence of insulin circulating in cholestosomes in vivo.

Blood glucose is measured in the mice to define the effect of insulin in the mouse model after administration of the formulations.

FIG. 26 shows the blood glucose values of four mice, each given FITC-insulin-cholestosomes orally, with subsequent 30 minute glucose measurements using a glucometer. All mice tolerated the procedures well. In 3 of the 4 animals, the drop in blood glucose followed oral administration by 30-45 minutes. In the fourth animal, the drop in blood glucose began after 2 hrs, but had a similar decline and recovery time. In all cases, the glucose returned to baseline rapidly.

Overall, these data show oral insulin absorption and systemic effects on blood glucose, a demonstration of proof of concept for the cholestosome formulations in a murine model.

Example 5. Cholestosomes Encapsulating Anti-Cancer Agents

The use of small and large molecules in the treatment of cancer is often limited by barriers that need to be crossed in order to reach target sites inside the cell. Inventors and specialists have long sought a means of delivering small and large molecules across the cell membrane barrier, as a means of treating cancers of all types.

Thus the use of cholestosomes to promote oral absorption of anti-cancer agents and enable distribution to intracellular pathways of molecular interaction with cellular processes is of great interest, as most of the molecules to be listed below have intracellular delivery problems, oral absorption problems, or both.

Described herein is a preferred embodiment of oral delivery and intracellular loading of anti-cancer molecules using endogenously formed chylomicrons. For the most part, the listed anti-cancer agents disclosed in this example are not proteins, genetic material or the like. These are considered small molecules, and the choice of a group of small molecules active against cancer should not be considered limiting, as small molecules in general will follow the principles of encapsulation and oral absorption and intracellular uptake described herein. In all cases, one skilled in the art that pertains to the present invention will understand that there are equivalent alternative embodiments, the important feature of the present invention being reliable oral absorption and intracellular delivery of the molecule in an intact form. In each of these representative cases, the molecule will be encapsulated using the methods disclosed in example 1 and example 2, developed and tested using similar models and processes defined for antibiotics in Example 3. These methods are not limiting and physical properties of some of the representative molecules given in this example may define a pathway outside the boundaries of the Examples heretofore. As such, these will remain in the spirit of the invention.

Preferred Anti-Cancer Agents for Cholestosome Encapsulation

Representative anti-cancer molecules might include 5-Azacytidine; Alitretinoin; Altretamine; Azathioprine; Amifostine; Amsacrine; Anagrelide; Asparaginase; N-(phosphonyl)L-aspartic acid; Bexarotene (Targretin); Bleomycin; Bryostatin; Busulfan; Capecitabine; Camptothecin; Carboplatin; Carmustine; Carboprost (Carboprost Tromethamine); Carglumic Acid; Carmofur; Chlorambucil; Cladribine; Clofarabine; Clofazimine; Colchicine; Curcumin; Difluorinated Curcumin (CDF); Cyclophosphamide; Cytarabine; Cytosine arabinoside; D-Aminolevulinic Acid; Dacarbazine; Daunorubicin/Daunomycin; Deferasirox; Denileukin diftitox (Ontak); Docetaxel/Taxotere; Doxifluridine; Doxorubicin/Adriamycin; Eflornithine; Epirubicin; Elephantopin; Estramustine; Etoposide Phosphate; Fludarabine; Fluorouracil; fluoroorotic acid; Fotemustine; Gemcitabine; Gusperimus; Hydroxycarbamide; Hydroxyurea; Idarubicin/4-Demethoxy Daunorubicin; Ifosfamide; Incadronate; Irinotecan, Peg-Irinotecan; Lapatinib/Lapatinib Ditosylate; Lomustine; Masoprocol; Melphalan Hcl; Mercaptopurine; Methotrexate (Amethopterin); Methyl Aminolevulinate; Mitomycin; Mitotane; Mitoxantrone; Nimustine Hydrochloride; Octadecylphosphocholine; Ormaplatin; Oxaliplatin; Paclitaxel; Peg-asparaginase; Pemetrexed; Pentostatin/Deoxycoformycin; Porfimer Sodium; Procarbazine; Protein Kinase C inhibitors; Raltitrexed; Phenylbutyrate Sodium; Staurosporine; Streptozocin; Tafluposide; Temozolomide; Teniposide; Thioguanine; Thiotepa; Thymopoietin; Tioguanine; Tomudex; Topotecan; Tretinoin; Tropisetron hydrochloride; Uramustine (Uracil Mustard); Valrubicin; Verteporfin; Vinblastine; Vincristine; Vindesine; Vinorelbine; and/or Vorinostat.

Curcumin di-fluoride (CDF) Example

The preferred embodiment illustrative of the molecules disclosed herein is a derivative of curcumin, curcumin di-fluoride which is also called CDF. Beneficial anti-cancer properties of CDF are well described in the art (16, 85-92). One of the actions of CDF is upon the histone methyltransferase EZH2, which is a central epigenetic regulator of cell survival, proliferation, and cancer stem cell (CSC) function. EZH2 expression is increased in various human cancers, including highly aggressive pancreatic cancers, but the mechanisms underlying for its biologic effects are not yet well understood. The authors probed EZH2 function in pancreatic cancer using diflourinated-curcumin (CDF), a novel analogue of the turmeric spice component curcumin that has antioxidant properties. CDF decreased pancreatic cancer cell survival, clonogenicity, formation of pancreatospheres, invasive cell migration, and CSC function in human pancreatic cancer cells. These effects were associated with decreased expression of EZH2 and increased expression of a panel of tumor-suppressive microRNAs (miRNA), including let-7a, b, c, d, miR-26a, miR-101, miR-146a, and miR-200b, c that are typically lost in pancreatic cancer. Mechanistic investigations revealed that re-expression of miR-101 was sufficient to limit the expression of EZH2 and the proinvasive cell surface adhesion molecule EpCAM. In an orthotopic xenograft model of human pancreatic cancer, administration of CDF inhibited tumor growth in a manner associated with reduced expression of EZH2, Notch-1, CD44, EpCAM, and Nanog and increased expression of let-7, miR-26a, and miR-101. Taken together, the results indicated that CDF inhibited pancreatic cancer tumor growth and aggressiveness by targeting an EZH2-miRNA regulatory circuit for epigenetically controlled gene expression. (89)

Cholestosome encapsulated CDF can be prepared for testing according to example 1 procedures. FITC labeled CDF was used to assess biodistribution, and the aforementioned epigenetic pathways were studied when exposed to CDF cholestosomes before passage thru caco2 cells and then after, when collected chylomicrons were used in the cellular signaling pathway experiments.

Following the conclusion of the in vitro and cellular distribution experiments, the CDF cholestosomes can be applied to a mouse model for assessment of intracellular exposure and action, in order to define concentrations and dosage vs bioactivity, with un-encapsulated CDF used as a control. Both oral and IV administration were performed to define bioavailability as well as cellular uptake and localization. A second preferred embodiment is doxorubicin, itself a molecule often incorporated into liposomal drug delivery systems and widely used in the treatment of cancer

Example 6. Bevacizumab as Representative of Monoclonal Antibodies

Described herein is a preferred embodiment of oral delivery of macromolecules to include peptides, proteins including monoclonal antibodies, genetic material or the like. These are considered large biological molecules with molecular weight in excess of 6 kd and most frequently in excess of 100 kd, and the choice of a group of large biomolecules active against diseases should not be considered limiting use of the invention to a particular disease or treatment, as biomolecules in general will follow the principles of encapsulation and oral absorption and intracellular uptake described herein. In all cases, one skilled in the art that pertains to the present invention will understand that there are equivalent alternative embodiments, the important feature of the present invention being reliable oral absorption and intracellular delivery of the biomolecule in an intact form for the treatment of disease in human patients in the field of protein therapeutics. The monoclonal antibodies bevacizumab and trastuzumab have been the principle subjects of encapsulation, but these should not be considered limiting and in fact most monoclonal antibodies, being of similar length, charge and molecular weight, will behave similarly with respect to cholestosome encapsulation as described herein.

Bevacizumab in Cholestosomes

A preferred embodiment illustrative of the molecules disclosed herein is bevacizumab, selected from this list for preparation and testing of cholestosome encapsulated bevacizumab according to the principles enumerated in Example 1. The particular preparation was designed for oral use and intracellular delivery, and corresponding IV use for targeting of cell surface receptor target sites.

By way of specific example, bevacizumab cholestosomes with mean diameter of 250-10,000 nm can be prepared in the manner of the present invention, as described in Example 1, with cholesteryl ester selection from the esters disclosed as preferred in Example 2. Cholestosomes containing bevacizumab were prepared using a novel blend of two cholesteryl esters.

Alternative formulations of bevacizumab, as nanoparticles can be prepared as disclosed by Woitiski(6). These nanoparticles will be albumin coated for Caco-2 experiments, to enable what is anticipated to be maximal absorption capability, since coating improved the absorption of insulin in this particular nanoparticle formulation.

Loading and Cellular Uptake with Bevacizumab Cholestosomes.

The formulation protein bevacizumab was labeled with FITC prior to incorporation into cholestosomes in a manner described in example 1.

Cholestosome loading with Bevacizumab on a weight to weight basis was approximately 20% in particles ranging in size from 250-10,000 nm.

All formulations will be examined using confocal microscopy, scanning electron microscopy (SEM) and transwell experiments as disclosed by the inventors for insulin.

Caco-2 Cells for Testing Bevacizumab Cholestosomes

The Caco-2 cells used for the transwell experiments are cultured at 37° C. in an atmosphere of 5% $CO^2$/95% $O^2$ and 90% relative humidity in Dulbecco's Modified Eagle Medium (DMEM) supplemented with 100 IU/mL penicillin and 100 mcg/mL streptomycin, 2 mM 1-glutamine, 1% non-essential amino acids, and 10% heat inactivated fetal bovine serum. Caco-2 cells form an absorptive polarized monolayer, and develop an apical brush border and secrete enzymes after culture for 21 days.

In addition to inspection by microscopy, trans-epithelial electrical resistance is measured across cells growing on 1 $cm^2$ polycarbonate filters of trans-well diffusion cells using an epithelial volt ohmmeter to evaluate tight junctions.

Cholestosomes containing encapsulated FITC-bevacizumab were prepared as disclosed herein, using FITC labeled bevacizumab purchased commercially. Caco-2 cells were used to ensure that Cholestosomes transfer intact bevacizumab (i.e. bevacizumab remains within the Cholestosome) across the enterocytes and enters chylomicrons, following which chylomicrons were detected on the basolateral side of the Caco2 membrane. Fluorescent readings of the FITC-bevacizumab preparation were used to demonstrate that free bevacizumab does not pass the apical Caco-2 barrier (<5%), and that much of the FITC-bevacizumab placed on the apical side encapsulated in cholestosomes was actually transferred to the basal side as chylomicrons containing the FITC-bevacizumab-cholestosomes.

Based on fluorescent readings, 75% of the FITC-bevacizumab-cholestosomes added to the apical side of the Caco-2 enterocyte barrier passes the Caco2 enterocyte barrier. From these experiments, absorption efficiency was determined as the difference between basolateral side and apical side content of FITC-bevacizumab-cholestosomes. At the end of the experiment at 24 hrs, all of the fluorescence readings added up to the starting amount of fluorescence of the FITC-bevacizumab-cholestosomes, thereby achieving mass balance in the experiment itself.

Figure 23:
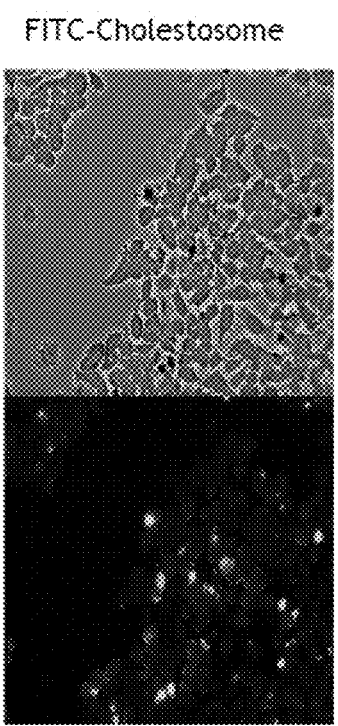
FIG. 23 shows a comparison of MCF-7 cells exposed to preparations of FITC tobramycin by bright field vs FITC fluorescence imaging shows 1) an overall successful loading of MCF-7 cells after 24 hr exposure to FITC-cholestosomes, which has been shown repeatedly in our work with cholestosomes. In 2), this response, essentially no effect from an external concentration of 700 mcg/ml; is compared with the general lack of intracellular loading of MCF-7 cells when exposed to FITC-tobramycin. This is expected because tobramycin does not enter most body cells, and any cell that takes up tobramycin actively is subject to the intracellular killing from tobramycin. This is the basis for tobramycin nephro and oto toxicity. In 3) and of great interest, when MCF-7 cells were exposed to FITC-Tobramycin-cholestosomes for 24 hr, these MCF-7 cells all died, as can be seen in the last frame at both top and bottom. The purpose here is to show how tobramycin, when it enters cells, is a general toxin to the mitochondria and when tobramycin enters even cells otherwise resistant to its intracellular effects, there is potential for intracellular uptake and harm, FIG. 24. Vancomycin entry into MCF-7 cells at 24 hr. In this series of experiments, the original starting concentrations of vancomycin were between 41 and 666 mcg/ail. In each column, the top image is the fluorescence, the bottom is the darkfield. Displayed out of this FITC-vancomycin series in column B is FITC vancomycin at 83 mcg/ml. In column A, FITC-vancomycin-cholestosomes at 0.83 mcg/ml produced greater uptake at a value 100 fold lower than the vancomycin concentration in FITC-vancomycin column B. The fluorescence image in column A shows more loading than the image in column B, indicating that the MCF-7 cellular loading ratio is more than 100× greater with FITC-vancomycin-cholestosomes. When the concentration of FITC-vancomycin was increased to 666 mcg/ml in column C, these cells are still not loading as high as those in column A. The fluorescence data on loading of FITC vancomycin is therefore approaching 1000× greater when cholestosomes are used. It should be noted that there was no effect of high amounts of FITC vancomycin cholestosomes on these MCF-7 cells. The images in the three panels confirm our observed penetration of FITC vancomycin cholestosomes inside cells. Not only are the cell membranes dramatically more concentrating FITC vancomycin in this image, but the cytoplasm of these cells is loaded with FITC vancomycin as well. This is after only 24 hr exposure, confirming that cholestosomes load massively more vancomycin in the cells.
Figure 23:
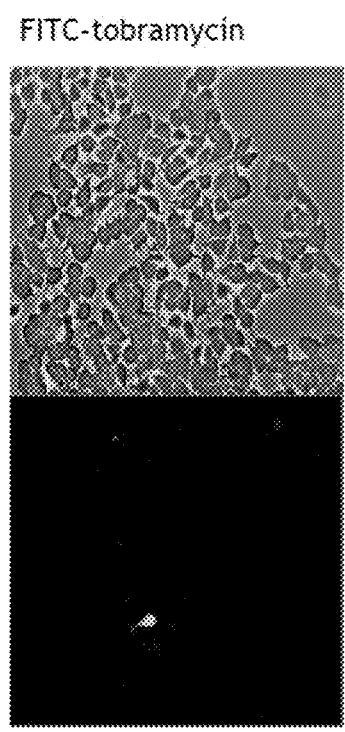
Figure 23:
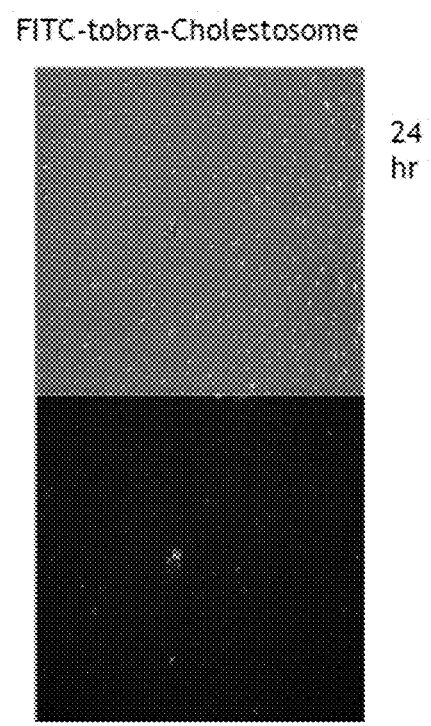

MCF-7 Cell Experiments for Bevacizumab Cholestosomes and Bevacizumab Cholestosome Chylomicrons MCF-7 cells readily take up cholestosomes as shown in FIGS. 5, 22 and 23 all control experiments for the respective constructs. Others are not shown herein. Because this is a fluorescent image, the only content of the cholestosomes in this image was from FITC encapsulated in the cholestosomes. Note the outline of the cell membrane which is loaded by cholestosomes, and in later images the uniform distribution of FITC label throughout the cell and even to include its nucleus.

MCF-7 cells are relatively resistant to bevacizumab when subjected to in-vitro testing, having an IC50 value approximately 1.0 mcg/ml. Indeed the drug functions indirectly as a cytostatic agent, which is the net effect of blocking VEGF and decreasing the supply of blood vessels to growing tumors.

Entirely expected based on the aforementioned in-vitro resistance, MCF-7 cells show no uptake of FITC-bevacizumab at external concentrations of 173 mcg/ml, a concentration approximately 10 fold higher than the typical peak when a dose of 100 mg is given to a human under treatment for carcinoma. These data are part of FIG. 27.

These same MCF-7 cells were then exposed to FITC-bevacizumab cholestosomes, prepared according to the methods in Example 1, using myristate and laurate cholesteryl esters. These cholestosomes were approximately 5000-10,000 nm in size, while an MCF-7 cell is approximately 15,000 nm in size. Both darkfield and fluorescent images of these MCF-7 cells were taken for 24 hr, and displayed in FIG. 28. These cells do not measurably take up bevacizumab cholestosomes, and it appeared that FITC-bevacizumab distribution was uniform within the cell. The MCF-7 cells remained viable for 24 hrs in this experiment, indicating that FITC bevacizumab-cholestosomes did not increase the action of bevacizumab on these cells.

The same preparation of bevacizumab-FITC-cholestosomes was then exposed to Caco-2 cells, and the resulting chylomicrons containing FITC-bevacizumab-cholestosomes were collected from the transwell basolateral side after 24 hr exposure. In this experiment, 75% of the Bevacizumab-FITC-cholestosomes passed the Caco-2 barrier and were incorporated into the resulting chylomicrons.

Because 75% of the cholestosomes were inside the chylomicrons, the MCF-7 cells were exposed to a bevacizumab concentration similar to the concentration of bevacizumab in the cholestosome preparation shown earlier. Of interest, the uptake into the MCF-7 cells was dramatically greater when chylomicrons were used for intracellular delivery of FITC-bevacizumab-cholestosomes than when delivery was from cholestosomes alone or indeed from just exposing MCF-7 cells to free bevacizumab.

Furthermore, the MCF-7 cells exposed to chylomicron delivered FITC bevacizumab were non-viable in as little time as 4 hr after exposure. This is very remarkable because there is no known cytotoxic component to the mechanism of action of bevacizumab. Heretofore, this Monoclonal antibody has a cytostatic mechanism the functions indirectly of VEGF and blood vessel growth. Furthermore, as bevacizumab is unable to enter cells, the unexpected discovery of a rapid cytotoxic pathway from intracellular delivery creates a new product and a new pathway for this old protein.

Bevacizumab Formulation Properties
- Date of manufacture: Aug. 3, 2013
- DLLS particle size 10,510 nm; not extruded
- Percent yield 20% of starting amount of lipid
- Zeta Potential: Not done for bevacizumab. Trastuzumab: 6.4
- Cells: MCF-7; 400.000 cells at 24 hr in a confluent prep. MCF-7 cell. Size is 2000 nm
- MCF-7 cells with Cholestosomes alone: No effect on growth over 24 hr
- FITC alone: No effect on growth 24 hr
- Bevacizumab Alone: not tested
- FITC bevacizumab alone; up to 173 mcg/ml: no effect on growth over 24 hr (FIG. 27)
- FITC bevacizumab cholestosomes: ~20 mcg/ml; Well tolerated by cells; visible intracellular uptake starting by 2 hrs.
- FITC bevacizumab cholestosome chylomicrons from Caco-2 cells: 15 mcg/ml on MCF-7 cells for 4 hr with complete killing of all cells in field. (FIG. 28)

Figure 27:
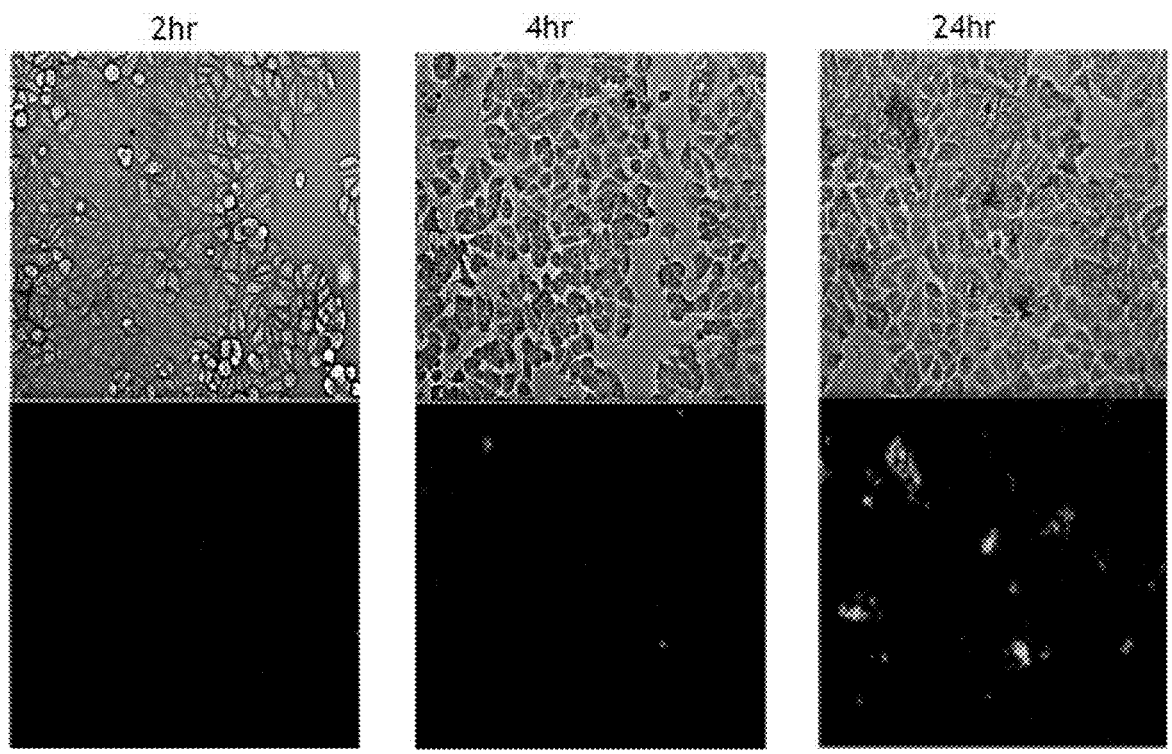
FIG. 27 shows dark field (top row) and fluorescent images at 2 hr, 4 hr and 24 hr from the application of a target concentration of 173 mcg/ml of FITC Bevacizumab to MCF-7 cells. These concentrations are 5-10 fold greater than typically observed in Bevacizumab treated patients. There was no evidence that FITC Bevacizumab integrated into the MCF-7 cell membranes of these MCF-7 cells. There was no evidence of any fluorescence uptake of FIX bevacizumab at any time point by MCF-7 cells, and there was no evidence of effect of HTC-Bevacizumab on these MCF-7 cells. The IC50 for Bevacizumab against MCF-7 cells is approximately 1.0 mcg/ml.

FIG. 27. FITC Bevacizumab on MCF-7 Cells

FIG. 27 shows the dark field (top row) and fluorescent images at 2 hr, 4 hr and 24 hr from the application of a target concentration of 173 mcg/ml of FITC Bevacizumab to MCF-7 cells. These concentrations are 5-10 fold greater than typically observed in Bevacizumab treated patients. There was no evidence that FITC bevacizumab integrated with the cell membranes of these MCF-7 cells. There was no evidence of any fluorescence uptake of FITC bevacizumab at any time point by MCF-7 cells, and there was no evidence of effect of FITC-bevacizumab on these MCF-7 cells.

Figure 28:
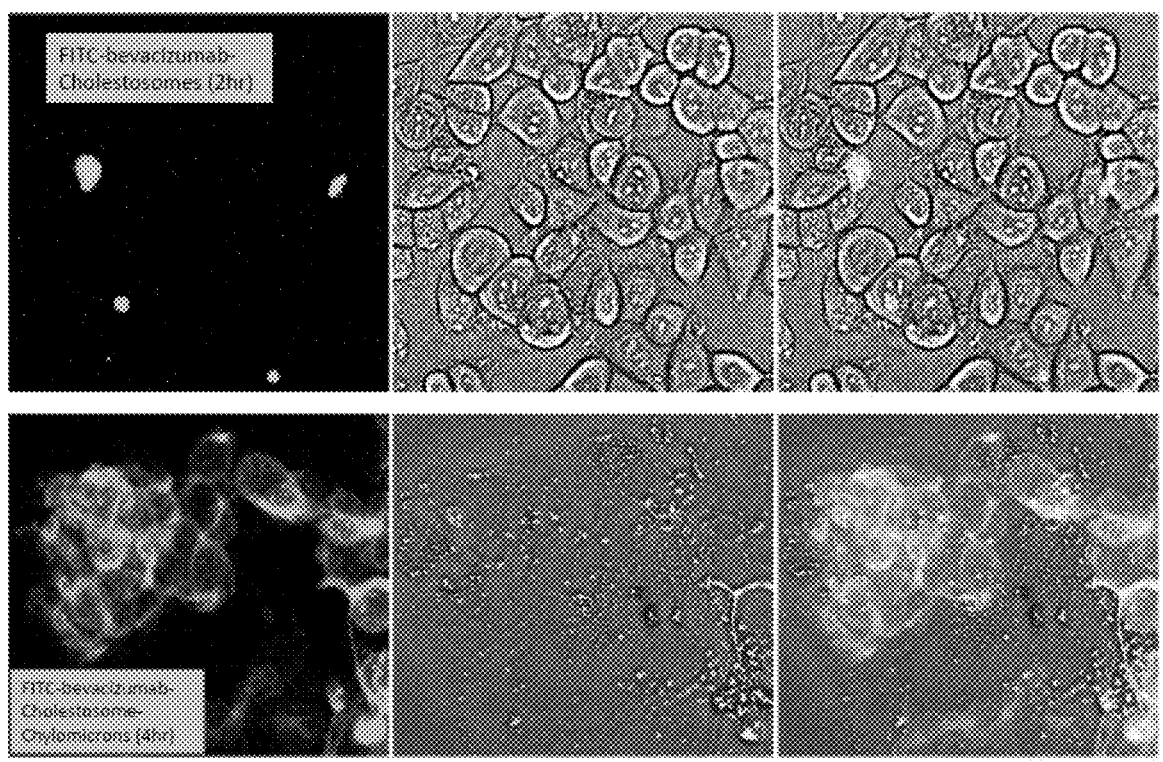
FIG. 28 shows FITC bevacizumab cholestosomes and FITC-bevacizumab cholestosome chylomicrons which were prepared and tested against MCF-7 cells. There was no effect at 21 hr, at which point the MCF-7 cells showed little uptake of FITC bevacizumab cholestosomes. As these same FITC bevacizumab cholestosomes were placed on the apical side of the Caco-2 cells and the resulting FITC bevacizumab cholestosome chylomicrons were collected, these FITC bevacizumab cholestosome chylomicrons were tested on MCF-7 cells. The first frame of the bottom row shows massive uptake of FITC bevacizumab cholestosome chylomicrons, and as shown in the next frames, all the MCF-7 cells were killed by 4 hrs into the experiment. This was completely unexpected based on the known mechanism of action of Bevacizumab FIG. 29. Shows the assembly of a lipid nanoparticle from cholesteryl myristate, cholesteryl laurate and Insulin in the hollow core.

FIG. 28 FITC Bevacizumab Cholestosome Chylomicrons Kills MCF-7 Cells

FIG. 28. In this experiment, FITC bevacizumab cholestosomes were prepared and tested against MCF-7 cells. There was no effect at 2 hr, and the cells showed no uptake of FITC bevacizumab cholestosomes. Then these same FITC bevacizumab cholestosomes were placed on the apical side of the Caco-2 cells and the resulting FITC bevacizumab cholestosome chylomicrons were tested on MCF-7 cells. The first frame of the bottom row shows massive uptake of FITC bevacizumab cholestosome chylomicrons, and the other intensely observed effect was rapid cellular killing of the MCF-7 cells, as they were all killed by 4 hrs into the experiment.

Representative Monoclonal Antibodies and Large Proteins

Representative macromolecules for conversion to oral use or for improved action inside cells by use of the present invention might include any one or combinations of those listed here, and include similar sized and charged molecules that are discovered after disclosure of the compounds listed herein: Adalimumab (Humira); Abciximab; Alemtuzumab; Bevacizumab, (Avastin); Bapineuzumab; Cetuximab; Etanercept, (Enbrel); Elotuzumab; Gemtuzumab; Inotuzumab; Kynamro™ mipomersen by Isis-Genzyme; MabThera/Rituxan; Natalizumab. Tysabri by Elan/Biogen; Necitumumab by Eli Lilly; Palivizumab (Synagis); Panitumumab; RN316 (anti-PCSK9 by Pfizer) REGN727 (anti-PCSK9 by regeneron) for lowering LDL cholesterol; Solanezumab; Trastuzumab (Herceptin); Tositumomab; T-DM1, an antibody drug conjugate by Roche/Genentech, which consists of trastuzumab (Herceptin), DM1 (emtansine) and a linker that joins DM1 to trastuzumab; T-DM1 is designed to target and inhibit HER2 signaling and deliver DM1 directly inside HER2-positive cancer cells; Zelboraf® for BRAF V600 mutation-positive metastatic melanoma; Atorolimumab; Belimumab; Brodalumab; Carlumab; Dupilumab; Fresolimumab; Golimumab; Lerdelimumab, Lirilumab; vrilimumab; Metelimumab; Morolimumab; Namilumab; Oxelumab; Placulumab; Sarilumab; Sifalimumab; Tabalumab; Ipilimumab; Tremelimumab; Nivolumab; Urelumab; Bertilimumab; Zanolimumab; Afelimomab; Elsilimomab; Faralimomab; Gavilimomab; Inolimomab; Maslimomab; Nerelimomab; Odulimomab; Telimomab; Vepalimomab; Zolimomab aritox; Basiliximab; Clenoliximab; Galiximab; Gomiliximab; Infliximab (Remicade by Janssen); Keliximab; Lumiliximab; Priliximab; Teneliximab; Vapaliximab; Aselizumab; Apolizumab; Benralizumab; Cedelizumab; Certolizumab pegol; Daclizumab; Eculizumab; Efalizumab; Epratuzumab; Erlizumab; Etrolizumab; Fontolizumab; Itolizumab; Lampalizumab; Ligelizumab; Mepolizumab; Mogamulizumab; Natalizumab; Ocrelizumab; Ofatumumab; Omalizumab; Ozoralizumab; Pascolizumab; Pateclizumab; Pexelizumab; Pidilizumab; Reslizumab; Rontalizumab; Rovelizumab; Ruplizumab; Quilizumab; Samalizumab; Siplizumab; Talizumab; Teplizumab; Tocilizumab; Toralizumab; Tregalizumab; Vatelizumab; Vedolizumab; Visilizumab; Ibalizumab; Otelixizumab; Briakinumab; Canakinumab; Fezakinumab; Secukinumab; Sirukumab; Tralokinumab; Ustekinumab; Anrukinzumab; Clazakizumab; Enokizumab; Gevokizumab; Ixekizumab; Lebrikizumab; Olokizumab; Perakizumab; Tildrakizumab; Besilesomab; Fanolesomab; Lemalesomab; and/or Sulesomab.

Example 7 Oral Universal Lipid Control Combination: Antibody to PCSK-9 with Brake and Statin A preferred embodiment illustrative of the molecules disclosed herein is Alirocumab, also known as REGN727, a monoclonal antibody against PCSK-9. Alternative monoclonal antibodies against PCSK-9 include or Evolocumab or Bococizumab by way of non-limiting example.

Alirocumab, selected from this list for preparation and testing of cholestosome encapsulated antibodies to PCSK-9 according to the principles enumerated in Example 1. The particular preparation was designed for oral use and intracellular delivery, upon knowledge and belief that PCSK-9 is an intracellular target for an antibody against this compound.

By way of specific example. Alirocumab cholestosomes with mean diameter of 250-10,000 nm can be prepared in the manner of the present invention, as described in Example 1, with cholesteryl ester selection from the esters disclosed as preferred in Example 2. Cholestosomes containing Alirocumab are prepared using a novel blend of two cholesteryl esters.

In the treatment of hyperlipidemia, it is necessary to control cholesterol, which is defined in clinical guidelines as raising HDL and lowering LDL, and in addition it is necessary to lower plasma triglycerides. The oral combination product disclosed in this example will be the only available means of complete control of all aspects of hyperlipidemia, and in addition it will remove the major disadvantage of all members of the PCSK-9 monoclonal antibody treatments, the need for bi-weekly subcutaneous injection. Oral administration of PCSK-9 monoclonal antibodies will significantly improve patient acceptance of these new therapeutic modalities.

PCSK-9 Monoclonal Antibody Component of Combination Product

Specific to the proteins of therapeutic benefit disclosed in example Oral formulation of a monoclonal antibody to PCSK9 will control elevated LDL in a potent manner, and the selected protein for oral cholestosome encapsulation.

A preferred embodiment illustrative of the molecules disclosed herein is REGN727, also known in the art as Alirocumab selected from this list for preparation and testing of cholestosome encapsulation according to the principles enumerated in Example 1. The particular preparation was designed for oral use with exposure approximately 100 mg per month of treatment.

By way of specific example, REGN727 loaded cholestosomes with mean diameter of 250-450 nm can be prepared in the manner of the present invention, as described in example 1. Cholestosomes containing REGN727 will be prepared using a novel blend of two cholesteryl esters. This construct will be used lower LDL cholesterol. The construct will be given in combination with statin drugs and optionally in combination with ileal brake hormone releasing substances.

Statin Component of Combination Product

In order to raise HDL cholesterol and lower total cholesterol, the oral REGN727 will be co-formulated with an immediate release statin drug. A listing of statins suitable for combination with oral PCSK-9 treatment includes the following: lovastatin, atorvastatin, rosuvastatin, simvastatin, fluvastatin, pitavastatin, pravastatin. By way of example a 10 mg dose of atorvastatin is preferred but the invention of the combination is not limited only to atorvastatin as most of the available statin molecules will be suitable, as all are immediate release requiring only film-coating.

Brake Component of PCSK-9 Combination Product

In order to lower triglycerides, the formulation of REGN727 and statin will optionally be combined with approximately 10 grams of an ileal brake hormone releasing substance as disclosed in US2011/0268795, the complete contents of and complete formulation of which are hereby incorporated by reference. This formulation releases the contents of the active ileal brake hormone releasing substance at the ileum of the subject, and completely controls elevated triglyceride concentrations. The results of studies performed by the inventors show that chronic daily stimulation of the ileal hormones with Aphoeline Brake™, delivered directly into the ileum, tends to stabilize and maintain the body homeostasis, as well as decrease in the fasting state the abnormal levels of insulin, glucose, triglycerides and all of the measured liver enzymes. Also the significant decrease in alpha-fetoprotein seems to indicate a decrease in inflammation of the liver. Combining the decrease in insulin resistance, triglyceride and liver inflammation with decrease in liver enzymes indicates a significant improvement in liver health and signals a role for these hormones to play in regeneration of hepatocytes and maintaining liver health. Combining these beneficial properties with a Statin and a PCSK9 monoclonal antibody offers patients a novel and comprehensive approach to control of metabolic syndrome, which is a primary underlying cause of hyperlipidemia and the resulting atherosclerotic vascular disease.

The combination product resulting from these elements would be administered to patients with hyperlipidemia on a once daily basis, with the end result being a complete control of hyperlipidemia with minimal side effects.

Example 8. Use of Cholestosomes and Chylomicrons for Delivery of siRNA

Genetic Material

In classical genetics, in a sexually reproducing organism (typically eukarya) the gamete has half the number of chromosomes of the somatic cell and the genome is a full set of chromosomes. The halving of the genetic material in gametes is accomplished by the segregation of homologous chromosomes during meiosis. Any material derived from either full or haploid chromosomes is genetic material.

The term genome can be applied specifically to mean what is stored on a complete set of nuclear DNA (i.e., the "nuclear genome") but can also be applied to what is stored within organelles that contain their own DNA, as with the "mitochondrial genome" or the "chloroplastgenome". Additionally, the genome can comprise non-chromosomal genetic elements such as viruses, plasmids, and transposable elements.

RNA and short chain RNA interference or insertions meant to alter functions of RNA are also considered genetic material for purposes of encapsulation into cholestosomes and for purposes of delivery of genetic materials to sites inside target cells.

By way of example we disclose a combination approach to the treatment of Hepatitis C, an RNA virus of genus Flaviviridae. Members of this genus have monopartite, linear, single-stranded RNA genomes of positive polarity, 9.6 to 12.3 kilobase in length. The 5'-termini of flaviviruses carry a methylated nucleotide cap, while other members of this family are uncapped and encode an internal ribosome entry site. Virus particles are enveloped and spherical, about 40-60 nm in diameter. Although over 60 viruses in this genus are known to cause disease, we wish to focus attention on Genus *Hepacivirus* (type species Hepatitis C virus)

Hepatitis C is a particularly interesting target for cholestosome therapy because this virus hides in the normally observed lipid particles and it appears necessary to follow the virus into these hiding sites if one wishes to interfere with its life cycle, invasiveness or passage between individuals.

These latter goals will lead to our preparation of specific constructs useful for the treatment of hepatitis C infections A preferred embodiment illustrative of the molecules disclosed herein is miR-122, known in the art as Miravirsen. By way of non-limiting example, alternative genetic constructs against Hepatitis C and other viruses may be used as alternative treatments against the respective viruses, as long as there is a need for a novel means of gaining access to intracellular sites and additionally to other circulating lipid particles such as chylomicron remnants which are also known to shelter the Hepatitis C virus.

miR-122 was selected for preparation and testing of cholestosome encapsulated genetic materials targeting Hepatitis C, according to the principles enumerated in Example 1. The particular preparation was designed for oral use and intracellular delivery, upon knowledge and belief that Hepatitis C infected cells are a necessary intracellular target for a genetic modifying strategy against this virus. Even with less than optimal delivery, there is clinical evidence of effective response of Hepatitis C viral infections to treatment with miR-122 constructs given parenterally to patients. These results are presented below.

By way of specific example, miR-122 cholestosomes with mean diameter of 250-10,000 nm can be prepared in the manner of the present invention, as described in Example 1, with cholesteryl ester selection from the esters disclosed as preferred in Example 2. Cholestosomes containing miR-122 are prepared using a novel blend of two cholesteryl esters.

miR-122 for HepC in Cholestosomes

The stability and propagation of hepatitis C virus (HCV) is dependent on a functional-interaction between the HCV genome and liver-expressed microRNA-122 (miR-122). MicroRNAs are small non-coding RNAs encoded by the human genome that transcriptionally and post-transcriptionally modify gene expression. The microRNA-122 (miR-122) forms the dominant microRNA in the liver and is exclusively expressed in hepatocytes. It has been implicated in multiple different processes, including lipid metabolism, cell differentiation, iron metabolism and hepatic circadian regulation. The 50 untranslated region (UTR) of HCV is highly conserved across genotypes and contains two miR-122 binding sites, disruption of which blocks HCV replication.

Miravirsen is a locked nucleic acid-modified DNA phosphorothioate anti-sense oligonucleotide that sequesters mature miR-122 in a highly stable heteroduplex, thereby inhibiting its function. As a 15 nucleotide long oligonucleotide complementary to miR-122, miravirsen can form stable heteroduplexes with miR-122. Whether miravirsen exerts its antiviral effects predominantly through sequestration of available miR-122, indirectly through disrupting lipid pathways essential to the viral lifecycle, or through other mechanisms remains under active investigation.

Its efficacy against chronic HCV infection was first shown in studies in chimpanzees, the only natural HCV animal model. Chimpanzees that received the highest, 5 mg/kg, dose through a weekly infusion had a marked decrease in plasma and liver HCV RNA, which led to clinical testing of miravirsen. Janssen and colleagues reported their findings from a phase 2a study in treatment naive non-cirrhotic patients chronically infected with HCV genotype 1. They enrolled 36 patients who were randomized to 5 weekly subcutaneous injections with three different doses of miravirsen (3, 5 or 7 mg/kg) or placebo. They found that HCV RNA showed a dose-dependent decline, with 1 (11%) patient in the 5 mg/kg and 4 (44%) patients in the 7 mg/kg groups reaching undetectable HCV RNA levels, all after the fifth dose of miravirsen. Notably, the individual response curves shown by the authors were quite variable, even with the highest dose. Three of the patients whose HCV RNA became undetectable relapsed 4-5 weeks later and one patient went on to be treated with PegIFN/RBV. The long term outcome in the remaining patient who achieved an undetectable HCV RNA at study week 14 and remained undetectable through week 18 was not reported. Adverse events were generally mild with only injection site reactions being likely related to miravirsen administration.

The most likely explanation for the rather weak and variable response of HCV patients to miravirsen is irregular cellular uptake of miravirsen. This is not surprising in that failure to reach the cellular target complicates most attempts to commercialize antisense therapy. Poor intracellular penetration is the likely reason why the dose of the miR-122 formulation was 7 mg/kg. Effective intracellular delivery of the construct using cholestosomes could lower the effective dose to values 10-100× lower. Additionally, there would be the advantage of oral use in a lower overall dosage than currently employed for use parenterally.

Cholestosome formulations will be made for the current miravirsen construct, and the likely result of successful formulation will be a dramatically improved action on HCV viral load because of effective intracellular delivery. In addition, the cholestosome formulation will be used orally, which is a great improvement over subcutaneous injection. The unique feature of oral uptake of cholestosome-miR-122 would be complemented by intracellular delivery of cholestosome-miR-122, which would make the product effective at a lower dose. These nanoparticles would enter cells via chylomicron loading, and once inside silence the Hepatitis C virus.

There is much development work to be accomplished to successfully commercialize miR-122 antisense technology. While the impact of oral therapy with cholestosome encapsulated miR-122 will produce a much improved version of this construct, it is likely that the oral formulation will be co-administered with anti-HCV drugs such as sofosbuvir (Sovaldi), and these combinations are claimed for use in treatment of HCV infections.

Furthermore, there is additional likelihood that anti-HCV drug therapy will be improved by concomitant use of Brake formulations to manage concomitant metabolic syndrome manifestations, and in principle to repair and regenerate the liver of these patients, as was further detailed in Example 7 with reference to hyperlipidemia.

With respect to the use of Brake in combination regimens for Hepatitis C, the details of these formulations and strategy are found in WO 2013/063527, published May 2, 2013, WO/2012-118712 A2, published Sep. 7, 2012 and US2012 026561, the contents of which are herein incorporated by reference.

Accordingly, the ideal combination disclosed for management of HCV in all types of patients would be oral cholestosome-miR-122 combined with oral sofosbuvir, combined with oral Brake.

An example of an oral vaccine for HCV is provided in Example 9, and this vaccine could be given to the same HCV patients as defined in the present example.

Gene Editing in the Treatment of HIV Viremia

The ability to make site-specific modifications to (or "edit") the human genome has been an objective in medicine since the recognition of the gene as the basic unit of heredity. The challenge of genome editing is the ability to generate a single double-strand break at a specific point in the DNA molecule. Numerous agents, including meganucleases, oligonucleotides that form DNA triplexes, and peptide nucleic acids, have been tested and shown to be limited by inefficiency. Another class of reagents, the zinc-finger nucleases (ZFNs), have proved versatile for genome editing, and the use of ZFNs is now well established in a number of model organisms and in human cells.

ZFNs are well suited for genome engineering because they combine the DNA recognition specificity of zinc-finger proteins (ZFPs) with the robust but restrained enzymatic activity of the cleavage domain of the restriction enzyme FokI (a nuclease). ZFPs, which provide DNA-binding specificity, contain a tandem array of $Cys_2His_2$ zinc fingers, each recognizing approximately 3 base pairs of DNA. By comparison, the bacterial type IIS restriction endonuclease, FokI, has no sequence specificity and must dimerize to cut the DNA. After the ZFN-mediated double-strand cut, the DNA can be repaired by either homologous recombination or nonhomologous end joining. Homologous recombination repairs the break while preserving the original DNA sequence. However, these cells are susceptible to recutting by ZFNs. In contrast, nonhomologous end joining can result in random insertion or deletion of nucleotides at the break site, resulting in permanent disruption of the primary DNA sequence. Therefore, nonhomologous end joining can be exploited to mutate a specific gene, leading to its functional knockout.

The design of a ZFN pair consisting of two 4-finger proteins that bind to a target site within the human chemokine (C—C motif) receptor 5 gene (CCR5) was reported previously. In preclinical tests, CCR5-modified CD4 T cells expanded and functioned normally in response to mitogens, were protected from human immunodeficiency virus (HIV) infection, and reduced HIV RNA levels in a humanized mouse model (involving xenotransplantation) of HIV infection.

Tebas and colleagues selected CCR5, which encodes a coreceptor for HIV entry, for several reasons. First, its disruption seemed likely to increase the survival of CD4 T cells; persons homozygous for a 32-bp deletion (delta32/delta32) in CCR5 are resistant to HIV infection. In vitro. CD4 T cells from such persons are highly resistant to infection with CCR5-using strains of HIV, which are the dominant strains in vivo. Moreover, persons who are heterozygous for CCR5 delta32 and who have HIV infection have a slower progression to the acquired immunodeficiency syndrome. Furthermore, the effectiveness of blocking or inhibiting CCR5 with the use of small-molecule inhibitors has been shown in humans. Finally, one person who underwent allogeneic transplantation with progenitor cells homozygous for the CCR5-delta32 deletion has remained off antiviral therapy for more than 4 years, with undetectable HIV RNA and proviral DNA in the blood, bone marrow, and rectal mucosa. Although the mechanism responsible for the apparent cure associated with this procedure remains to be established, acquired CCR5 deficiency is one possibility. Tebas now reports the partial induction of acquired genetic resistance to HIV infection after targeted gene disruption (i.e., the infusion of autologous CD4 T cells modified at CCR5 by a ZFN).

The ZFN in this case was given in association with an adenoviral vector, and cells were removed from the body prior to transfection. In the work of the inventors, overcoming these deficiencies with a functional concentration of the ZFN inside cells is feasible with a cholestosome formulation.

By way of specific example, ZFN constructs active against CCR5 in cholestosomes with mean diameter of 250-10,000 nm can be prepared in the manner of the present invention, as described in Example 1, with cholesteryl ester selection from the esters disclosed as preferred in Example 2. Cholestosomes containing ZFN are prepared using a novel blend of two cholesteryl esters selected to achieve a neutral or slightly negatively charged particle that will be taken up by enterocytes and deposited into chylomicrons.

This listing is provided by way of example of genetic material polynucleotides in cholestosome formulations across the range of molecule size in use for disease modification and treatment, and is in no way limiting on the application of cholestosomes for encapsulation of molecules of all sizes and when used for therapy of known or new diseases.

Example 9. Use of Cholestosomes and Chylomicrons Therefrom for Oral Vaccination of Virus Infections that Hide Inside Cells Transmission Life Cycle of Hepatitis C Virus Hepatitis C virus (HCV) interacts with apolipoproteins B (apoB) and E (apoE) to form infectious lipoviral particles. Response to peg-interferon is influenced by interferon-stimulated genes (ISGs) and IL28B genotype. LDL cholesterol (LDL-C) also predicts interferon response.

Hepatitis vaccines may be including adjuvants and miRNA or siRNA in the case of Hepatitis C, a virus that hides in Lipid particles. A suitable antisense therapy example from Example 8 is miR-122. It is notable that miR-122 does not elucidate a response from the immune system, and in fact it is notable that Hepatitis C does not elucidate a response from the immune system either. This is why it is so difficult to remove.

An Effective Hepatitis C Vaccine

An effective Hepatitis C vaccine will need to follow the virus thru the lipid pathway and create an immunological recognition of its presence in the cells and perhaps in the lipid particles themselves. Accordingly the use of an orally absorbed cholestosome formulation that places a vaccine construct into chylomicrons for delivery is a novel approach to vaccination.

There is no vaccine that follows the virus into all body cells, so the adaptation of the Hepatitis C viral construct into cholestosome-chylomicron delivery will be the first to use the lifecycle of a chronic infection virus against the organism directly. Use of a concomitant adjuvant will also be an optional but necessary component of the oral cholestosome Hepatitis C vaccine construct. This vaccine will be orally absorbed at the duodenum.

Oral Vaccines in Cholestosomes with or without Adjuvants

This same approach of an oral cholestosome encapsulated vaccine with adjuvant can be used for other chronic viral infections where the virus hides inside body cells, to include HIV which hides in T-lymphocytes, Herpes zoster which hides in neural tissue, and other flavivirus constructs with similar properties to hepatitis viruses.

It will also be a second preferred embodiment to deliver Hepatitis C vaccine with adjuvants orally to the Peyer's patches dendritic cells of the ileum, and for this our ileal vaccine releasing technology will be employed, as disclosed fully in PCT/US2013/031483, published as WO2013/148258 Mar. 10, 2013. Note that the disclosed vaccine there is not a cholestosome formulation, and in fact we are not anticipating that the Hepatitis C vaccine construct delivered to the ileum would be orally absorbed, nor is this perceived as a requirement for efficacy.

Thus there is potential for a novel combination product in this disclosed example, one vaccine component which is cholestosome based to penetrate into the lipid pathways of the body and which modifies the virus replication steps (and when combined with a drug, kills Hepatitis C virus directly), and a second ileal targeted therapeutic vaccine which triggers a response in dendritic T-lymphocytes in Peyer's patches where T lymphocytes are functioning as dendritic cells.

Use of these Hepatitis C vaccines in conjunction with Brake is optioned when the patient is in need of repair of fatty liver disease and early cirrhosis, which offers maximum benefit to the patient with Hepatitis C infection. Brake therapy has been disclosed in Example 7 and is incorporated herein in combination with Hepatitis C vaccines delivered by cholestosomes and delivered to the ileum for action on dendritic cells. These products may also be used in conjunction with anti-viral compounds such as sofosbuvir to reduce viral load Example 10. Use of Cholestosomes for Topical Delivery of Proteins for Wound Healing, Infections and Inflammation and for Topical Delivery of Cosmetics In the present invention, molecules used by IV injection for the treatment of infectious diseases would be generally suitable for encapsulation into cholestosomes and used topically as an ointment or cream.

Most antibiotics disclosed in example 3 need to be injected intravenously (IV), as the molecules are typically hydrophilic and not otherwise orally absorbed. Thus use in cholestosomes would enable their absorption into outer epidermidis. Numerous other small and larger molecules may be used in cholestosomes and administered topically according to the present invention including anti-fungals, anti-virals, anti-cancer and protein and peptide molecules used as growth factors.

There are many topical uses for treatments of disease that are enabled by cholestosome encapsulation of molecules. Some non-limiting examples include wound healing with topical platelet derived growth factors to include combination with other growth factors known to be beneficial to wound healing in the art.

An additional example would be the topical use of anti-TNF antibodies such as adalimumab (Humira) or Infliximab (Remicade) or many other similar molecules used topically for psoriasis and other dermal inflammatory diseases where these products are given currently by subcutaneous injection. Nearly 4.1 million people were diagnosed with some form of moderate-to-severe psoriasis in 2013. This number is expected to climb slightly to 4.4 million by 2020, with 1.5 million of the population being treated with systemic agents. A rise in the global prevalence of psoriasis, as well as an increase in the diagnosis rate resulting from improved diagnostic methods, will increase the demand for injectable monoclonal antibodies but also justify more of these products in topical cholestosome applications. As psoriasis is increasingly being recognized as a serious systemic disease with associated quality of life impairment and disability, rather than as a simply cutaneous disease, healthcare professionals will consider cholestosome encapsulated proteins and peptides as preferred over the older sub-optimal treatments. Topical administration of currently injected vaccines would also be facilitated by cholestosome formulations and the examples provided in Example 9 and previous prior art of the inventors are included here as non-limiting examples None of these molecules are orally absorbed in the native state, and in each case oral absorption would constitute a major advantage over the current need to inject them parenterally. They could also be used in the treatment of localized areas of disease thereby avoiding completely the side effects of drugs given systemically by injection.

Tobramycin for Treatment of Dermal Infections

A preferred embodiment illustrative of the molecules disclosed herein is tobramycin, selected from this list for preparation and testing of cholestosome encapsulated tobramycin according to the principles enumerated in Example 1. The particular preparation was designed for oral use, and for increasing the overall action of the antibiotic tobramycin against target gram negative bacteria such as *Pseudomonas aeruginosa*. A preparation of topical tobramycin might effectively control the *Pseudomonas* diseases malignant otitis externa or be inhaled to effectively control *Pseudomonas* in patients with cystic fibrosis.

By way of specific example, tobramycin cholestosomes with mean diameter of 250-1,000 nm were prepared in the manner of the present invention, as described in Example 1, with cholesteryl ester selection from the esters disclosed as preferred in Example 2. Cholestosomes containing tobramycin were prepared using a novel blend of two cholesteryl esters, cholesterol myristate and cholesteryl laurate.

Cholesteryl Esters Facilitate Skin Delivery

The ability of cholestosome encapsulated molecules to function in cosmetic applications is an expected discovery within the art.

Major lipids are ceramides, cholesterol and free fatty acids. These components of the stratum corneum lipid matrix play a key role in mammalian skin barrier function.

The effect of the cholesterol esters on the penetration of the stratum corneum in vivo and in vitro were studied in by Kravchenko and colleagues in rats and mice, and the effect of cholesterol esters on the fluidity of the liposome's lecithin were studied by the fluorometric method.

This study shows that inclusion of cholesterol esters to this transdermal delivery system (TDS) increased the permeability of the stratum corneum for phenazepam. They observed the maximal fluidization of the lipid environment in the presence of cholesteryl laurate, cholesteryl pelargonate, cholesteryl undecylate and cholesteryl capronate. Thus, cholesterol esters were found to be effective enhancers for transdermal delivery, and lead to the current uses as disclosed herein.

Topical Use of Curcumin for Melanoma

The cholestosome formulation of curcumin difluoride (CDF) as disclosed in example 5 may also be useful topically for treatment of dermal cancers.

Previous work with liposomes and curcumin by Chen 2012 investigated the in vitro skin permeation and in vivo antineoplastic effect of curcumin by using liposomes as the transdermal drug-delivery system. Soybean phospholipids (SPC), egg yolk phospholipids (EPC), and hydrogenated soybean phospholipids (HSPC) were selected for the preparation of different kinds of phospholipids composed of curcumin-loaded liposomes: C-SPC-L (curcumin-loaded SPC liposomes), C-EPC-L (curcumin-loaded EPC liposomes), and C-HSPC-L (curcumin-loaded HSPC liposomes). The physical properties of different liposomes were investigated as follows: photon correlation spectroscopy revealed that the average particle sizes of the three types of curcumin-loaded liposomes were 82.37±2.19 nm (C-SPC-L), 83.13±4.89 nm (C-EPC-L), and 92.42±4.56 nm (C-HSPC-L), respectively. The encapsulation efficiency values were found to be 82.32±3.91%, 81.59±2.38%, and 80.77±4.12%, respectively. An in vitro skin penetration study indicated that C-SPC-L most significantly promoted drug permeation and deposition followed by C-EPC-L, C-HSPC-L, and curcumin solution. Moreover. C-SPC-L displayed the greatest ability of all loaded liposomes to inhibit the growth of B16BL6 melanoma cells. Therefore, the C-SPC-L were chosen for further pharmacodynamic evaluation. A significant effect on anti-melanoma activity was observed with C-SPC-L, as compared to treatment with curcumin solution in vivo. These results suggest that C-SPC-L would be a promising transdermal carrier for curcumin in cancer treatment.

This example of topical treatment of cancer using a cholestosome preparation of Curcumin difluoride CDF should not be considered limiting, and any of the anti-cancer compounds disclosed in example 5 should be suitably enabled for topical use by encapsulation into cholestosomes.

Example 11. Use of Cholestosomes for Topical Delivery into the Lung

In the present invention, molecules used by IV injection for the treatment of infectious diseases would be generally suitable for encapsulation into cholestosomes and used for inhalation, where the delivery by cholestosomes would be expected to enhance penetration of the encapsulated compound into the cells lining the alveoli and bronchi. This is novel over prior art use of liposomes, which would not penetrate cells, rather serving only to hold the compound in liposomes at the site for a longer period of time without enhancing cellular penetration.

Thus this pathway of delivery by aerosolization of cholestosome encapsulated nanoparticles is rational and may greatly enhance efficacy in the treatment of pulmonary diseases such as asthma, COPD, lung carcinoma, cystic fibrosis, and even rare conditions such as Alpha-one Anti-trypsin deficiency Most antibiotics disclosed in example 3 need to be injected intravenously (IV), as the molecules are typically hydrophilic and not otherwise orally absorbed. Thus use in cholestosomes by inhalation would enable their absorption into lung directly via their enhanced cellular penetration mechanisms disclosed herein. Numerous other small and larger molecules may be used in cholestosomes and administered by inhalation according to the present invention including anti-fungals, anti-virals, anti-cancer and protein and peptide molecules used as growth factors.

There are many Pulmonary disease applications to disease treatment enabled by cholestosome encapsulation of molecules. Some non-limiting examples include repair of viral or chemical burn damage to lung alveoli with platelet derived growth factors to include combination with other growth factors known to be beneficial to wound healing in the art.

It is noted that very small nanoparticles will be needed for inclusion of cholestosome encapsulated molecules in inhalers, probably smaller than 100 nm for this application. Some non-limiting examples of compounds used in liposomes are offered as a proof of concept and a roadmap for improved intracellular delivery in the lung via cholestosome encapsulation.

Iloprost Example

Kleemann et al Pharm Res 2007: Pulmonary arterial hypertension (PAH) is a severe and progressive disease. The prostacyclin analogue iloprost is effective against PAH, but requires six to nine inhalations per day. The feasibility of liposomes to provide a sustained release formulation to reduce inhalation frequency was evaluated from a technological point of view.

Liposomal formulations consisting of di-palmitoyl-phosphatidyl-choline (DPPC), cholesterol (CH) and polyethyleneglycol-di-palmitoyl-phosphatidyl-ethanolamine (DPPE-PEG) were prepared. Their physico-chemical properties were investigated using dynamic light scattering, atomic force microscopy and differential scanning calorimetry. Stability of liposomes during aerosolization using three different nebulizers (air-jet, ultrasonic and vibrating mesh) was investigated with respect to drug loading and liposome size, pre- and post-nebulization.

The phospholipid composition affected the diameters of liposomes only slightly in the range of 200-400 nm. The highest iloprost loading (12 mcg/ml) and sufficient liposome stability (70% drug encapsulation post-nebulization) was observed for the DPPC/CH (70:30 molar ratio) liposomes. The formulation's stability was confirmed by the relatively high phase transition temperature (53 degrees C.) and unchanged particle sizes. The incorporation of DPPE-PEG in the liposomes (DPPC/CH/DPPE-PEG, 50:45:5 molar ratio) resulted in decreased stability (20-50% drug encapsulation post-nebulization) and a phase transition temperature of 35 degrees C. The vibrating mesh nebulizer offered a number of significant advantages over the other nebulizers, including the production of small aerosol droplets, high output, and the lowest deleterious physical influence upon all investigated liposomes.

Iloprost-loaded liposomes containing DPPC and CH components yield formulations which are well suited to aerosolization by the vibrating mesh nebulizer.

The use of 200-400 nm size liposomes is probably too large for successful commercial development Salbutamol Elhissi A M et al. J Pharm Pharmacol. 2006; 58:887-94. Multilamellar and oligolamellar liposomes were produced from ethanol-based soya phosphatidyl-choline proliposome formulations by addition of isotonic sodium chloride or sucrose solutions. The resultant liposomes entrapped up to 62% of available salbutamol sulfate compared with only 1.23% entrapped by conventionally prepared liposomes. Formulations were aerosolized using an air-jet nebulizer (Pari LC Plus) or a vibrating-mesh nebulizer (Aeroneb Pro small mesh, Aeroneb Pro large mesh, or Omron NE U22). All vibrating-mesh nebulizers produced aerosol droplets having larger volume median diameter (VMD) and narrower size distribution than the air-jet nebulizer. The choice of liposome dispersion medium had little effect on the performance of the Pari nebulizer. However, for the Aeroneb Pro small mesh and Omron NE U22, the use of sucrose solution tended to increase droplet VMD, and reduce aerosol mass and phospholipid outputs from the nebulizers. For the Aeroneb Pro large mesh, sucrose solution increased the VMD of nebulized droplets, increased phospholipid output and produced no effect on aerosol mass output. The Omron NE U22 nebulizer produced the highest mass output (approx. 100%) regardless of formulation, and the delivery rates were much higher for the NaCl-dispersed liposomes compared with sucrose-dispersed formulation. Nebulization produced considerable loss of entrapped drug from liposomes and this was accompanied by vesicle size reduction. Drug loss tended to be less for the vibrating-mesh nebulizers than the jet nebulizer. The large aperture size mesh (8 mum) Aeroneb Pro nebulizer increased the proportion of entrapped drug delivered to the lower stage of a twin impinger. This study has demonstrated that liposomes generated from proliposome formulations can be aerosolized in small droplets using air-jet or vibrating-mesh nebulizers. In contrast to the jet nebulizer, the performance of the vibrating-mesh nebulizers was greatly dependent on formulation. The high phospholipid output produced by the nebulizers employed suggests that both air-jet and vibrating-mesh nebulization may provide the potential of delivering liposome-entrapped or solubilized hydrophobic drugs to the airways.

Cholestosome Formulations for Inhalation

Target compounds for encapsulation in 100 nm or smaller cholestosomes and used by aerosol delivery include tobramycin for cystic fibrosis infections, curcumin difluoride for lung carcinoma, siRNA for lung carcinoma, vancomycin for pneumonia caused by MRSA, Ceftaroline for pneumonia caused by MRSA, fosfomycin for gram negative pneumonia.

Mepolizumab for Eosinophilic Asthma

A recently developed monoclonal antibody under clinical development is a further example of an inhaled cholestosome formulation of a monoclonal antibody. Mepolizumab, an investigational, fully humanized IgG1 IL-5-specific monoclonal antibody, met its primary endpoint in two Phase III studies of patients with severe eosinophilic asthma who did not see a reduction in exacerbations with high-dose inhaled corticosteroids and an additional controller drug. In the double-blind, parallel-group, multicenter, placebo-controlled, randomized MEA 115588 study, 576 patients ages 12 and older were given either 75 mg of intravenous mepolizumab or 100 mg of subcutaneous (SC) mepolizumab every four weeks over a total period of 32 weeks. Some 47 percent of patients in the 75-mg IV treatment arm, and 53 percent of patients in the 100-mg SC treatment arm met the study's primary endpoint of reductions in exacerbations. In the second double-blind, parallel-group, multicenter, placebo-controlled, randomized study, known as MEA115575, 135 patients ages 12 and older were given 100 mg of SC mepolizumab every four weeks over a total period of 24 weeks. This study met its primary endpoint of reducing oral corticosteroid use while maintaining asthma control during weeks 20-24. The company plans to file for regulatory approval for mepolizumab, which would also continue the investigational development of mepolizumab in COPD and eosinophilic granulomatosis with polyangiitis.

Clearly, an inhaled cholestosome formulation of mepolizumab would be a viable alternative to subcutaneous injection with this product, and the intracellular penetration may allow the dosage requirements to be decreased by 10-100 fold over the current requirements of 100 mg once a month. Accordingly, it is one preferred embodiment to develop a cholestosome formulation of approximately 5 mg of this monoclonal antibody for inhalation use. In addition to lower dosage requirements, the topical use of this product by inhalation would produce an immediate response in patients in need thereof, and would thereafter beneficially lower systemic exposure to a potent suppressive agent against the eosinophilic immune response, protective against a host of parasitic invaders.

This listing is provided by way of example of inhaled cholestosome formulations of known molecules across the range of molecule size in common use for disease treatment, and is in no way limiting on the application of cholestosomes for encapsulation of molecules of all sizes and when used for inhalation therapy of pulmonary diseases.

REFERENCES

1. Sinha V, Singh A, Kumar R V, Singh S, Kumria R, Bhinge J. Oral colon-specific drug delivery of protein and peptide drugs. Crit Rev Ther Drug Carrier Syst. 2007; 24(1):63-92.
2. Sinha V R, Singh A, Singh S, Bhinge J R. Compression coated systems for colonic delivery of 5-fluorouracil. J Pharm Pharmacol. 2007; 59(3):359-65.
3. Mahato R I, Narang A S, Thoma L, Miller D D. Emerging trends in oral delivery of peptide and protein drugs. Crit Rev Ther Drug Carrier Syst. 2003; 20(2-3):153-214.
4. Yamamoto A. [Improvement of intestinal absorption of peptide and protein drugs by chemical modification with fatty acids]. Nihon Rinsho. 1998; 56(3):601-7.
5. Si L, Zhao Y, Huang J, Li S, Zhai X, Li G. Calcium pectinate gel bead intended for oral protein delivery: preparation improvement and formulation development. Chem Pharm Bull (Tokyo). 2009; 57(7):663-7.
6. Woitiski C B, Sarmento B, Carvalho R A, Neufeld R J, Veiga F. Facilitated nanoscale delivery of insulin across intestinal membrane models. Int J Pharm. 2011; 412(1-2):123-31.
7. Toorisaka E, Watanabe K, Ono H, Hirata M, Kanuya N, Goto M. Intestinal patches with an immobilized solid-in-oil formulation for oral protein delivery. Acta Biomater. 2012; 8(2):653-8.
8. Kumar P S, Saini T R. Chandrasekar D, Yellepeddi V K. Ramakrishna S, Diwan P V. Novel approach for delivery of insulin loaded poly(lactide-co-glycolide) nanoparticles using a combination of stabilizers. Drug Deliv. 2007; 14(8):517-23.
9. Joseph J W, Kalitsky J. St-Pierre S, Brubaker P L. Oral delivery of glucagon-like peptide-1 in a modified polymer preparation normalizes basal glycaemia in diabetic db/db mice. Diabetologia. 2000:43(10):1319-28.
10. Diedrich G. How does hepatitis C virus enter cells? FEBS J. 2006; 273(17):3871-85.
11. Sheridan D A, Neely R D, Bassendine M F. Hepatitis C virus and lipids in the era of direct acting antivirals (DAAs). Clin Res Hepatol Gastroenterol. 2012.
12. Sheridan D A, Bridge S H, Felmlee D J, Crossey M M, Thomas H C, Taylor-Robinson S D, et al. Apolipoprotein-E and hepatitis C lipoviral particles in genotype 1 infection: evidence for an association with interferon sensitivity. J Hepatol. 2012; 57(1):32-8.
13. Feld J J. Interferon responses and spontaneous HCV clearance: is it all a matter of fat? J Hepatol. 2012; 57(1):3-5.
14. Liu S, McCormick K D, Zhao W, Zhao T, Fan D, Wang T. Human apolipoprotein E peptides inhibit hepatitis C virus entry by blocking virus binding. Hepatology. 2012; 56(2):484-91.
15. Jain S, Singh P, Mishra V. Vyas S P. Mannosylated niosomes as adjuvant-carrier system for oral genetic immunization against hepatitis B. Immunol Lett. 2005; 101(1):41-9.
16. Dandawate P R, Vyas A, Ahmad A, Banerjee S, Deshpande J, Swamy K V, et al. Inclusion complex of novel curcumin analogue CDF and beta-cyclodextrin (1:2) and its enhanced in vivo anticancer activity against pancreatic cancer. Pharm Res. 2012; 29(7):1775-86.
17. Liu G F, Zhao Q G, Si L, Cao Y G, Li G Y. Wang L X. Effects of survivin interference RNA on non-small cell lung carcinoma. Clin Invest Med. 2009; 32(6):E225.
18. Ogris M, Steinlein P, Carotta S, Brunner S, Wagner E. DNA/polyethylenimine transfection particles: influence of ligands, polymer size, and PEGylation on internalization and gene expression. AAPS PharmSci. 2001; 3(3): E21.
19. Mahato R I, Henry J, Narang A S, Sabek O, Fraga D, Kotb M, et al. Cationic lipid and polymer-based gene delivery to human pancreatic islets. Mol Ther. 2003; 7(1):89-100.
20. Oster C G, Wittmar M. Bakowsky U, Kissel T. DNA nano-carriers from biodegradable cationic branched poly- 20. esters are formed by a modified solvent displacement method. J Control Release. 2006; 111(3):371-81.
21. Reul R, Nguyen J. Biela A. Marxer E. Bakowsky U, Klebe G, et al. Biophysical and biological investigation of DNA nano-complexes with a non-toxic, biodegradable amine-modified hyperbranched polyester. Int J Pharm. 2012; 436(1-2):97-105.
22. Nguyen J, Szoka F C. Nucleic acid delivery: the missing pieces of the puzzle? Acc Chem Res. 2012; 45(7):1153-62.
23. Nguyen J, Walsh C L, Motion J P, Perttu E K, Szoka F. Controlled nucleation of lipid nanoparticles. Pharm Res. 2012; 29(8):2236-48.
24. Nguyen J, Reul R, Roesler S, Davvoub E, Schmehl T, Gessler T, et al. Amine-modified poly(vinyl alcohol)s as non-viral vectors for siRNA delivery: effects of the degree of amine substitution on physicochemical properties and knockdown efficiency. Pharm Res. 2010; 27(12):2670-82.
25. Motion J P, Nguyen J, Szoka F C. Phosphatase-triggered fusogenic liposomes for cytoplasmic delivery of cell-impermeable compounds. Angew Chem Int Ed Engl. 2012; 51(36):9047-51.
26. Walsh C L, Nguyen J, Tiffany M R, Szoka F C. Synthesis, Characterization, and Evaluation of Ionizable Lysine-Based Lipids for siRNA Delivery. Bioconjug Chem. 2012.
27. Raybould H E. Gut chemosensing: interactions between gut endocrine cells and visceral afferents. Auton Neurosci. 2010; 153(1-2):41-6.
28. Raybould H E. Nutrient sensing in the gastrointestinal tract: possible role for nutrient transporters. J Physiol Biochem. 2008; 64(4):349-56.
29. Ohtsubo K, Takamatsu S, Minowa M T, Yoshida A, Takeuchi M, Marth J D. Dietary and genetic control of glucose transporter 2 glycosylation promotes insulin secretion in suppressing diabetes. Cell. 2005; 123(7):1307-21.
30. Huang P. Altshuller Y M, Hou J C, Pessin J E, Frohman M A. Insulin-stimulated plasma membrane fusion of Glut4 glucose transporter-containing vesicles is regulated by phospholipase D1. Mol Biol Cell. 2005; 16(6):2614-23.
31. Hou J C, Pessin J E. Ins (endocytosis) and outs (exocytosis) of GLUT4 trafficking. Curr Opin Cell Biol. 2007; 19(4):466-73.
32. Hou J C, Min L, Pessin J E. Insulin granule biogenesis, trafficking and exocytosis. Vitam Horm. 2009; 80:473-506.
33. Hou J C, Williams D, Vicogne J, Pessin J E. The glucose transporter 2 undergoes plasma membrane endocytosis and lysosomal degradation in a secretagogue-dependent manner. Endocrinology. 2009; 150(9):4056-64.
34. Levy E, Mehran M. Seidman E. Caco-2 cells as a model for intestinal lipoprotein synthesis and secretion. Faseb J. 1995; 9(8):626-35.
35. van Greevenbroek M M, Erkelens D W, de Bruin T W. Caco-2 cells secrete two independent classes of lipoproteins with distinct density: effect of the ratio of unsaturated to saturated fatty acid. Atherosclerosis. 2000; 149(1):25-31.
36. Rensen P C, van Dijk M C, Havenaar E C, Bijsterbosch M K, Kruijt J K, van Berkel T J. Selective liver targeting of antivirals by recombinant chylomicrons—a new therapeutic approach to hepatitis B. Nat Med. 1995; 1(3):221-5.
37. Rensen P C, van Berkel T J. Apolipoprotein E effectively inhibits lipoprotein lipase-mediated lipolysis of chylomicron-like triglyceride-rich lipid emulsions in vitro and in vivo. J Biol Chem. 1996; 271(25):14791-9.
38. Rensen P C, Oosten M. Bilt E, Eck M, Kuiper J, Berkel T J. Human recombinant apolipoprotein E redirects lipopolysaccharide from Kupffer cells to liver parenchymal cells in rats In vivo. J Clin Invest. 1997; 99(10):2438-45.
39. Vrins C L, Ottenhoff R, van den Oever K, de Waart D R, Kruyt J K, Zhao Y, et al. Trans-intestinal cholesterol efflux is not mediated through high density lipoprotein. J Lipid Res. 2012; 53(10):2017-23.
40. Dorset D L. Cholesteryl esters of saturated fatty acids: cosolubility and fractionation of binary mixtures. J Lipid Res. 1987; 28(8):993-1005.
41. Dorset D L. Thermotropic mesomorphism of cholesteryl myristate. An electron diffraction study. J Lipid Res. 1985; 26(9):1142-50.
42. Hui D Y, Howles P N. Molecular mechanisms of cholesterol absorption and transport in the intestine. Semin Cell Dev Biol. 2005; 16(2):183-92.
43. Labonte E D, Howles P N, Granholm N A, Rojas J C, Davies J P, Ioannou Y A, et al. Class B type I scavenger receptor is responsible for the high affinity cholesterol binding activity of intestinal brush border membrane vesicles. Biochim Biophys Acta. 2007; 1771(9):1132-9.
44. Hui D Y, Labonte E D, Howles P N. Development and physiological regulation of intestinal lipid absorption. III. Intestinal transporters and cholesterol absorption. Am J Physiol Gastrointest Liver Physiol. 2008; 294(4):G839-43.
45. Labonte E D, Camarota L M, Rojas J C, Jandacek R J, Gilham D E, Davies J P, et al. Reduced absorption of saturated fatty acids and resistance to diet-induced obesity and diabetes by ezetimibe-treated and Npc1l1−/− mice. Am J Physiol Gastrointest Liver Physiol. 2008; 295(4):G776-83.
46. Howles P N. Cholesterol absorption and metabolism. Methods Mol Biol. 2010; 602:157-79.
47. Yang L, Li X, Ji Y, Kohan A B, Wang D Q, Howles P N, et al. Effect of ezetimibe on incretin secretion in response to the intestinal absorption of a mixed meal. Am J Physiol Gastrointest Liver Physiol. 2010; 299(5):G1003-11.
48. Camarota L M, Woollett L A, Howles P N. Reverse cholesterol transport is elevated in carboxyl ester lipase-knockout mice. Faseb J. 2011; 25(4):1370-7.
49. Howles P N, Hui D Y. Physiological role of hepatic NPC1L1 in human cholesterol and lipoprotein metabolism: new perspectives and open questions. J Lipid Res. 2012; 53(11):2253-5.
50. Kohan A B, Howles P N, Tso P. Methods for studying rodent intestinal lipoprotein production and metabolism. Curr Protoc Mouse Biol. 2012; 2:219-30.
51. Kindel T, Lee D M, Tso P. The mechanism of the formation and secretion of chylomicrons. Atheroscler Suppl. 2010; 11(1):11-6.
52. Fatma S, Yakubov R, Anwar K, Hussain M M. Pluronic L81 enhances triacylglycerol accumulation in the cytosol and inhibits chylomicron secretion. J Lipid Res. 2006; 47(11):2422-32.
53. Hussain M M, Kedees M H, Singh K, Athar H, Jamali N Z. Signposts in the assembly of chylomicrons. Front Biosci. 2001; 6:D320-31.
54. Pan X, Hussain M M. Gut triglyceride production. Biochim Biophys Acta. 2012:1821(5):727-35.

55. Douris N, Kojima S, Pan X, Lerch-Gaggl A F, Duong S Q, Hussain M M, et al. Nocturnin regulates circadian trafficking of dietary lipid in intestinal enterocytes. Curr Biol. 2011; 21(16):1347-55.
56. Warnakula S, Hsieh J, Adeli K, Hussain M M, Tso P, Proctor S D. New insights into how the intestine can regulate lipid homeostasis and impact vascular disease: frontiers for new pharmaceutical therapies to lower cardiovascular disease risk. Can J Cardiol. 2011; 27(2):183-91.
57. Yao Y, Lu S, Huang Y, Beeman-Black C C, Lu R, Pan X, et al. Regulation of microsomal triglyceride transfer protein by apolipoprotein A-IV in newborn swine intestinal epithelial cells. Am J Physiol Gastrointest Liver Physiol. 2011; 300(2):G357-63.
58. Iqbal J, Dai K, Seimon T, Jungreis R, Oyadomian M, Kuriakose G, et al. IRE1beta inhibits chylomicron production by selectively degrading MTP mRNA. Cell Metab. 2008; 7(5):445-55.
59. Liu R, Iqbal J, Yeang C, Wang D Q, Hussain M M, Jiang X C. Phospholipid transfer protein-deficient mice absorb less cholesterol. Arterioscler Thromb Vasc Biol. 2007; 27(9):2014-21.
60. Anwar K, Iqbal J, Hussain M M. Mechanisms involved in vitamin E transport by primary enterocytes and in vivo absorption. J Lipid Res. 2007; 48(9):2028-38.
61. Anwar K, Kayden H J, Hussain M M. Transport of vitamin E by differentiated Caco-2 cells. J Lipid Res. 2006; 47(6):1261-73.
62. Hussain M M, Fatma S, Pan X, Iqbal J. Intestinal lipoprotein assembly. Curr Opin Lipidol. 2005; 16(3): 281-5.
63. Yanez J A, Wang S W, Knemever I W, Wirth M A, Alton K B. Intestinal lymphatic transport for drug delivery. Adv Drug Deliv Rev. 2011; 63(10-11):923-42.
64. Delgado A, Lavelle E C, Hartshome M, Davis S S. PLG microparticles stabilised using enteric coating polymers as oral vaccine delivery systems. Vaccine. 1999; 17(22): 2927-38.
65. Ano G. Esquisabel A, Pastor M, Talavera A, Cedre B, Fernandez S, et al. A new oral vaccine candidate based on the microencapsulation by spray-drying of inactivated *Vibrio cholerae*. Vaccine. 2011; 29(34):5758-64.
66. Kellett G L. Comment on: Gorboulev et al. Na+-D-glucose cotransporter SGLT1 Is pivotal for intestinal glucose absorption and glucose-dependent incretin secretion. Diabetes 2012; 61:187-196. Diabetes. 2012; 61(6): e4; author reply e5.
67. Kellett G L. Alternative perspective on intestinal calcium absorption: proposed complementary actions of Ca(v)1.3 and TRPV6. Nutr Rev. 2011; 69(7):347-70.
68. Mace O J, Lister N, Morgan E, Shepherd E, Affleck J, Helliwell P, et al. An energy supply network of nutrient absorption coordinated by calcium and TiR taste receptors in rat small intestine. J Physiol. 2009; 587(Pt 1):195-210.
69. Kellett G L, Brot-Laroche E, Mace O J, Leturque A. Sugar absorption in the intestine: the role of GLUT2. Annu Rev Nutr. 2008; 28:35-54.
70. Morgan E L, Mace O J, Affleck J, Kellett G L. Apical GLUT2 and Cav1.3: regulation of rat intestinal glucose and calcium absorption. J Physiol. 2007; 580(Pt. 2):593-604.
71. Mace O J, Affleck J, Patel N, Kellett G L. Sweet taste receptors in rat small intestine stimulate glucose absorption through apical GLUT2. J Physiol. 2007; 582(Pt 1):379-92.
72. Kellett G L. Stress and intestinal sugar absorption. Am J Physiol Regul Integr Comp Physiol. 2007; 292(2):R860-1.
73. Inigo C, Patel N, Kellett G L, Barber A, Lostao M P. Luminal leptin inhibits intestinal sugar absorption in vivo. Acta Physiol (Oxf). 2007; 190(4):303-10.
74. Bailey P D, Boyd C A, Collier I D, George J P, Kellett G, L, Meredith D, et al. Affinity prediction for substrates of the peptide transporter PepT1. Chem Commun (Camb). 2006(3):323-5.
75. Kellett G L, Brot-Laroche E. Apical GLUT2: a major pathway of intestinal sugar absorption. Diabetes. 2005; 54(10):3056-62.
76. Shepherd E J, Helliwell P A, Mace O J, Morgan E L, Patel N, Kellett G L. Stress and glucocorticoid inhibit apical GLUT2-trafficking and intestinal glucose absorption in rat small intestine. J Physiol. 2004; 560(Pt 1):281-90.
77. Helliwell P A, Rumsby M G, Kellett G L. Intestinal sugar absorption is regulated by phosphorylation and turnover of protein kinase C betaII mediated by phosphatidylinositol 3-kinase- and mammalian target of rapamycin-dependent pathways. J Biol Chem. 2003; 278(31):28644-50.
78. Affleck J A, Helliwell P A, Kellett G L. Immunocytochemical detection of GLUT2 at the rat intestinal brush-border membrane. J Histochem Cytochem. 2003; 51(11): 1567-74.
79. Shepherd E J, Lister N, Affleck J A, Bronk J R, Kellett G L, Collier I D, et al. Identification of a candidate membrane protein for the basolateral peptide transporter of rat small intestine. Biochem Biophys Res Commun. 2002; 296(4):918-22.
80. Helliwell P A, Kellett G L. The active and passive components of glucose absorption in rat jejunum under low and high perfusion stress. J Physiol. 2002:544(Pt 2):579-89.
81. Burant C F, Takeda J, Brot-Laroche E, Bell G I, Davidson N O. Fructose transporter in human spermatozoa and small intestine is GLUT5. J Biol Chem. 1992; 267(21):14523-6.
82. Davidson N O, Hausman A M, Ifkovits C A, Buse J B, Gould G W, Burant C F, et al. Human intestinal glucose transporter expression and localization of GLUT5. Am J Physiol. 1992; 262(3 Pt 1):C795-800.
83. Nagamatsu S, Kornhauser J M, Burant C F, Seino S, Mayo K E, Bell G I. Glucose transporter expression in brain. cDNA sequence of mouse GLUT3, the brain facilitative glucose transporter isoform, and identification of sites of expression by in situ hybridization. J Biol Chem. 1992; 267(1):467-72.
84. Ait-Omar A, Monteiro-Sepulveda M, Poitou C, Le Gall M, Cotillard A, Gilet J, et al. GLUT2 accumulation in enterocyte apical and intracellular membranes: a study in morbidly obese human subjects and ob/ob and high fat-fed mice. Diabetes. 2011; 60(10):2598-607.
85. Ali S. Ahmad A. Aboukameel A, Bao B, Padhye S, Philip P A, et al. Increased Ras GTPase activity is regulated by miRNAs that can be attenuated by CDF treatment in pancreatic cancer cells. Cancer Lett. 2012; 319(2):173-81.
86. Ali S, Ahmad A, Banerjee S, Padhye S, Dominiak K, Schaffert J M, et al. Gemcitabine sensitivity can be induced in pancreatic cancer cells through modulation of miR-200 and miR-21 expression by curcumin or its analogue CDF. Cancer Res. 2010; 70(9):3606-17.
87. Azmi A S, Ali S, Banerjee S, Bao B, Maitah M N, Padhye S, et al. Network modeling of CDF treated pancreatic 88. Bao B, Ahmad A, Kong D, Ali S, Azmi A S, Li Y, et al. Hypoxia induced aggressiveness of prostate cancer cells is linked with deregulated expression of VEGF. IL-6 and miRNAs that are attenuated by CDF. PLoS One. 2012; 7(8):e43726.
89. Bao B, Ali S, Banerjee S, Wang Z, Logna F, Azmi A S, et al. Curcumin analogue CDF inhibits pancreatic tumor growth by switching on suppressor microRNAs and attenuating EZH2 expression. Cancer Res. 2012; 72(1): 335-45.
90. Bao B, Ali S, Kong D, Sarkar S H, Wang Z, Banejee S, et al. Anti-tumor activity of a novel compound-CDF is mediated by regulating miR-21, miR-200, and PTEN in pancreatic cancer. PLoS One. 2011; 6(3):e17850.
91. Kanwar S S, Yu Y, Nautiyal J, Patel B B, Padhye S, Sarkar F H, et al. Difluorinated-curcumin (CDF): a novel curcumin analog is a potent inhibitor of colon cancer stem-like cells. Pharm Res. 2011; 28(4):827-38.
92. Roy S, Levi E, Majumdar A P, Sarkar F H. Expression of miR-34 is lost in colon cancer which can be re-expressed by a novel agent CDF. J Hematol Oncol. 2012:5:58.
93. Wu F, Bhansali S G, Law W C, Bergey E J, Prasad P N, Morris M E. Fluorescence imaging of the lymph node uptake of proteins in mice after subcutaneous injection: molecular weight dependence. Pharm Res. 2012; 29(7): 1843-53.
94. Wu F, Bhansali S G, Tamhane M, Kumar R, Vathy L A, Ding H, et al. Noninvasive real-time fluorescence imaging of the lymphatic uptake of BSA-IRDye 680 conjugate administered subcutaneously in mice. J Pharm Sci. 2012; 101(5):1744-54.
95. Wu F, Tamhane M, Morris M E. Pharmacokinetics, lymph node uptake, and mechanistic PK model of near-infrared dye-labeled bevacizumab after IV and SC administration in mice. Aaps J. 2012; 14(2):252-61.

The invention claimed is:

1. A method of treating a patient or subject in need of treatment of a disease state or condition comprising administering to said patient or subject a composition comprising one or more active molecules encapsulated in a liquid vesicle to provide an intact loaded vesicle wherein the outer surface coating of said loaded vesicle comprises at least one cholesteryl ester obtained from cholesterol and a $C_6$-$C_{26}$ fatty acid, said molecules obtaining in an effective amount an intracellular concentration in target cells of said patient or subject which is at least 2-fold greater than the concentration obtained by said molecules in the absence of said coating, wherein said molecules are selected from the group consisting of small molecules, proteins, monoclonal antibodies, peptides, polynucleotides, oligonucleotides, nucleic acids and mixtures thereof, wherein said administration includes at least one oral, parenteral or topical dosage form and said outer surface coating of said loaded vesicle remains intact during passage of said loaded vesicle across a membrane of a cell in said patient or subject and wherein said vesicle optionally releases said one or more molecules inside target cells by the action of cholesteryl ester hydrolases on said vesicle, and said disease state or condition is Alzheimer's disease, arthritis, Crohn's disease, pancreatic cancer, melanoma, hyperlipidemia, a Hepatitis C virus infection, psoriasis, pulmonary arterial hypertension (PAH), eosinophilic asthma, an intracellular bacterial or fungal infection, metabolic syndrome or type 2 diabetes mellitus, a condition requiring initiation or increase of growth or a condition requiring a vaccine in said patient or subject.

2. The method according to claim 1 wherein said disease state or condition is Alzheimer's disease and said molecules are an insulin selected from the group consisting of regular insulin, NPH (neutral protamine Hagedorn) insulin, insulin zinc suspension, recombinant insulin, insulin glargine, insulin lispro, insulin degludec and mixtures thereof, wherein said administration is via oral or parenteral dosage form.

3. The method according to claim 1 wherein said disease state or condition is Alzheimer's, said molecule is a monoclonal antibody which targets and removes amyloid in said patient or subject.

4. The method according to claim 1 wherein said disease state or condition is arthritis and said molecule is a compound selected from the group consisting of adalimumab, etanercept and infliximab, wherein said administration is by oral or parenteral dosage form.

5. The method according to claim 1 wherein said disease state or condition is pancreatic cancer, said molecule is curcumin di-fluoride, said administration is by oral or parenteral dosage form and said targets are pancreatic cancer cells and/or associated tissue macrophages.

6. The method according to claim 1 wherein said disease state or condition is melanoma, said molecule is curcumin di-fluoride, said administration is by topical application to visible melanoma lesions on the skin and the target cells are melanoma cancer cells and/or associated tissue macrophages.

7. The method according to claim 1 wherein said disease state or condition is hyperlipidemia with low HDL and high LDL, said molecule is selected from group consisting of alirocumab, evolocumab and bococizumab, said administration is by oral or parenteral dosage form and the target cells are endothelial lining cells and/or hepatocytes that secrete PCSK9.

8. The method according to claim 1 wherein said disease state or condition is Hepatitis C, said molecule is miraversen (SPC-3649) and the target cells are Hepatitis C infected hepatocytes.

9. The method according to claim 1 wherein said disease state or condition is psoriasis, said molecule is selected from group consisting of adalimumab, etanercept and infliximab, said administration is by topical administration to the affected psoriasis patch and the target cells are TNF releasing cells.

10. The method according to claim 1 wherein said disease state or condition is pulmonary arterial hypertension (PAH), said molecule is iloprost, said administration is by oral or inhalation dosage form and the target cells are pulmonary epithelial lining cells that are prostaglandin responsive.

11. The method according to claim 1 wherein said disease state or condition is eosinophilic asthma, said molecule is mepolizumab, said administration is by oral or inhalation dosage form.

12. The method according to claim 1 wherein said disease state or condition is a bacterial or fungal infection, said molecule is selected from group consisting of butaconazole, itraconazole, miconazole, terconazole, econazole, fluconazole, isoconazole, ketoconazole, tioconazole, voriconazole, zinoconazole, bifonazole, clotrimazole, oxiconazole, fenticonazole, nystatin, amphotericin B, micafungin, caspofungin, anidulaungin, vacomycin, daptomycin, oritavancin, telavancin, WAP 8294A, dalbavancin, meropenem, ertapenem, ceftaroline, cefepime, ceftriaxone, ceftazidime, quinupristin/dalfopristin, fosfomycin, colistin, tigecycline, said administration is by oral, parenteral, topical or intravaginal dosage form and the target cells are those which are infected.

13. The method according to claim 1 wherein said disease state or condition is the risk of infection from a viral microorganism, said molecule is an antigen to the microorganism optionally including an adjuvant substance, said administration is by topical or parenteral dosage form or by oral targeting to the ileum of said patient or subject.

14. The method according to claim 1 wherein said disease state or condition is the need to initiate or increase growth in said patient, said molecule is human growth hormone, said administration is by parenteral or oral dosage form and said target cells are human growth hormone responsive cells said patient or subject.

15. The method according to claim 1 wherein said disease state or condition is metabolic syndrome or type 2 diabetes, said molecule is a compound selected from the group consisting of lixisenatide, exenatide, liraglutide, albiglutide, dulaglutide and semaglutide, wherein said administration is by oral dosage form and said target cells are GLP-1 responsive cells in said patient or subject.

* * * * *

UNITED STATES PATENT AND TRADEMARK OFFICE
CERTIFICATE OF CORRECTION

PATENT NO. : 11,633,364 B2
APPLICATION NO. : 17/337283
DATED : April 25, 2023
INVENTOR(S) : Jerome J. Schentag et al.

Page 1 of 1

It is certified that error appears in the above-identified patent and that said Letters Patent is hereby corrected as shown below:

In the Specification

Column 1, Line 8 in the section titled "RELATED APPLICATIONS" reads:
"This application is a divisional application of U.S. application Ser. No. 16/527,579 filed on Jul. 31, 2019, which is a continuation application of U.S. application Ser. No. 15/603,992 filed on May 24, 2017 of the same title, which is a continuation application of U.S. application Ser. No. 14/776,307 filed Sep. 14, 2015 of the same title, which is a United State national phase patent application based upon international patent application number PCT/US2014/027761 filed Mar. 14, 2014, which claims the benefit of priority of provisional application no. U.S. 61/783,003, filed Mar. 14, 2013, of identical title, the entire contents of which three applications are incorporated by reference herein."

Please amend to read as follows:
"This application is a divisional application of U.S. application Ser. No. 16/527,579 filed on Jul. 31, 2019, which is a continuation application of U.S. application Ser. No. 15/603,992 filed on May 24, 2017 of the same title, which is a continuation application of U.S. application Ser. No. 14/776,308 filed Sep. 14, 2015 of the same title, which is a United State national phase patent application based upon international patent application number PCT/US2014/027761 filed Mar. 14, 2014, which claims the benefit of priority of provisional application no. U.S. 61/783,003, filed Mar. 14, 2013, of identical title, the entire contents of which three applications are incorporated by reference herein."

Signed and Sealed this
Eighth Day of April, 2025

Coke Morgan Stewart
*Acting Director of the United States Patent and Trademark Office*